United States Patent
Jang et al.

(10) Patent No.: US 8,026,514 B2
(45) Date of Patent: Sep. 27, 2011

(54) DIAMINE DERIVATIVES AND ORGANIC ELECTRONIC DEVICE USING THE SAME

(75) Inventors: Hye-Young Jang, Daejeon Metropolitan (KR); Kong-Kyeom Kim, Daejeon Metropolitan (KR); Jae-Chol Lee, Daejeon Metropolitan (KR); Ji-Eun Kim, Daejeon Metropolitan (KR); Seong-So Kim, Paju-si (KR); Jin-Kyoon Park, Daejeon Metropolitan (KR); Tae-Yoon Park, Daejeon Metropolitan (KR); Eun-Ju Kim, Daejeon Metropolitan (KR); Wook-Dong Cho, Daejeon Metropolitan (KR); Byung-Sun Jeon, Seoul (KR); Jae-Soon Bae, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 12/451,063

(22) PCT Filed: Apr. 25, 2008

(86) PCT No.: PCT/KR2008/002380
§ 371 (c)(1),
(2), (4) Date: Oct. 23, 2009

(87) PCT Pub. No.: WO2008/133459
PCT Pub. Date: Nov. 6, 2008

(65) Prior Publication Data
US 2010/0187504 A1    Jul. 29, 2010

(30) Foreign Application Priority Data

Apr. 26, 2007    (KR) .................. 10-2007-0040965

(51) Int. Cl.
*H01L 29/08* (2006.01)

(52) U.S. Cl. .............................. 257/40; 257/79; 257/103
(58) Field of Classification Search .................... 257/40, 257/79, 103
See application file for complete search history.

(56) References Cited

U.S. PATENT DOCUMENTS 5,358,788 A    10/1994    Kawamura et al.
6,468,675 B1   10/2002    Ishikawa et al.
(Continued)

FOREIGN PATENT DOCUMENTS

JP    2004-323509    11/2004
(Continued)

OTHER PUBLICATIONS

Li et al., "Synthesis and properties of a 1,5-naphthalene diamine derivative", Congneng Cailiao 36(8), pp. 1235-1237, 2005. (English Abstract included).

(Continued)

*Primary Examiner* — Long Pham
(74) *Attorney, Agent, or Firm* — McKenna Long & Aldridge LLP

(57) ABSTRACT

The present invention relates to a new diamine derivative, and an organic electronic device using the same. The diamine derivative according to the present invention can serve as a hole injecting, hole transporting, electron injecting, electron transporting, or light emitting material in an organic electronic device including an organic light emitting device. Particularly, it can serve as a light emitting dopant as used alone, in particular, a blue light emitting dopant. The organic electronic device according to the present invention exhibits excellent characteristics in terms of efficiency, drive voltage, life time, and stability.

17 Claims, 1 Drawing Sheet

U.S. PATENT DOCUMENTS

| | | |
|---|---|---|
| 6,849,345 B2 | 2/2005 | Parton et al. |
| 2003/0118866 A1 | 6/2003 | Oh et al. |
| 2006/0141287 A1 | 6/2006 | Klubek et al. |
| 2006/0269781 A1* | 11/2006 | Lai et al. .................. 428/690 |

FOREIGN PATENT DOCUMENTS

| | | |
|---|---|---|
| JP | 2005-026084 | 1/2005 |
| KR | 10-2003-0035283 | 5/2003 |
| KR | 10-2006-0078119 | 7/2006 |

OTHER PUBLICATIONS

Shan et al., "Synthesis, thermal, electrochemical, and photophysical characterization of 1,5-bis(diarylamino)naphthalene derivatives as potential hole transport OLED materials", Can. J. Chem. 83, pp. 958-968, 2005.

Nelsen et al., "Estimation of Electronic Coupling for Intermolecular Electron Transfer from Cross-Reaction Data", J. Phys. Chem, 2006, 110(41), pp. 11665-11676.

Shavaleev et al., "New Ligands in the 2,2'-dipyridylamine series and their Re(I) Complexes; synthesis, structures and luminescence properties", New Journal of Chemistry, 28(3), 2004, pp. 398-405.

Sumby et al., "Coordination chemistry of di-2-pyridylamine-based bridging heterocyclic ligands: A structural study of coordination polymers and discrete dinuclear complexes", Inorganica Chimica Acta 360, 2007, pp. 2100-2114.

\* cited by examiner

[Fig. 1]
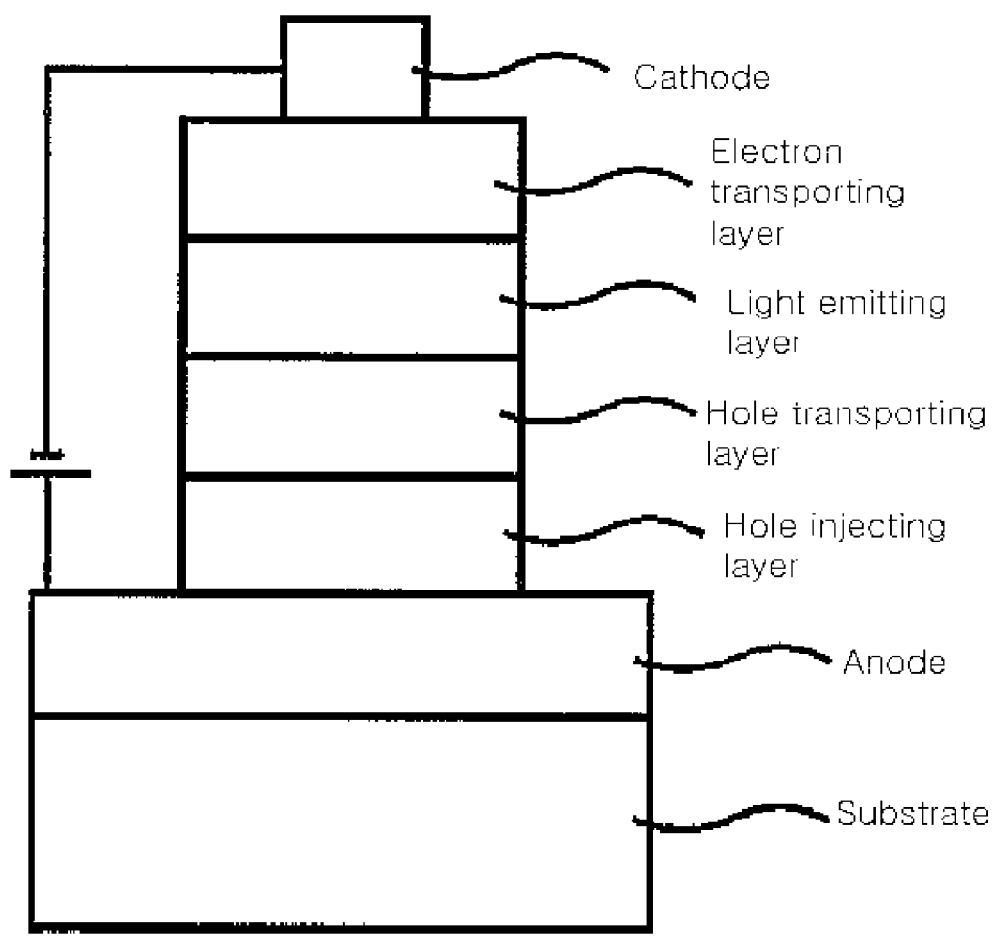

DIAMINE DERIVATIVES AND ORGANIC ELECTRONIC DEVICE USING THE SAME

This application claims the benefit of PCT/KR2008/002329 filed on Apr. 24, 2008 and Korean Patent Application No. 10-2007-0039900 filed on Apr. 24, 2007, both of which are hereby incorporated herein by reference for all purposes in their entirety.

TECHNICAL FIELD

The present invention relates to a new diamine derivative, and an organic electronic device using the same.

This application claims priority benefits from Korean Patent Application No. 10-2007-0040965, filed on Apr. 26, 2007, the entire contents of which are fully incorporated herein by reference.

BACKGROUND ART

The organic electronic device refers to a device which requires charge exchange between an electrode and an organic material using holes and electrons. The organic electronic device can be largely classified into two types according to its operation principle as follows. One type is an electronic device having a configuration in which an exciton is formed in an organic material layer by photons flown from an external light source into the device and the exciton is separated into an electron and a hole, the formed electron and hole are transported to a different electrode, respectively and used as a current source (voltage source), and the other type is an electronic device having a configuration in which a hole and/or electron are/is injected into an organic material semiconductor forming an interface with an electrode by applying a voltage or current to two or more electrodes to allow the device to operate by means of the injected electron and hole.

Examples of the organic electronic device include an organic light emitting device, an organic solar cell, an organic photoconductor (OPC) and an organic transistor, which all require a hole injecting or hole transporting material, an electron injecting or electron transporting material, or a light emitting material for driving the device.

Hereinafter, the organic light emitting device will be mainly and specifically described, but in the above-mentioned organic electronic devices, the hole injecting or hole transporting material, the electron injecting or electron transporting material, or the light emitting material injection functions according to a similar principle.

In general, the term organic light emitting phenomenon refers to a phenomenon in which electric energy is converted to light energy by means of an organic material. The organic light emitting device using the organic light emitting phenomenon has a structure usually comprising an anode, a cathode and an organic material layer interposed therebetween. Herein, the organic material layer may be mostly formed in a multilayer structure comprising layers of different materials, for example, the hole injecting layer, the hole transporting layer, the light emitting layer, the electron transporting layer, the electron injecting layer and the like, in order to improve efficiency and stability of the organic light emitting device. In the organic light emitting device having such a structure, when a voltage is applied between two electrodes, holes from the anode and electrons from a cathode are injected into the organic material layer, the holes and the electrons injected are combined together to form excitons. Further, when the excitons drop to a ground state, lights are emitted. Such the organic light emitting device is known to have characteristics such as self-luminescence, high brightness, high efficiency, law drive voltage, wide viewing angle, high contrast and high-speed response.

The materials used for the organic material layer of the organic light emitting device can be classified into a light emitting material and a charge transporting material, for example, a hole injecting material, a hole transporting material, an electron transporting material and an electron injecting material, according to their functions. The light emitting material can be classified into a high molecular weight type and a low molecular weight type, according to their molecular weight, and divided into a fluorescent material from singlet excited states and a phosphorescent material from triplet excited states according to their light emitting mechanism. Further, the light emitting material can be classified into a blue, green or red light emitting material and a yellow or orange light emitting material required for giving more natural color, according to a light emitting color.

On the other hand, an efficiency of a device is lowered owing to maximum luminescence wavelength moved to a longer wavelength due to the interaction between the molecules, the deterioration of color purity and the reduction in light emitting efficiency when only one material is used for the light emitting material, and therefore a host/dopant system can be used as the light emitting material for the purpose of enhancing the color purity and the light emitting efficiency through energy transfer. It is based on the principle that if a small amount of a dopant having a smaller energy band gap than a host which forms a light emitting layer, excitons which are generated in the light emitting layer are transported to the dopant, thus emitting a light having a high efficiency. Here, since the wavelength of the host is moved according to the wavelength of the dopant, a light having a desired wavelength can be obtained according the kind of the dopant.

In order to allow the organic light emitting device to fully exhibit the above-mentioned excellent characteristics, a material constituting the organic material layer in the device, for example, a hole injecting material, a hole transporting material, a light emitting material, an electron transporting material and an electron injecting material should be essentially composed of a stable and efficient material. However, the development of a stable and efficient organic material layer material for the organic light emitting device has not yet been fully realized. Accordingly, the development of new materials is continuously desired. The development of such a material is equally required to the above-mentioned other organic electronic devices.

DISCLOSURE OF INVENTION

Technical Problem

Accordingly, the present inventors synthesized a novel diamine derivative, and further found that the diamine derivative can be used as a hole injecting, hole transporting, electron injecting, electron transporting or light emitting material, in particular, a light emitting dopant in light emitting layer, and exhibit effects of increased efficiency, layer operating voltage, increased life-time, and higher stability of an organic electronic device, thereby completing the present invention.

It is an object of the present invention to provide a novel diamine derivative.

Further, it is another object of the present invention to provide a method for preparing a novel diamine derivative.

Further, it is still another object of the present invention to provide an organic electronic device comprising the diamine derivative.

Technical Solution

The present invention provides a diamine derivative, represented by the following Formula 1.

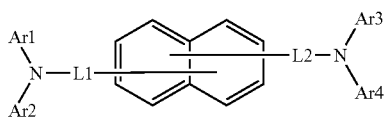

[Formula 1]

wherein L1 and L2 are same or different from each other, and are each independently a direct bond; a $C_6$~$C_{20}$ arylene group unsubstituted or substituted with one or more groups selected from the group consisting of a $C_1$~$C_{20}$ alkyl group, a $C_2$~$C_{20}$ alkenyl group, a $C_2$~$C_{20}$ alkynyl group, a $C_3$~$C_{20}$ cycloalkyl group, a $C_2$~$C_{20}$ hetero-cycloalkyl group, a $C_6$~$C_{20}$ aryl group and a $C_5$~$C_{20}$ heteroaryl group; or a $C_5$~$C_{20}$ heteroarylene group unsubstituted or substituted with one or more groups selected from the group consisting of a $C_1$~$C_{20}$ alkyl group, a $C_2$~$C_{20}$ alkenyl group, a $C_2$~$C_{20}$ alkynyl group, a $C_3$~$C_{20}$ cycloalkyl group, a $C_2$~$C_{20}$ heterocycloalkyl group, a $C_6$~$C_{20}$ aryl group and a $C_5$~$C_{20}$ heteroaryl group; and Ar1, Ar2, Ar3 and Ar4 are same or different from each other, and are each independently hydrogen, a $C_6$~$C_{30}$ aryl group unsubstituted or substituted with halogen, CN, $NO_2$, a $C_1$~$C_{20}$ alkyl group, a $C_1$~$C_{20}$ alkoxy group, a $C_6$~$C_{20}$ aryl group, a $C_5$~$C_{20}$ heteroaryl group, a $C_6$~$C_{20}$ aryl amine group, a $C_6$~$C_{20}$ aryl thiophene group, a $C_3$~$C_{20}$ cycloalkyl group, —OR, —SR, —SeR, —TeR, —BRR', —AlRR', —SiRR'R", —GeRR'R", or —SnRR'R"; a $C_5$~$C_{20}$ heterocyclic group comprising O, N or S; or a condensed ring formed by fusing a $C_4$~$C_{20}$ alkylene group with a $C_6$~$C_{20}$ aryl group, wherein R, R' and R" are same or different from each other, and are each independently hydrogen, a $C_1$~$C_{20}$ alkyl group, a $C_3$~$C_{20}$ cycloalkyl group, a $C_6$~$C_{20}$ aryl group or a $C_5$~$C_{20}$ heterocyclic group.

Advantageous Effects

The diamine derivative according to the present invention can serve as a hole injecting, hole transporting, electron injecting, electron transporting, or light emitting material in an organic electronic device including an organic light emitting device. Particularly, it can serve as a light emitting dopant as used alone, in particular, a blue light emitting dopant. The organic electronic device according to the present invention exhibits excellent characteristics in terms of efficiency, drive voltage, life time, and stability.

BRIEF DESCRIPTION OF THE DRAWINGS

FIG. 1 illustrates the structure of the organic light emitting device according to one embodiment of the present invention.

BEST MODE FOR CARRYING OUT THE INVENTION

Hereinafter, the present invention will be described in detail.

The present invention provides a diamine derivative, represented by Formula 1.

The diamine derivative represented by Formula 1 is preferably represented by any one of the following Formulae 2 to 6.

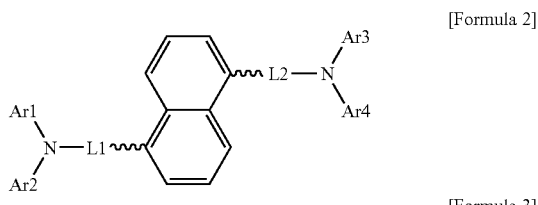

[Formula 2]

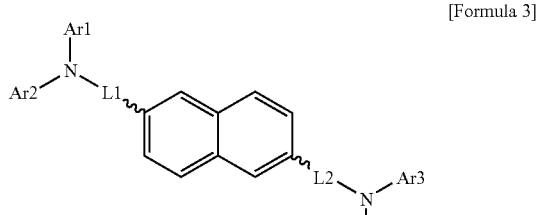

[Formula 3]

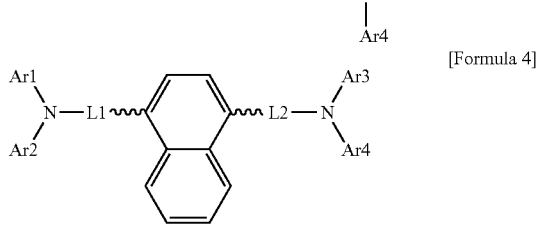

[Formula 4]

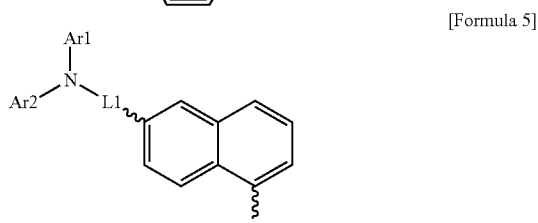

[Formula 5]

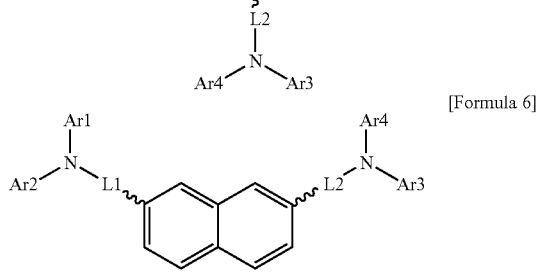

[Formula 6]

wherein L1, L2, Ar1, Ar2, Ar3 and Ar4 are the same as defined in Formula 1.

wherein L1 and L2 may be same or different from each other, and are each independently a direct bond, or selected from the group consisting of a phenylene group and a naphthylene group, but are not limited thereto.

wherein Ar1 and Ar3 may be same or different from each other, and are each independently selected from the group consisting of a phenyl group, a biphenyl group, a naphthyl group, and a phenyl group substituted with —SiRR'R" or —GeRR'R", but are not limited thereto, wherein R, R', and R" may be same or different from each other, and are each independently hydrogen, a $C_1$~$C_{20}$ alkyl group, a $C_3$~$C_{20}$ cycloalkyl group, a $C_6$~$C_{20}$ aryl group or a $C_5$~$C_{20}$ heterocyclic group.

wherein Ar2 and Ar4 may be same or different from each other, and are each independently selected from the group consisting of a phenyl group, a biphenyl group, a naphthyl group, an anthracenyl group, a pyrenyl group, a phenylenyl group, a phenyl group substituted with —SiRR'R" or —GeRR'R", a $C_5$~$C_{20}$ heterocyclic group comprising S, a $C_6$~$C_{20}$ aryl amine group, and a $C_6$~$C_{20}$ aryl group, but are not limited thereto, wherein R, R', and R" may be same or different from each other, and are each independently hydrogen, a $C_1$~$C_{20}$ alkyl group, a $C_3$~$C_{20}$ cycloalkyl group, a $C_6$~$C_{20}$ aryl group or a $C_5$~$C_{20}$ heterocyclic group.

Preferred examples of L1, L2, Ar1, Ar2, Ar3 and Ar4 in Formulae 1 to 6 are illustrated in the following Table 1, but are not limited thereto.

A variety of derivatives may be prepared in combination of the compounds of Formulae 2 to 6 and the groups illustrated in the following Table 1. For example, a compound prepared by Formula 2 and a group 1 of the following Table 1 is designated as compound 2-1.

TABLE 1 (structures only; not transcribable as text)

| | L1 | L2 | Ar1 | Ar2 | Ar3 | Ar4 |
|---|---|---|---|---|---|---|
| 8 | — | — | 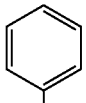 | 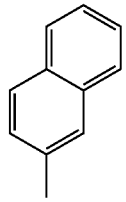 | 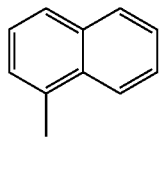 | 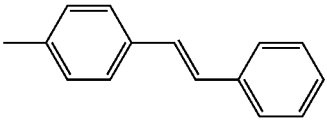 |
| 9 | — | — | 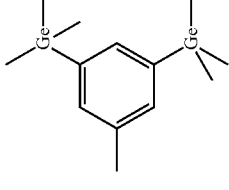 | 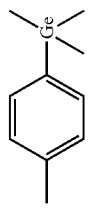 | 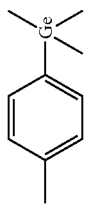 | 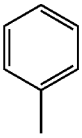 |
| 10 | — | — | 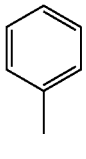 | 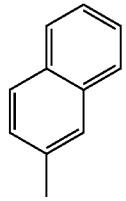 | 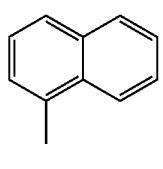 | 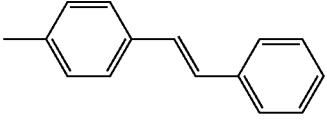 |
| 11 | — | — | | | | |

TABLE 1-continued
| | L1 | L2 | Ar1 | Ar2 | Ar3 | Ar4 |
|---|---|---|---|---|---|---|
| 12 | — | — | 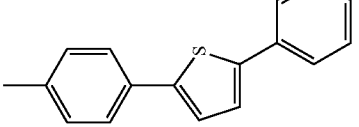 | 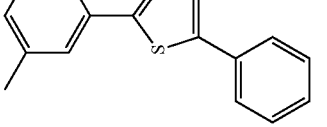 | 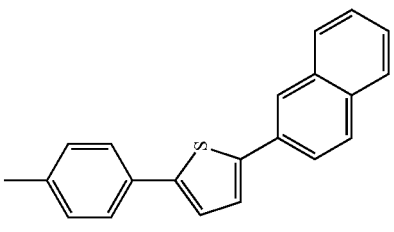 |  |
| 13 | — | — | 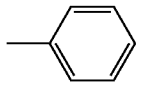 |  | 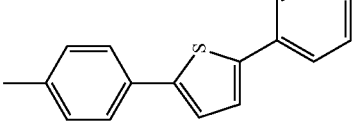 |  |
| 14 | — | — | 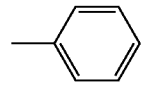 |  | 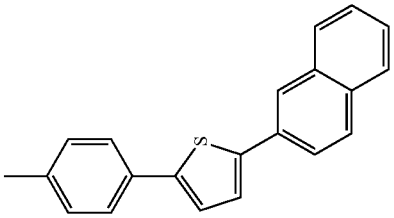 | |

TABLE 1-continued
| | L1 | L2 | Ar1 | Ar2 | Ar3 | Ar4 |
|---|---|---|---|---|---|---|
| 15 | — | — | 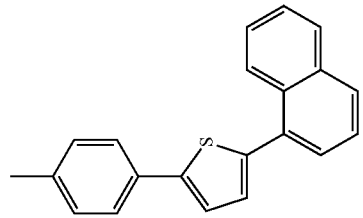 | 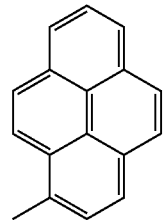 | 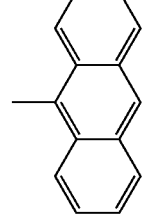 | 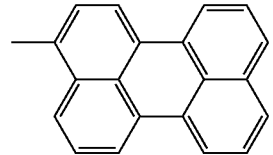 |
| 16 | — | — | 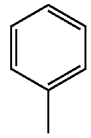 | 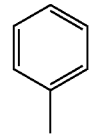 | 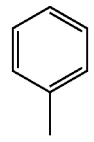 |  |
| 17 | — | — | 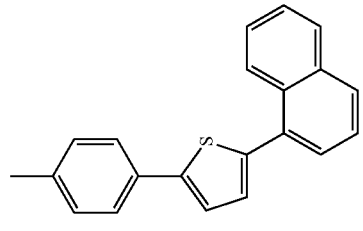 | 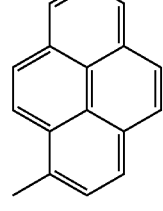 | 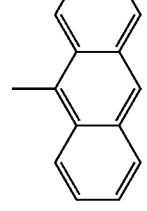 | 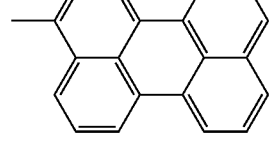 |
| 18 | — | — | 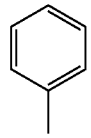 | 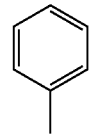 | 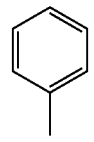 |  |

TABLE 1-continued
| | L1 | L2 | Ar1 | Ar2 | Ar3 | Ar4 |
|---|---|---|---|---|---|---|
| 19 | — | — | 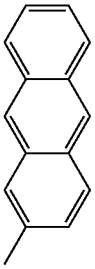 |  |  | 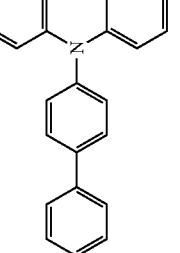 |
| 20 | — | — | 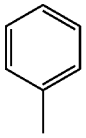 |  | 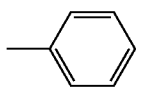 |  |
| 21 | — | — | 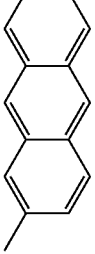 |  | | |
| 22 | — | — |  | 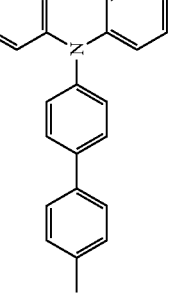 | 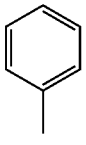 |  |
| 23 | — | — |  |  | 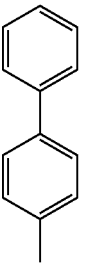 | 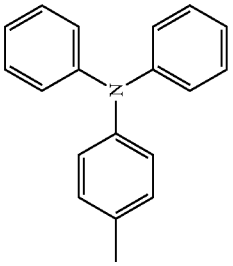 |

TABLE 1-continued
| | L1 | L2 | Ar1 | Ar2 | Ar3 | Ar4 |
|---|---|---|---|---|---|---|
| 24 | — | — | 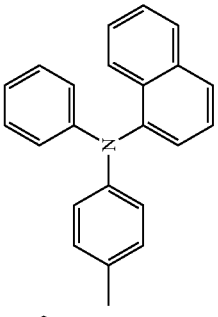 | 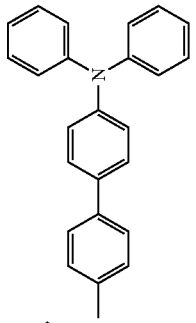 | 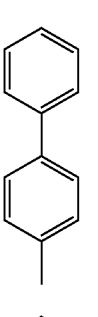 | 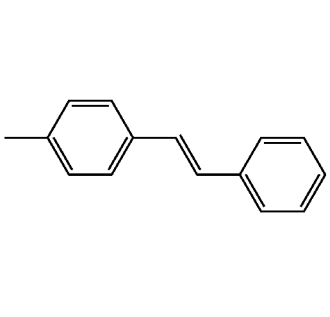 |
| 25 | — | — | 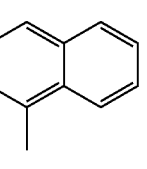 | 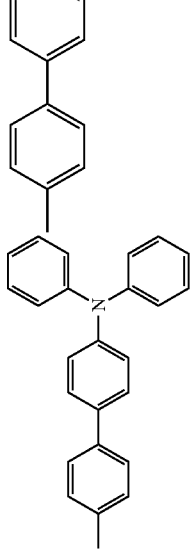 | 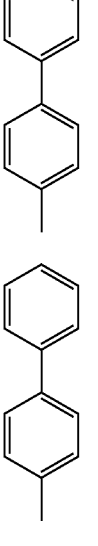 | 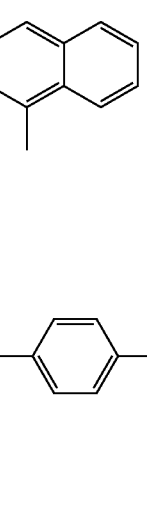 |
| 26 | — | — |  |  | 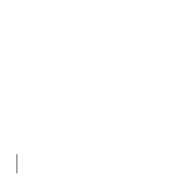 | 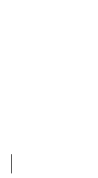 |
| 27 | — | — |  |  | 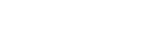 | |

TABLE 1-continued
| | L1 | L2 | Ar1 | Ar2 | Ar3 | Ar4 |
|---|---|---|---|---|---|---|
| 28 | — | — | 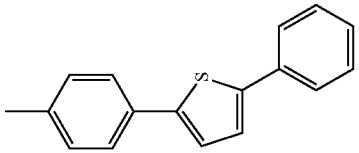 | 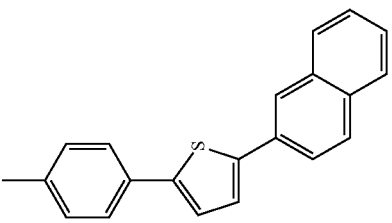 | 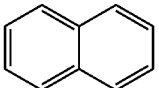 | 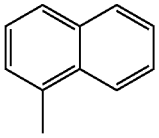 |
| 29 | — | — | 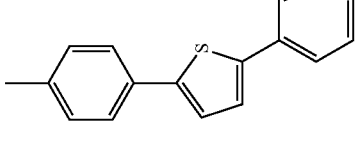 | 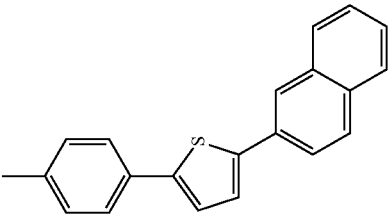 | 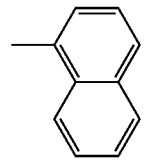 |  |

TABLE 1-continued
| | L1 | L2 | Ar1 | Ar2 | Ar3 | Ar4 |
|---|---|---|---|---|---|---|
| 30 | — | — | 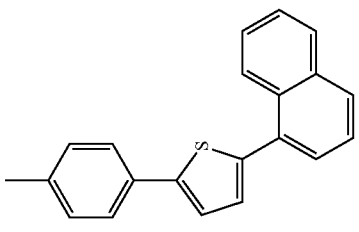 | 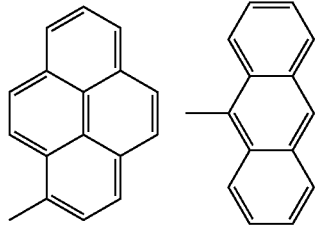 | 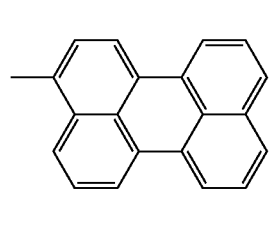 | 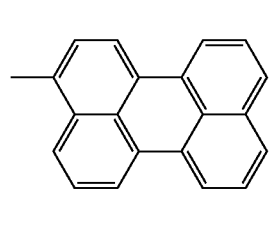 |
| 31 | — | — | 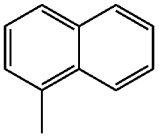 | 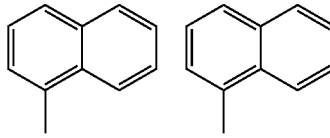 | 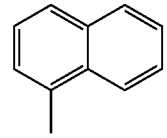 | 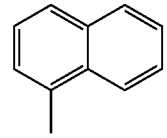 |
| 32 | — | — | 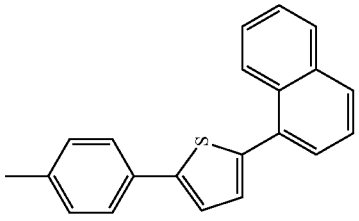 | 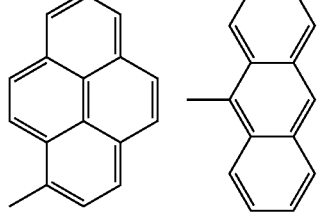 | | |
| 33 | — | — | 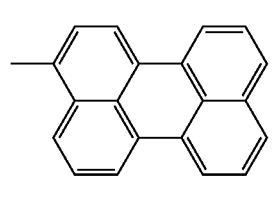 | 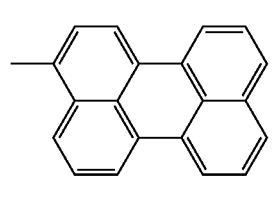 | | |

TABLE 1-continued

| | L1 | L2 | Ar1 | Ar2 | Ar3 | Ar4 |
|---|---|---|---|---|---|---|
| 34 | — | — | 1-methylnaphthalene | 2-methylanthracene | 1-methylnaphthalene | 2-methylanthracene |
| 35 | — | — | 1-methylnaphthalene | N,N-diphenyl-4-methylaniline | 1-methylnaphthalene | N,N-diphenyl-4-methylaniline |
| 36 | — | — | 1-methylnaphthalene | N-(4-methylphenyl)-N-phenyl-1-naphthylamine | 1-methylnaphthalene | N-(4-methylphenyl)-N-phenyl-1-naphthylamine |
| 37 | — | — | 1-methylnaphthalene | N,N-diphenyl-4'-methyl-4-biphenylamine | 1-methylnaphthalene | N,N-diphenyl-4'-methyl-4-biphenylamine |

TABLE 1-continued

| | L1 | L2 | Ar1 | Ar2 | Ar3 | Ar4 |
|---|---|---|---|---|---|---|
| 38 | — | — | 2-naphthyl | 4-(2-phenylethenyl)phenyl | 2-naphthyl | 4-(2-phenylethenyl)phenyl |
| 39 | — | — | 2-naphthyl | 4-(5-phenylthiophen-2-yl)phenyl | 2-naphthyl | 4-(5-phenylthiophen-2-yl)phenyl |

TABLE 1-continued
| | L1 | L2 | Ar1 | Ar2 | Ar3 | Ar4 |
|---|---|---|---|---|---|---|
| 40 | — | — | 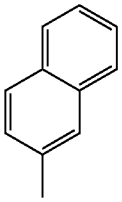 | 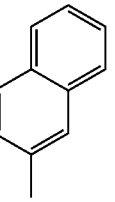 | 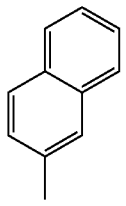 |  |
| 41 | — | — | 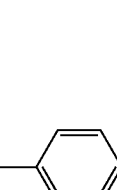 |  | 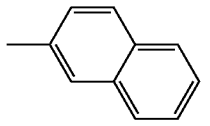 | 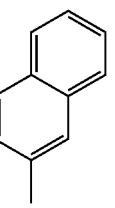 |
| 42 | — | — | 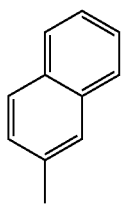 |  | 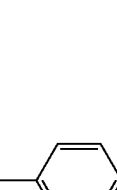 | 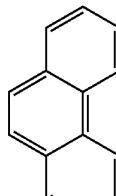 |

TABLE 1-continued
| | L1 | L2 | Ar1 | Ar2 | Ar3 | Ar4 |
|---|---|---|---|---|---|---|
| 43 | — | — | 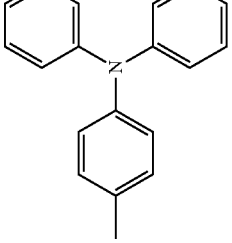 | 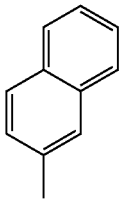 |  | 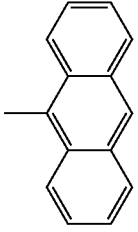 |
| 44 | — | — | 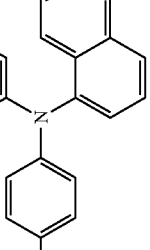 |  | 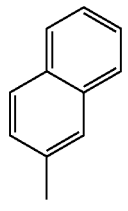 | 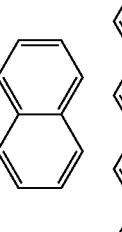 |
| 45 | — | — | 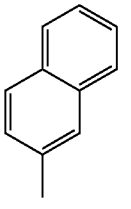 |  | 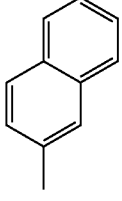 | 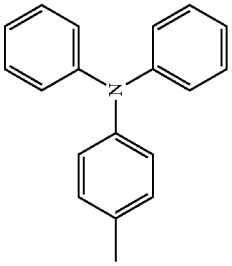 |
| 46 | — | — | 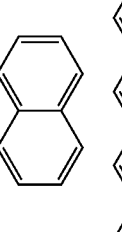 | 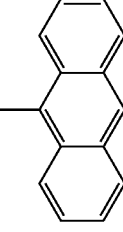 | 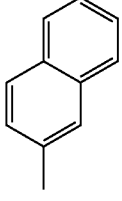 | 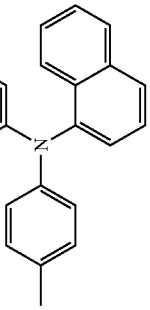 |
| 47 | — | — | 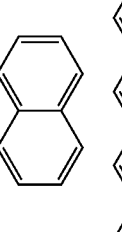 | 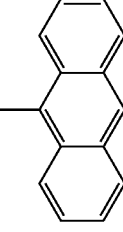 | 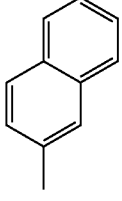 | 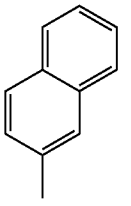 |

TABLE 1-continued
| | L1 | L2 | Ar1 | Ar2 | Ar3 | Ar4 |
|---|---|---|---|---|---|---|
| 48 | — | — | 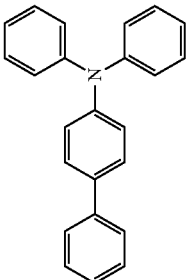 | 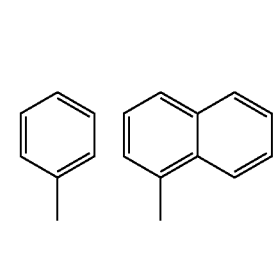 | 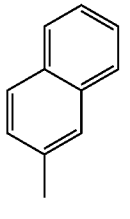 | 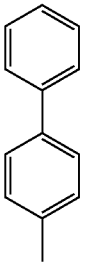 |
| 49 | — | 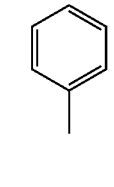 | 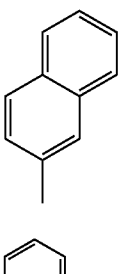 | 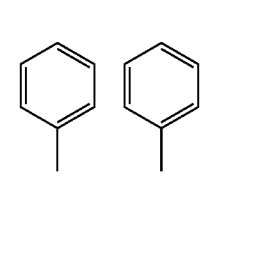 | 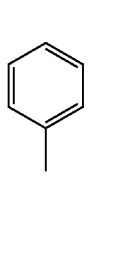 | 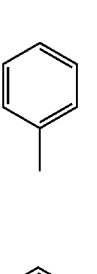 |
| 50 | — |  |  | 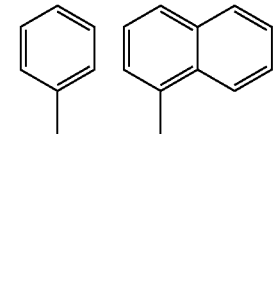 | 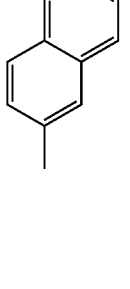 | 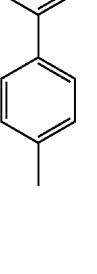 |
| 51 | — |  |  | 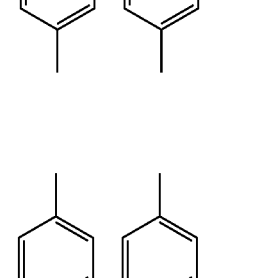 | 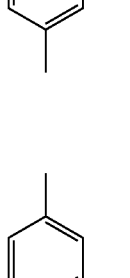 | 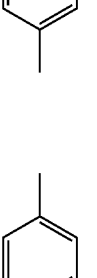 |
| 52 | — | 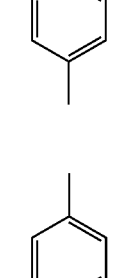 | 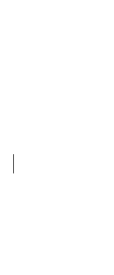 | 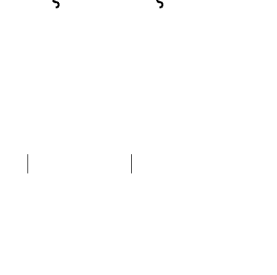 | 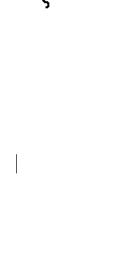 | 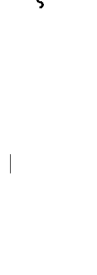 |
| 53 | — |  |  |  |  |  |
| 54 | — |  | 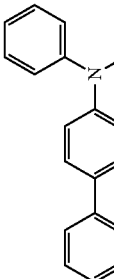 | 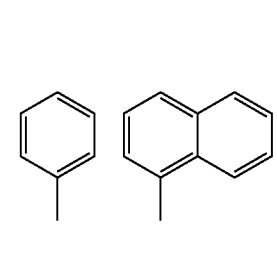 | 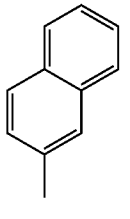 | 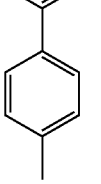 |

TABLE 1-continued
| | L1 | L2 | Ar1 | Ar2 | Ar3 | Ar4 |
|---|---|---|---|---|---|---|
| 55 | — |  |  | 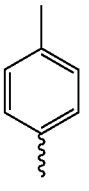 | 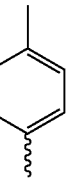 |  |
| 56 | — | 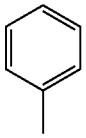 | 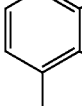 | 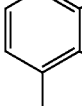 | 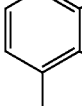 | 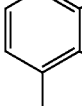 |
| 57 | — | 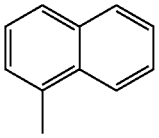 | 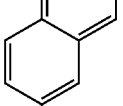 | 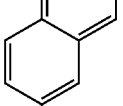 | 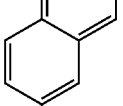 | 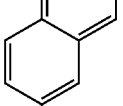 |
| 58 | — | 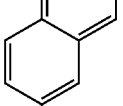 | 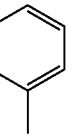 | 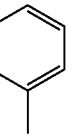 | 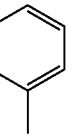 | 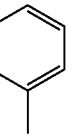 |
| 59 | — | 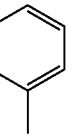 | 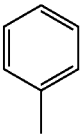 | 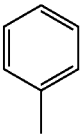 | 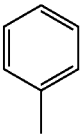 | 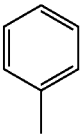 |
| 60 | — | 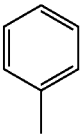 | 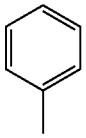 | 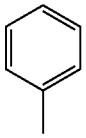 | 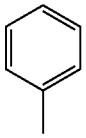 | 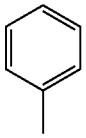 |

TABLE 1-continued
| | L1 | L2 | Ar1 | Ar2 | Ar3 | Ar4 |
|---|---|---|---|---|---|---|
| 61 | — | 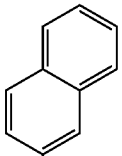 | 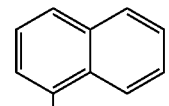 | 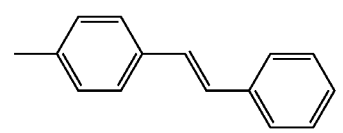 | 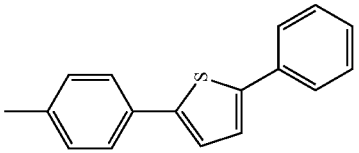 | 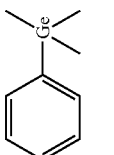 |
| 62 | — | | | | | |
| 63 | — | | | | | |
| 64 | — | | | | | |

TABLE 1-continued
| L1 | L2 | Ar1 | Ar2 | Ar3 | Ar4 |
|---|---|---|---|---|---|
| 65 | — | 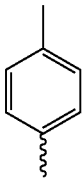 | 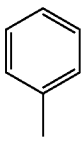 | 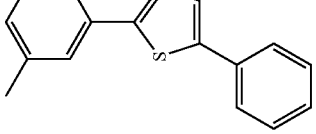 |  |  |
| 66 | — | 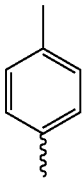 |  |  |  |  |

TABLE 1-continued

| | L1 | L2 | Ar1 | Ar2 | Ar3 | Ar4 |
|---|---|---|---|---|---|---|
| 67 | — | | | | | |
| 68 | — | | | | | |
| 69 | — | | | | | |
| 70 | — | | | | | |
| 71 | — | | | | | |

TABLE 1-continued
| | L1 | L2 | Ar1 | Ar2 | Ar3 | Ar4 |
|---|---|---|---|---|---|---|
| 72 | — | 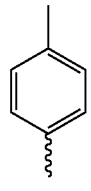 | 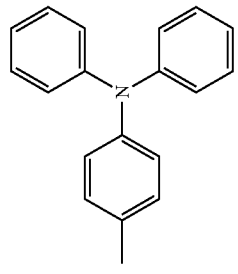 | 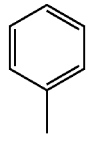 | 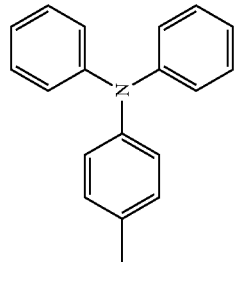 | 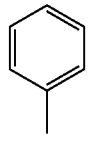 |
| 73 | — |  | 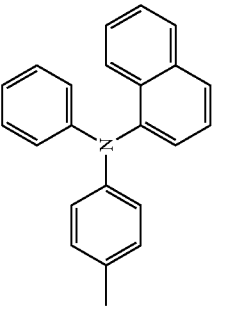 | 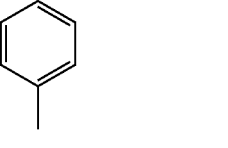 | 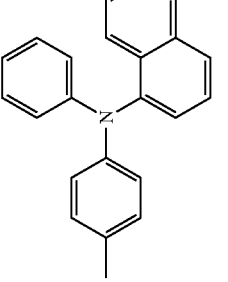 | 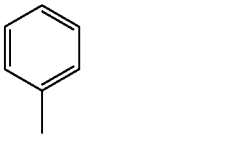 |
| 74 | — | 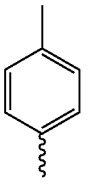 | 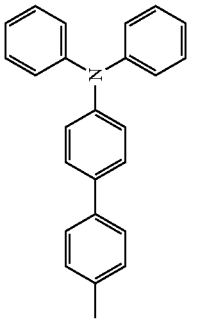 | 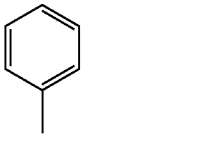 | 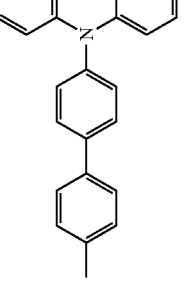 | 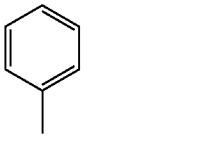 |
| 75 | — | 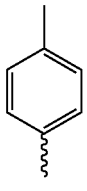 | 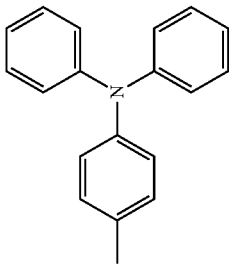 | 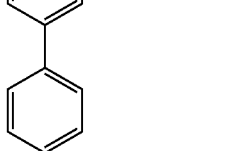 | 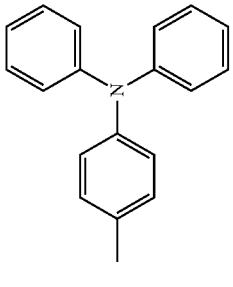 | 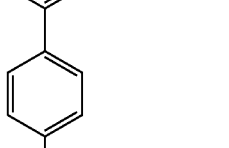 |

TABLE 1-continued

| | L1 | L2 | Ar1 | Ar2 | Ar3 | Ar4 |
|---|---|---|---|---|---|---|
| 76 | — | | | | | |
| 77 | — | | | | | |
| 78 | — | | | | | |
| 79 | — | | | | | |

TABLE 1-continued
| | L1 | L2 | Ar1 | Ar2 | Ar3 | Ar4 |
|---|---|---|---|---|---|---|
| 80 | — | 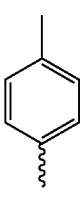 | 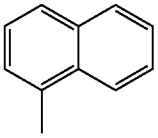 |  | 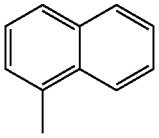 | 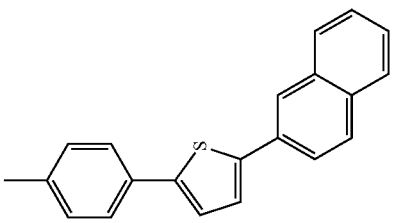 |
| 81 | — | 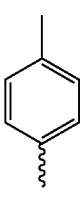 | 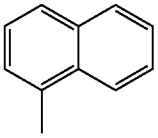 |  | 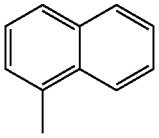 | 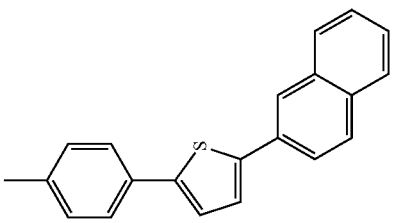 |

TABLE 1-continued
| | L1 | L2 | Ar1 | Ar2 | Ar3 | Ar4 |
|---|---|---|---|---|---|---|
| 82 | — | 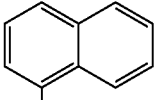 | 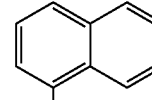 | 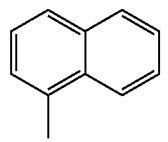 | 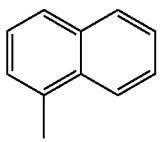 | 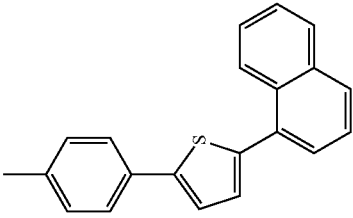 |
| 83 | — | 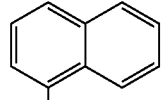 | 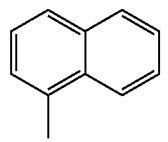 | 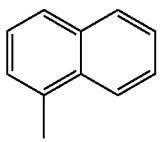 | 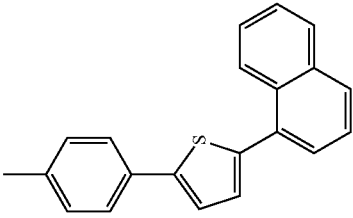 | 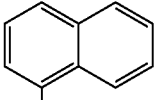 |
| 84 | — | 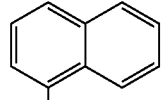 | 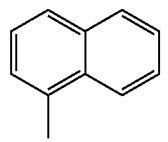 | 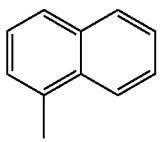 | 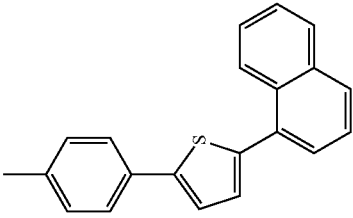 | 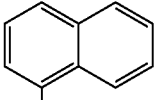 |
| 85 | — | 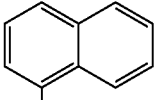 | | | | |

TABLE 1-continued

| | L1 | L2 | Ar1 | Ar2 | Ar3 | Ar4 |
|---|---|---|---|---|---|---|
| 86 | — | (p-phenylene) | 1-naphthyl | 2-anthryl | 1-naphthyl | 2-anthryl |
| 87 | — | (p-phenylene) | 1-naphthyl | N(phenyl)(p-tolyl) | 1-naphthyl | N(phenyl)(p-tolyl) |
| 88 | — | (p-phenylene) | 1-naphthyl | N(phenyl)(1-naphthyl)(p-tolyl) | 1-naphthyl | N(phenyl)(1-naphthyl)(p-tolyl) |
| 89 | — | (p-phenylene) | 1-naphthyl | N(phenyl)₂(biphenyl-p-tolyl) | 1-naphthyl | N(phenyl)₂(biphenyl-p-tolyl) |

TABLE 1-continued
| | L1 | L2 | Ar1 | Ar2 | Ar3 | Ar4 |
|---|---|---|---|---|---|---|
| 90 | — | 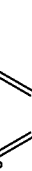 | 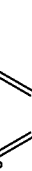 | 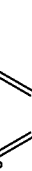 | 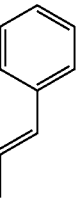 | 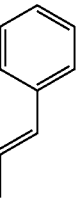 |
| 91 | — | 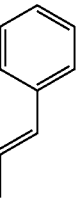 | 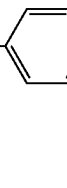 | 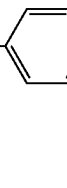 | 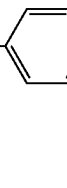 | 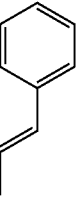 |

TABLE 1-continued
| | L1 | L2 | Ar1 | Ar2 | Ar3 | Ar4 |
|---|---|---|---|---|---|---|
| 92 | — |  |  |  |  |  |
| 93 | — |  |  |  |  |  |
| 94 | — |  |  |  |  |  |

TABLE 1-continued

| | L1 | L2 | Ar1 | Ar2 | Ar3 | Ar4 |
|---|---|---|---|---|---|---|
| 95 | — | (p-phenylene) | 2-naphthyl | 9-anthryl (Me) | 2-naphthyl | 9-anthryl (Me) |
| 96 | — | (p-phenylene) | 2-naphthyl | methylperylenyl | 2-naphthyl | methylperylenyl |
| 97 | — | (p-phenylene) | 2-naphthyl | 2-methyltetracenyl | 2-naphthyl | 2-methyltetracenyl |
| 98 | — | (p-phenylene) | 2-naphthyl | N,N-diphenyl-N-(p-tolyl)amino | 2-naphthyl | N,N-diphenyl-N-(p-tolyl)amino |
| 99 | — | (p-phenylene) | 2-naphthyl | N-(1-naphthyl)-N-(p-tolyl)-N-phenylamino | 2-naphthyl | N-(1-naphthyl)-N-(p-tolyl)-N-phenylamino |

TABLE 1-continued

| | L1 | L2 | Ar1 | Ar2 | Ar3 | Ar4 |
|---|---|---|---|---|---|---|
| 100 | — | | | | | |
| 101 | | | | | | |
| 102 | | | | | | |
| 103 | | | | | | |
| 104 | | | | | | |
| 105 | | | | | | |
| 106 | | | | | | |

TABLE 1-continued

TABLE 1-continued
| | L1 | L2 | Ar1 | Ar2 | Ar3 | Ar4 |
|---|---|---|---|---|---|---|
| 114 |  | 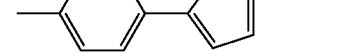 |  |  | 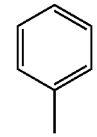 | 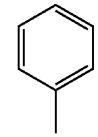 |
| 115 | 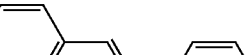 |  | 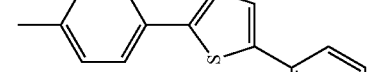 |  | 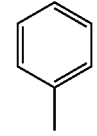 | 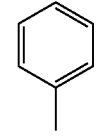 |
| 116 |  | 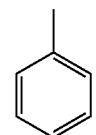 | 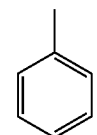 |  | 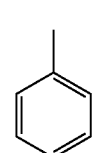 | 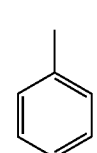 |

TABLE 1-continued

| | L1 | L2 | Ar1 | Ar2 | Ar3 | Ar4 |
|---|---|---|---|---|---|---|
| 117 | p-phenylene | p-phenylene | phenyl | 5-(2-naphthyl)-2-(4-methylphenyl)thiophene | phenyl | 5-(2-naphthyl)-2-(4-methylphenyl)thiophene |
| 118 | p-phenylene | p-phenylene | phenyl | 5-(1-naphthyl)-2-(4-methylphenyl)thiophene | phenyl | 5-(1-naphthyl)-2-(4-methylphenyl)thiophene |
| 119 | p-phenylene | p-phenylene | phenyl | 1-pyrenyl | phenyl | 1-pyrenyl |

TABLE 1-continued

| | L1 | L2 | Ar1 | Ar2 | Ar3 | Ar4 |
|---|---|---|---|---|---|---|
| 120 | | | | | | |
| 121 | | | | | | |
| 122 | | | | | | |
| 123 | | | | | | |
| 124 | | | | | | |

TABLE 1-continued

| | L1 | L2 | Ar1 | Ar2 | Ar3 | Ar4 |
|---|---|---|---|---|---|---|
| 125 | | | | | | |
| 126 | | | | | | |
| 127 | | | | | | |
| 128 | | | | | | |
| 129 | | | | | | |

TABLE 1-continued

| | L1 | L2 | Ar1 | Ar2 | Ar3 | Ar4 |
|---|---|---|---|---|---|---|
| 130 | p-phenylene | p-phenylene | 1-naphthyl | 4-styrylphenyl | 1-naphthyl | 4-styrylphenyl |
| 131 | p-phenylene | p-phenylene | 1-naphthyl | 5-phenylthiophen-2-yl-phenyl | 1-naphthyl | 5-phenylthiophen-2-yl-phenyl |

TABLE 1-continued

| | L1 | L2 | Ar1 | Ar2 | Ar3 | Ar4 |
|---|---|---|---|---|---|---|
| 132 | phenyl | phenyl | 1-naphthyl | 5-(2-naphthyl)-2-(4-methylphenyl)thiophene | 1-naphthyl | 5-(2-naphthyl)-2-(4-methylphenyl)thiophene |
| 133 | phenyl | phenyl | 1-naphthyl | 5-(1-naphthyl)-2-(4-methylphenyl)thiophene | 1-naphthyl | 5-(1-naphthyl)-2-(4-methylphenyl)thiophene |
| 134 | phenyl | phenyl | 1-naphthyl | 1-pyrenyl | 1-naphthyl | 1-pyrenyl |

TABLE 1-continued

TABLE 1-continued

| | L1 | L2 | Ar1 | Ar2 | Ar3 | Ar4 |
|---|---|---|---|---|---|---|
| 139 | | | | | | |
| 140 | | | | | | |
| 141 | | | | | | |

TABLE 1-continued

| | L1 | L2 | Ar1 | Ar2 | Ar3 | Ar4 |
|---|---|---|---|---|---|---|
| 142 | phenyl | phenyl | 2-naphthyl | 4-(5-phenylthiophen-2-yl)phenyl | 2-naphthyl | 4-(5-phenylthiophen-2-yl)phenyl |
| 143 | phenyl | phenyl | 2-naphthyl | 4-(5-(naphthalen-2-yl)thiophen-2-yl)phenyl | 2-naphthyl | 4-(5-(naphthalen-2-yl)thiophen-2-yl)phenyl |

TABLE 1-continued

| | L1 | L2 | Ar1 | Ar2 | Ar3 | Ar4 |
|---|---|---|---|---|---|---|
| 144 | phenyl | phenyl | 2-naphthyl | 4-(5-(2-naphthyl)thiophen-2-yl)phenyl | 2-naphthyl | 4-(5-(2-naphthyl)thiophen-2-yl)phenyl |
| 145 | phenyl | phenyl | 2-naphthyl | pyrenyl | 2-naphthyl | pyrenyl |
| 146 | phenyl | phenyl | 2-naphthyl | 9-methylanthracenyl | 2-naphthyl | 9-methylanthracenyl |
| 147 | phenyl | phenyl | 2-naphthyl | perylenyl | 2-naphthyl | perylenyl |

TABLE 1-continued

TABLE 1-continued

TABLE 1-continued

TABLE 1-continued
| | L1 | L2 | Ar1 | Ar2 | Ar3 | Ar4 |
|---|---|---|---|---|---|---|
| 165 | 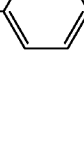 |  | 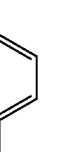 | 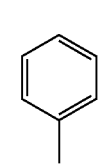 |  |  |
| 166 | 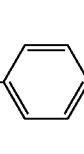 | 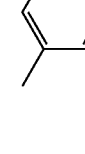 |  | 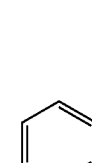 |  |  |

TABLE 1-continued
| | L1 | L2 | Ar1 | Ar2 | Ar3 | Ar4 |
|---|---|---|---|---|---|---|
| 167 | 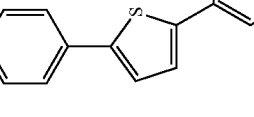 | 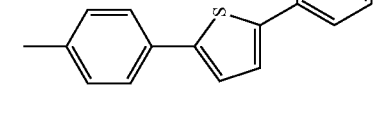 | 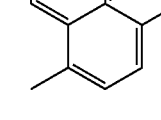 |  |  |  |
| 168 |  |  | 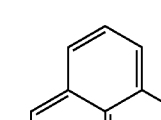 |  |  |  |
| 169 |  |  |  |  |  |  |

TABLE 1-continued
| | L1 | L2 | Ar1 | Ar2 | Ar3 | Ar4 |
|---|---|---|---|---|---|---|
| 170 |  | 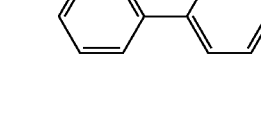 | 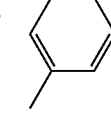 | 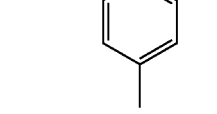 | 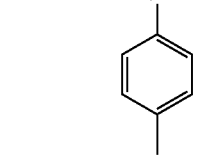 | 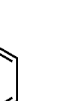 |
| 171 | 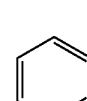 |  |  | 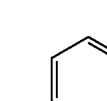 |  |  |
| 172 |  |  |  |  |  | 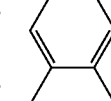 |
| 173 |  | 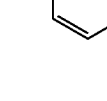 |  |  |  |  |
| 174 |  |  |  | 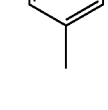 | 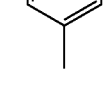 | 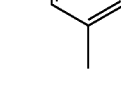 |

TABLE 1-continued
| | L1 | L2 | Ar1 | Ar2 | Ar3 | Ar4 |
|---|---|---|---|---|---|---|
| 175 | 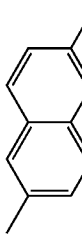 | 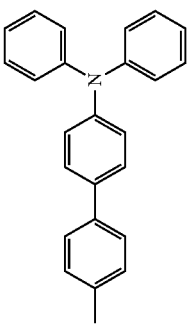 | 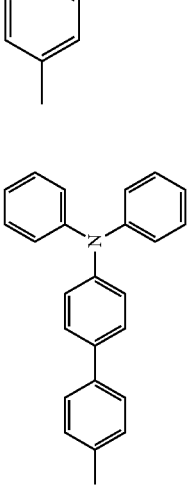 | 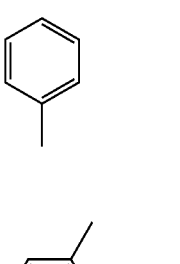 | 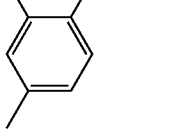 | 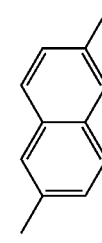 |
| 176 | 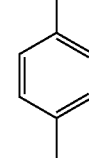 | 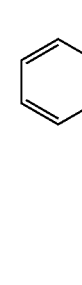 | 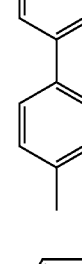 | 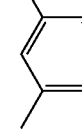 | 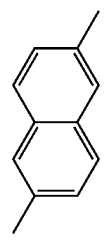 | 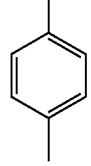 |
| 177 | 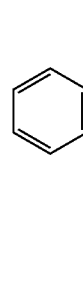 | 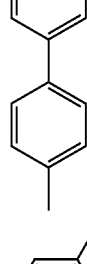 | 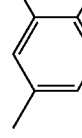 | 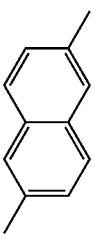 | 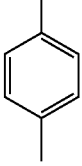 | 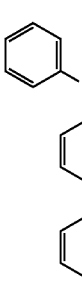 |
| 178 | 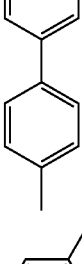 | 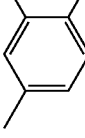 | 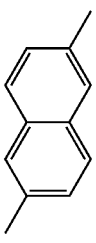 |  | 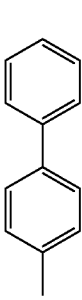 | 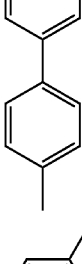 |
| 179 | 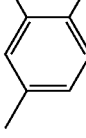 | | | | | |

TABLE 1-continued
| | L1 | L2 | Ar1 | Ar2 | Ar3 | Ar4 |
|---|---|---|---|---|---|---|
| 180 |  |  |  |  | 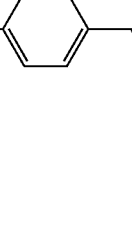 | 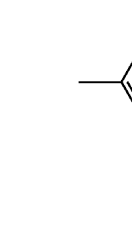 |
| 181 | 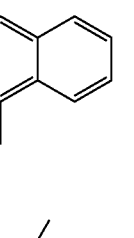 | 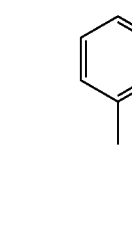 | 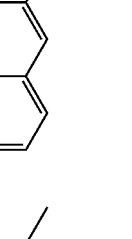 | 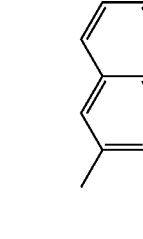 | 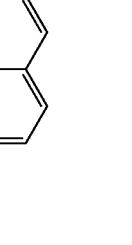 | 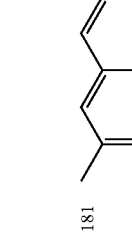 |

TABLE 1-continued
| | L1 | L2 | Ar1 | Ar2 | Ar3 | Ar4 |
|---|---|---|---|---|---|---|
| 182 | 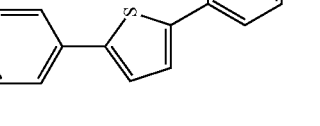 | 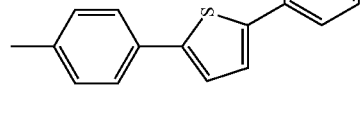 | 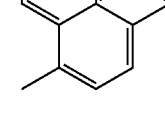 | 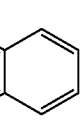 | 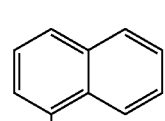 | 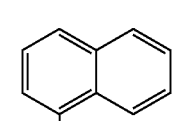 |
| 183 | 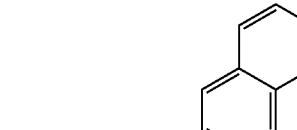 |  | 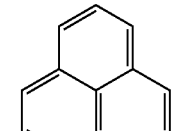 | 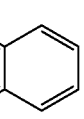 | 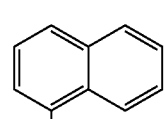 | 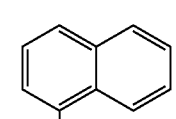 |
| 184 |  | 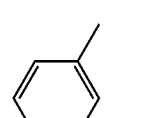 | 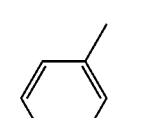 |  | 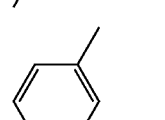 | 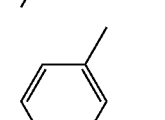 |

TABLE 1-continued
| | L1 | L2 | Ar1 | Ar2 | Ar3 | Ar4 |
|---|---|---|---|---|---|---|
| 185 | 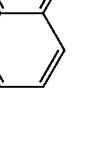 | 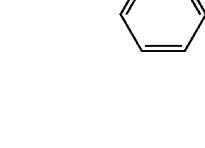 | 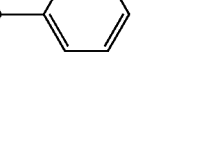 | 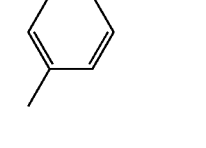 | 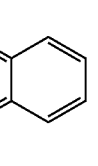 | 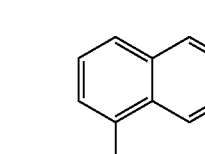 |
| 186 | 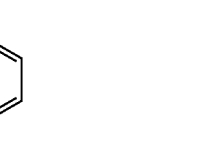 | 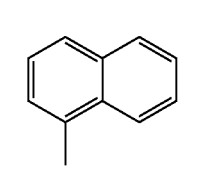 | 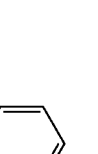 | 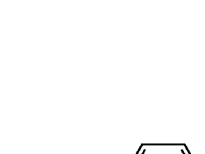 | 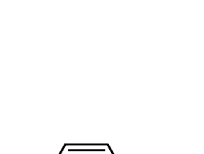 | 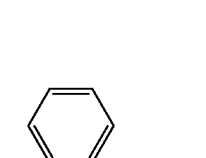 |
| 187 | 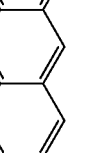 | 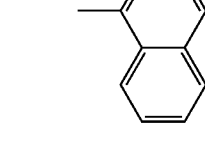 | 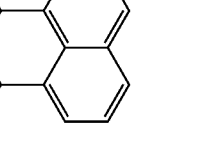 | 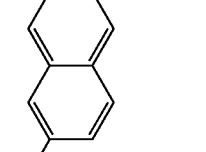 | 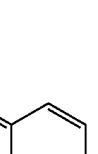 | 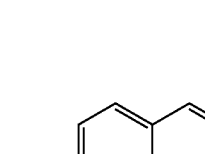 |
| 188 |  | 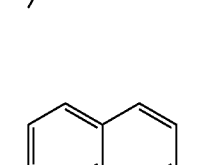 |  | 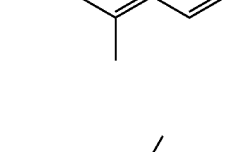 |  | 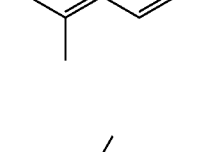 |

TABLE 1-continued
| | L1 | L2 | Ar1 | Ar2 | Ar3 | Ar4 |
|---|---|---|---|---|---|---|
| 189 | 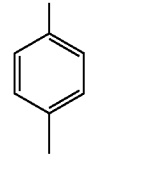 | 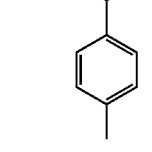 |  | 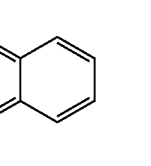 | 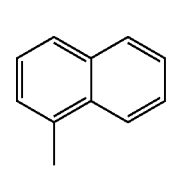 | 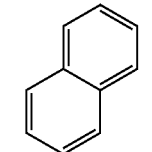 |
| 190 | 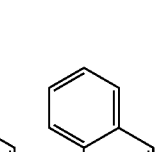 | 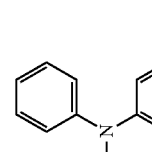 | 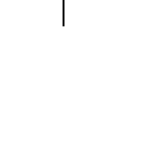 | 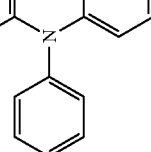 | 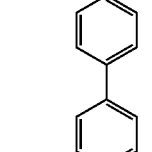 | 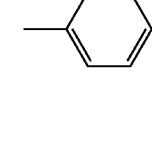 |
| 191 | 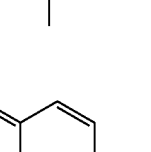 | 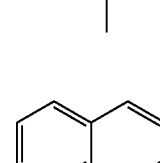 | 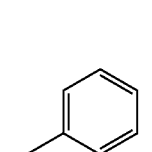 | 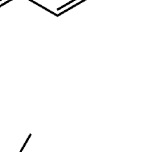 | 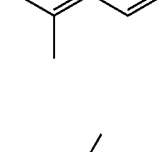 | 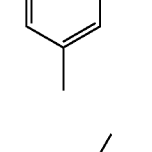 |

TABLE 1-continued
| | L1 | L2 | Ar1 | Ar2 | Ar3 | Ar4 |
|---|---|---|---|---|---|---|
| 192 | 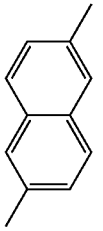 | 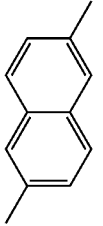 | 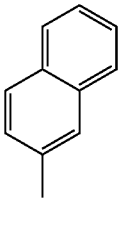 | 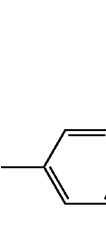 | 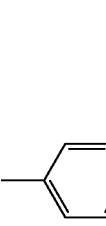 | 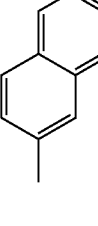 |
| 193 | 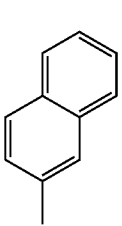 | 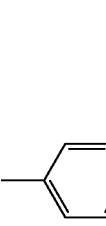 | 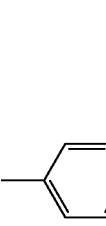 | 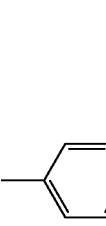 | | |

TABLE 1-continued
| | L1 | L2 | Ar1 | Ar2 | Ar3 | Ar4 |
|---|---|---|---|---|---|---|
| 194 |  | 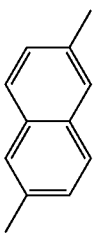 | 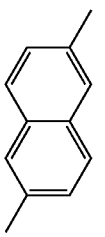 |  |  | 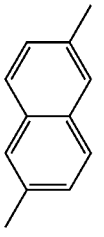 |
| 195 | 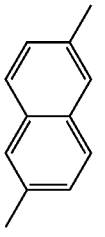 |  | 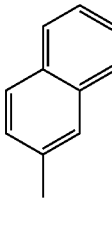 | 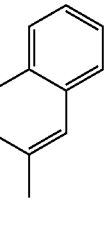 | 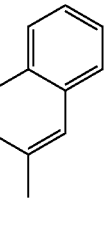 | 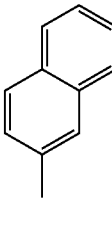 |
| 196 | 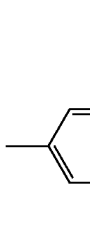 | 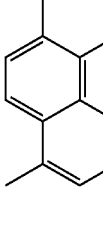 | 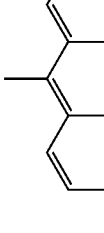 | 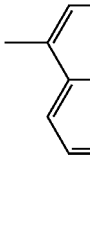 | 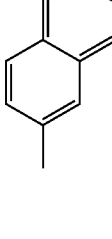 | 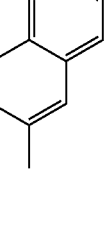 |
| 197 | 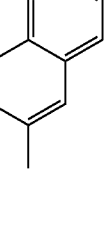 | 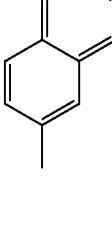 | 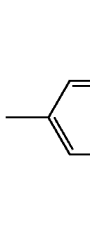 | 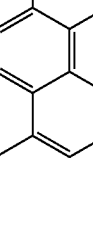 | 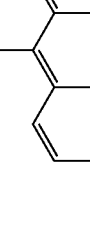 | 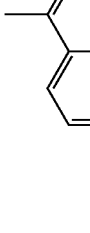 |

TABLE 1-continued

TABLE 1-continued

| | L1 | L2 | Ar1 | Ar2 | Ar3 | Ar4 |
|---|---|---|---|---|---|---|
| 203 | | | | | | |
| 204 | | | | | | |
| 205 | | | | | | |
| 206 | | | | | | |
| 207 | | | | | | |

TABLE 1-continued

| | L1 | L2 | Ar1 | Ar2 | Ar3 | Ar4 |
|---|---|---|---|---|---|---|
| 208 | | | | | | |
| 209 | | | | | | |
| 210 | | | | | | |
| 211 | | | | | | |
| 212 | | | | | | |

TABLE 1-continued

| | L1 | L2 | Ar1 | Ar2 | Ar3 | Ar4 |
|---|---|---|---|---|---|---|
| 213 | | | | | | |
| 214 | | | | | | |
| 215 | | | | | | |

TABLE 1-continued
| | L1 | L2 | Ar1 | Ar2 | Ar3 | Ar4 |
|---|---|---|---|---|---|---|
| 216 | 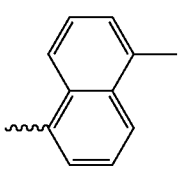 | 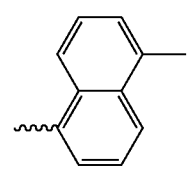 | 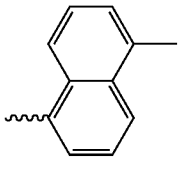 | 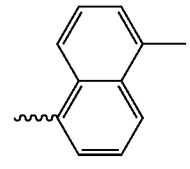 | 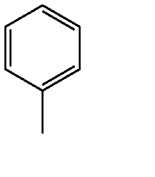 | 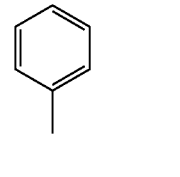 |
| 217 | 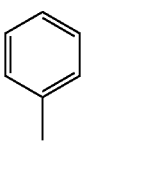 | 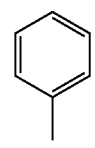 | 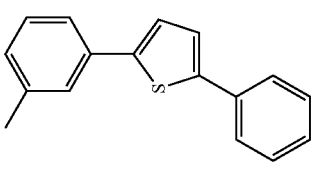 | 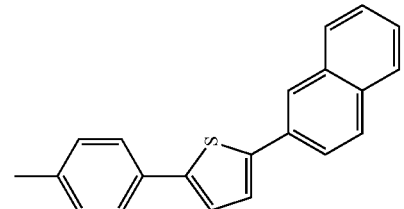 | 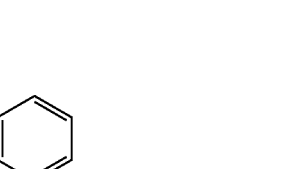 | 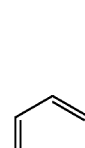 |

TABLE 1-continued
| | L1 | L2 | Ar1 | Ar2 | Ar3 | Ar4 |
|---|---|---|---|---|---|---|
| 218 | 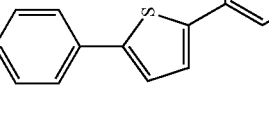 | 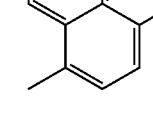 | 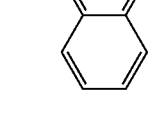 | 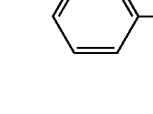 |  | 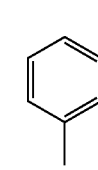 |
| 219 | 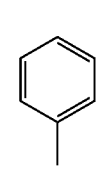 | 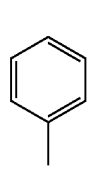 | 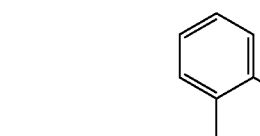 | 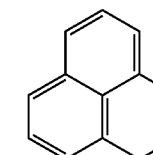 | 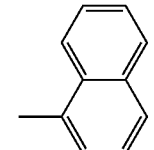 | 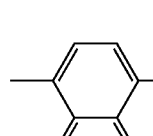 |
| 220 |  | 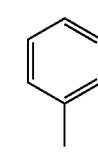 | 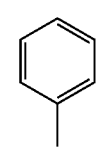 | 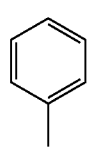 | 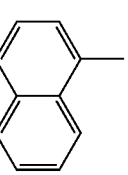 | 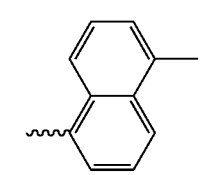 |
| 221 | 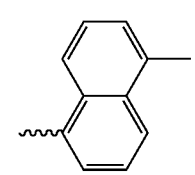 | 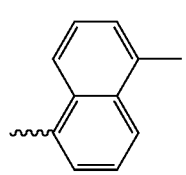 | 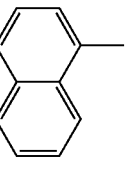 | 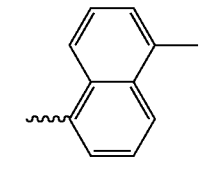 | 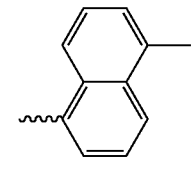 | 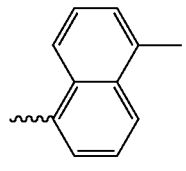 |

TABLE 1-continued

| | L1 | L2 | Ar1 | Ar2 | Ar3 | Ar4 |
|---|---|---|---|---|---|---|
| 222 | | | | | | |
| 223 | | | | | | |
| 224 | | | | | | |
| 225 | | | | | | |

TABLE 1-continued

TABLE 1-continued
| | L1 | L2 | Ar1 | Ar2 | Ar3 | Ar4 |
|---|---|---|---|---|---|---|
| 230 | 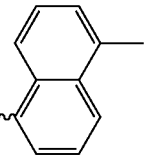 | 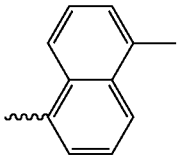 | 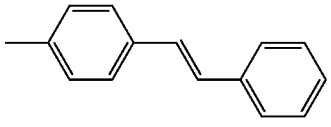 | 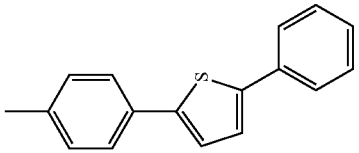 | 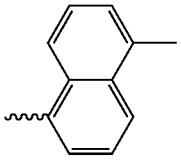 | 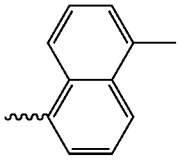 |
| 231 | 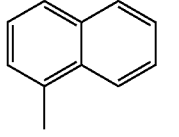 | 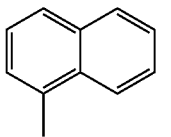 | 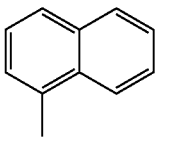 | 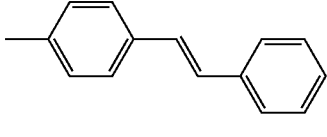 | 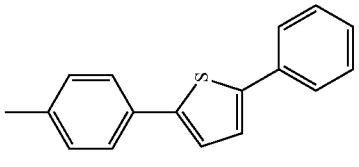 | 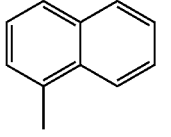 |

| | L1 | L2 | Ar1 | Ar2 | Ar3 | Ar4 |
|---|---|---|---|---|---|---|
| 232 | 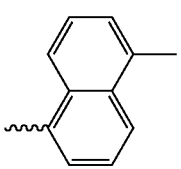 | 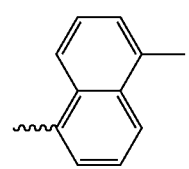 | 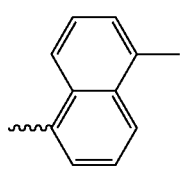 | 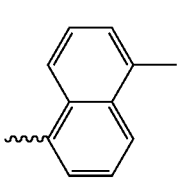 | 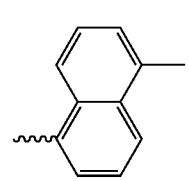 | 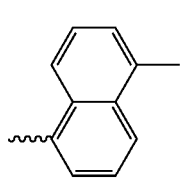 |
| 233 | 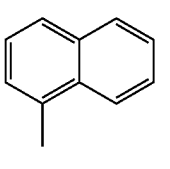 | 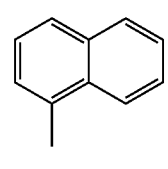 | 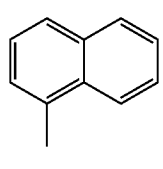 | 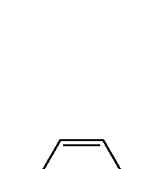 | 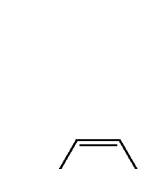 | 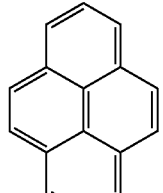 |
| 234 | 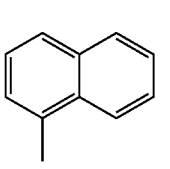 | 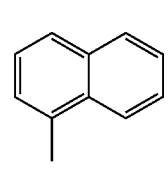 | 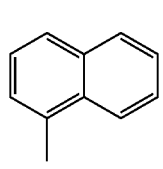 | 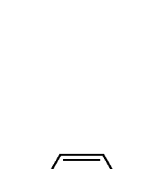 | 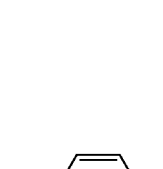 | 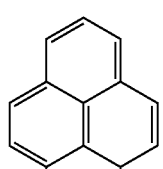 |

TABLE 1-continued

TABLE 1-continued

| | L1 | L2 | Ar1 | Ar2 | Ar3 | Ar4 |
|---|---|---|---|---|---|---|
| 239 | | | | | | |
| 240 | | | | | | |
| 241 | | | | | | |

TABLE 1-continued
| | L1 | L2 | Ar1 | Ar2 | Ar3 | Ar4 |
|---|---|---|---|---|---|---|
| 242 | 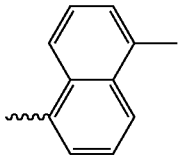 | 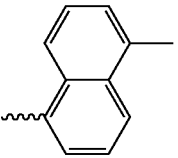 | 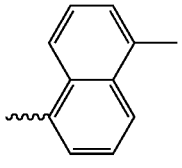 | 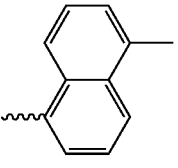 | 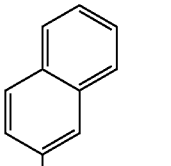 | 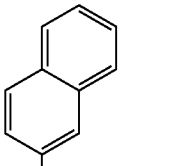 |
| 243 | 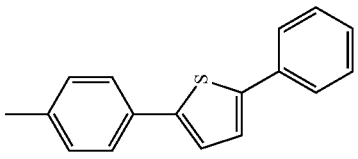 | 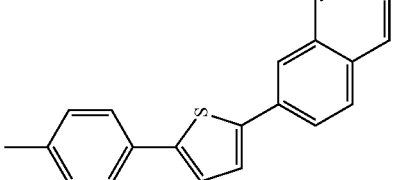 | 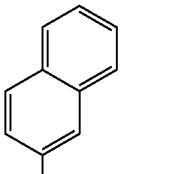 | 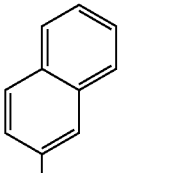 | 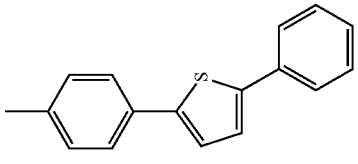 | 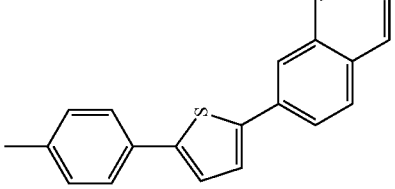 |

TABLE 1-continued
| | L1 | L2 | Ar1 | Ar2 | Ar3 | Ar4 |
|---|---|---|---|---|---|---|
| 244 | 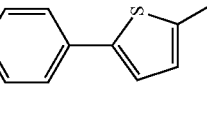 | 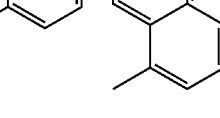 | 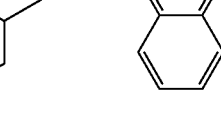 | 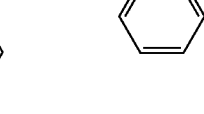 | 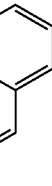 | 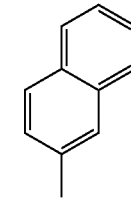 |
| 245 | 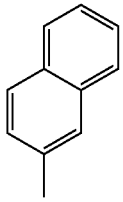 | 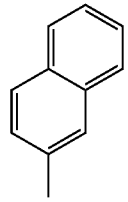 | 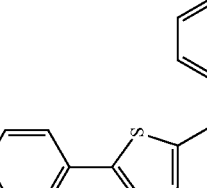 | 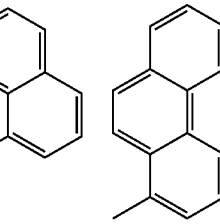 | 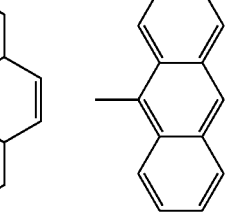 | 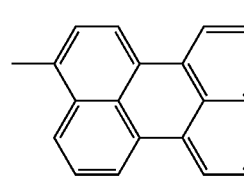 |
| 246 | 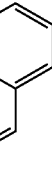 | 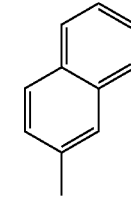 | 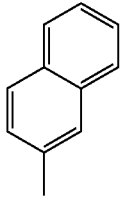 | 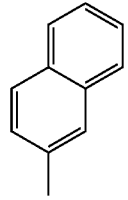 | 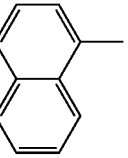 | 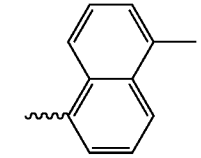 |
| 247 | 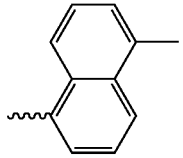 | 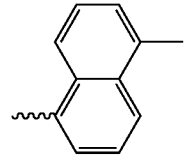 | 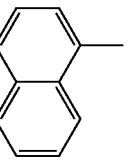 | 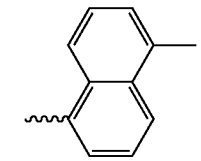 | 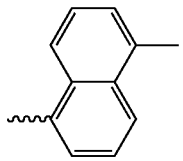 | 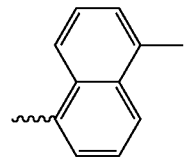 |

TABLE 1-continued

| | L1 | L2 | Ar1 | Ar2 | Ar3 | Ar4 |
|---|---|---|---|---|---|---|
| 248 | | | | | | |
| 249 | | | | | | |
| 250 | | | | | | |
| 251 | | | | | | |
| 252 | | | | | | |

TABLE 1-continued
| | L1 | L2 | Ar1 | Ar2 | Ar3 | Ar4 |
|---|---|---|---|---|---|---|
| 253 | 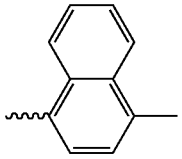 | 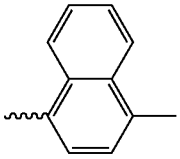 | 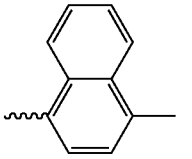 | 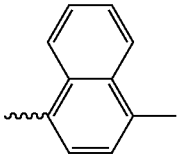 | 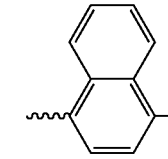 |  |
| 254 | 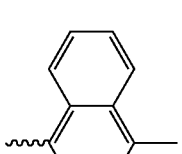 | 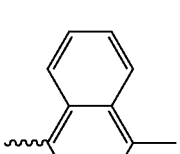 | 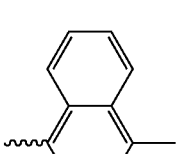 | 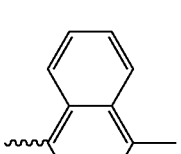 | 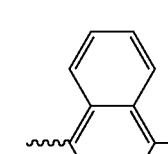 |  |
| 255 | 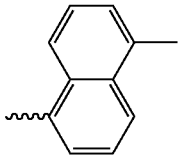 | 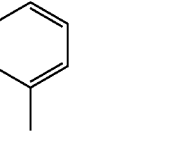 | 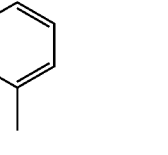 | 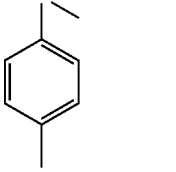 | 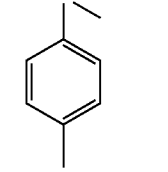 |  |
| 256 | 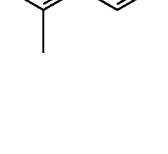 | 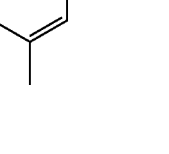 | 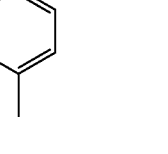 | 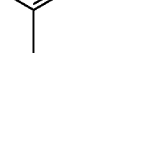 | 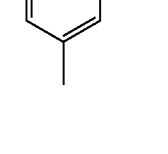 |  |
| 257 | 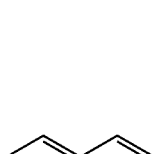 | 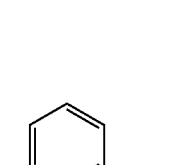 | 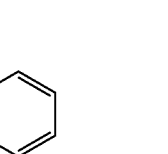 | 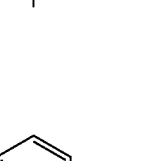 | 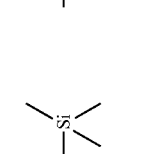 |  |

TABLE 1-continued

TABLE 1-continued

| | L1 | L2 | Ar1 | Ar2 | Ar3 | Ar4 |
|---|---|---|---|---|---|---|
| 263 | 4-methylnaphthyl | 4-methylnaphthyl | (4-methylphenyl)trimethylgermane | 1-methylnaphthyl | (4-methylphenyl)trimethylgermane | 1-methylnaphthyl |
| 264 | 4-methylnaphthyl | 4-methylnaphthyl | 4-methylstyryl-phenyl | 4-methylstilbene | phenyl | 4-methylstilbene |
| 265 | 4-methylnaphthyl | 4-methylnaphthyl | phenyl | 4-methylphenyl-5-phenylthiophene | phenyl | 4-methylphenyl-5-phenylthiophene |

TABLE 1-continued

| | L1 | L2 | Ar1 | Ar2 | Ar3 | Ar4 |
|---|---|---|---|---|---|---|
| 266 | naphthalen-1,4-diyl | naphthalen-1,4-diyl | tolyl | 2-(3-methylphenyl)-5-phenylthiophene | tolyl | 2-(3-methylphenyl)-5-phenylthiophene |
| 267 | naphthalen-1,4-diyl | naphthalen-1,4-diyl | tolyl | 2-(4-methylphenyl)-5-(naphthalen-2-yl)thiophene | tolyl | 2-(4-methylphenyl)-5-(naphthalen-2-yl)thiophene |

TABLE 1-continued
| | L1 | L2 | Ar1 | Ar2 | Ar3 | Ar4 |
|---|---|---|---|---|---|---|
| 268 | 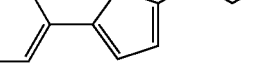 | 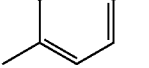 | 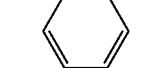 | 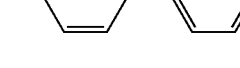 | 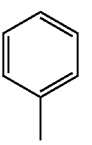 | 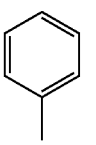 |
| 269 | 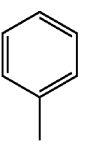 |  | 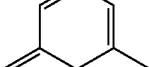 | 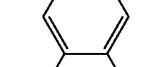 | 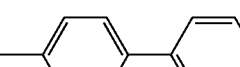 | 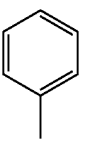 |
| 270 | 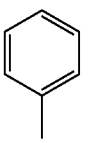 | 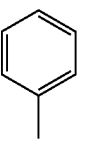 |  | 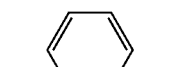 | 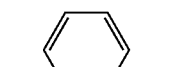 | 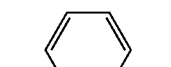 |
| 271 |  | 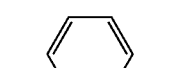 | 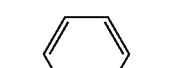 | 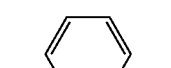 | | |

TABLE 1-continued
| | L1 | L2 | Ar1 | Ar2 | Ar3 | Ar4 |
|---|---|---|---|---|---|---|
| 272 | 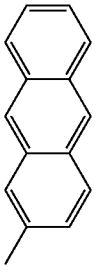 | 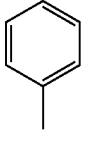 | 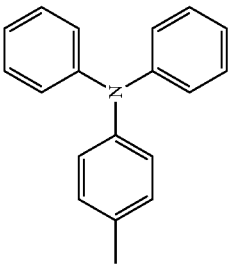 | 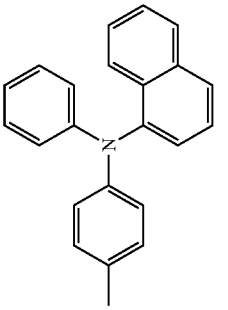 | 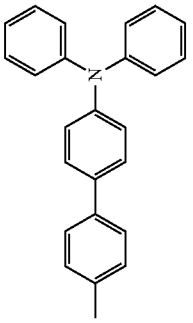 | 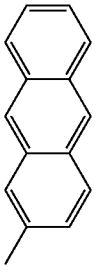 |
| 273 | 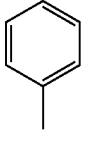 | 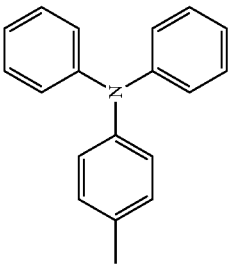 | 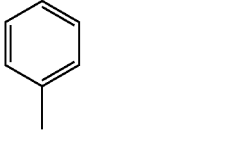 | 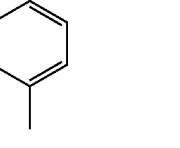 | 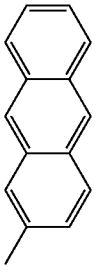 | 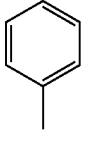 |
| 274 | 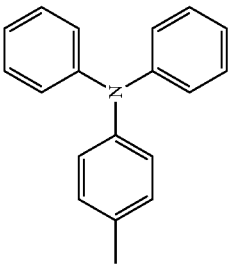 | 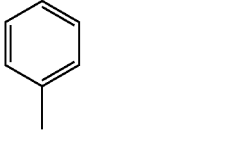 | 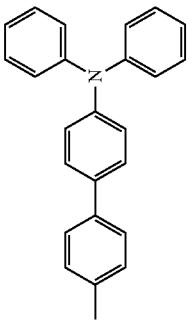 | 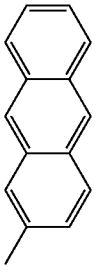 | 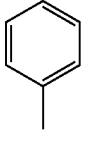 | 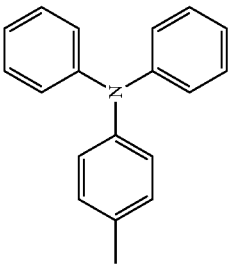 |
| 275 | 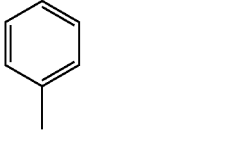 | 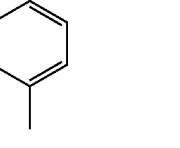 | | | | |

TABLE 1-continued

| | L1 | L2 | Ar1 | Ar2 | Ar3 | Ar4 |
|---|---|---|---|---|---|---|
| 276 | | | | | | |
| 277 | | | | | | |
| 278 | | | | | | |
| 279 | | | | | | |

TABLE 1-continued
| | L1 | L2 | Ar1 | Ar2 | Ar3 | Ar4 |
|---|---|---|---|---|---|---|
| 280 | 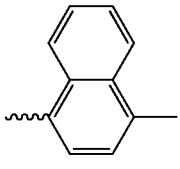 | 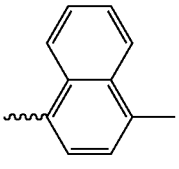 | 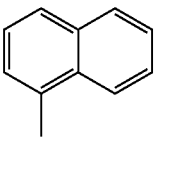 | 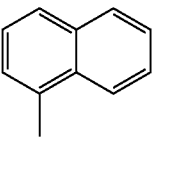 | 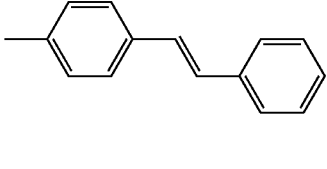 | 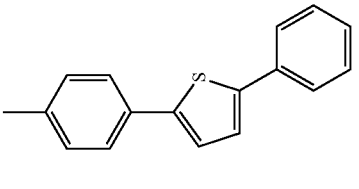 |
| 281 | 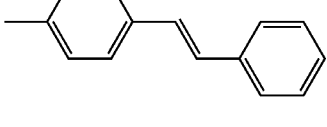 | 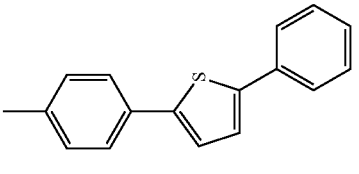 | | | | |

TABLE 1-continued
| | L1 | L2 | Ar1 | Ar2 | Ar3 | Ar4 |
|---|---|---|---|---|---|---|
| 282 | 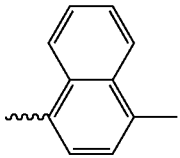 | 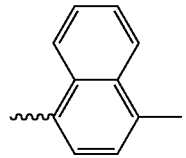 | 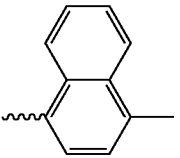 | 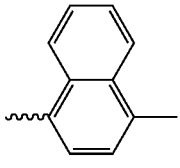 | 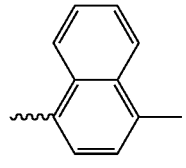 | 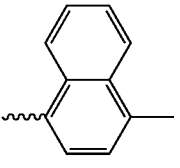 |
| 283 | 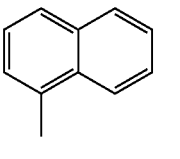 | 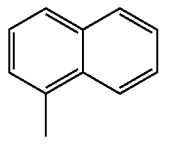 | 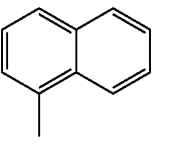 | 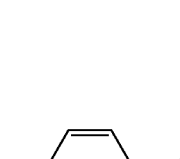 | 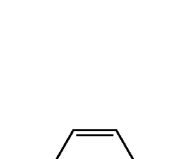 | 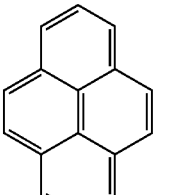 |
| 284 | 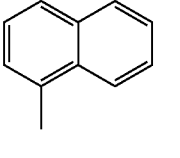 | 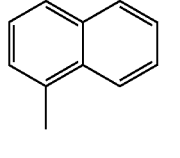 | 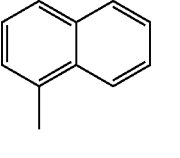 | 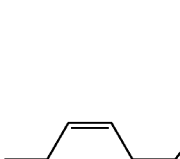 | 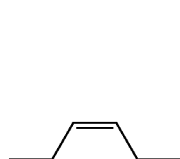 | 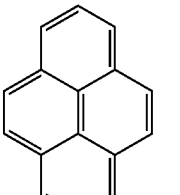 |

TABLE 1-continued
| | L1 | L2 | Ar1 | Ar2 | Ar3 | Ar4 |
|---|---|---|---|---|---|---|
| 285 |  | 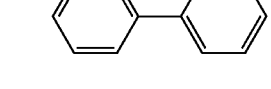 |  | 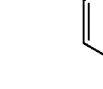 |  | 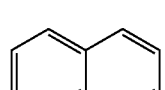 |
| 286 |  | 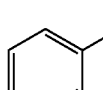 |  |  |  |  |
| 287 |  | 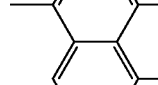 |  |  |  |  |
| 288 |  |  |  | 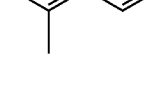 |  | 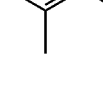 |

TABLE 1-continued
| | L1 | L2 | Ar1 | Ar2 | Ar3 | Ar4 |
|---|---|---|---|---|---|---|
| 289 | 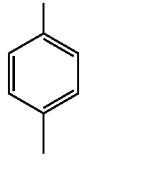 | 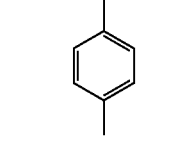 |  | 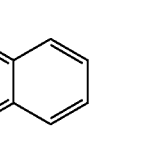 | 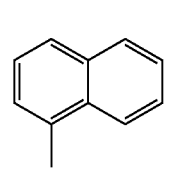 | 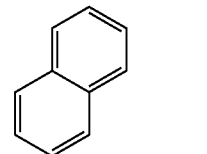 |
| 290 | 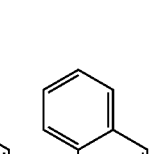 | 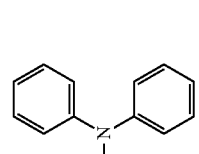 |  | 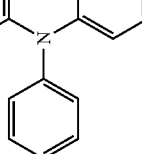 | 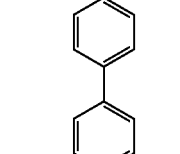 | 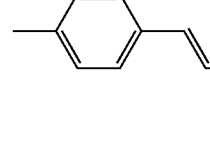 |
| 291 | 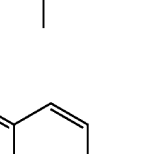 | 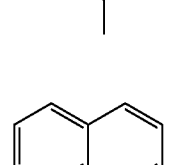 | 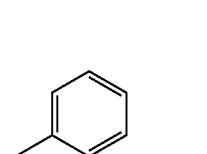 |  | 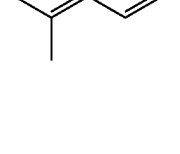 | 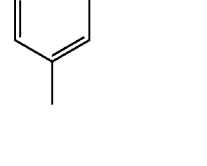 |

TABLE 1-continued

| | L1 | L2 | Ar1 | Ar2 | Ar3 | Ar4 |
|---|---|---|---|---|---|---|
| 292 | naphthyl | naphthyl | methylnaphthyl | methylphenyl-thiophene-phenyl | methylnaphthyl | methylphenyl-thiophene-phenyl |
| 293 | naphthyl | naphthyl | methylnaphthyl | methylphenyl-thiophene-naphthyl | methylnaphthyl | methylphenyl-thiophene-naphthyl |

TABLE 1-continued
| | L1 | L2 | Ar1 | Ar2 | Ar3 | Ar4 |
|---|---|---|---|---|---|---|
| 294 | 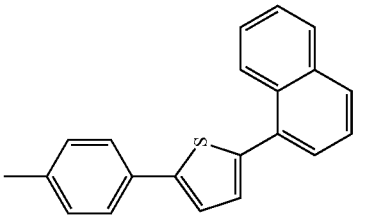 | 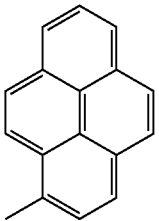 | 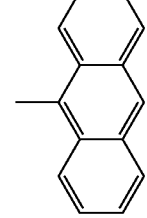 | 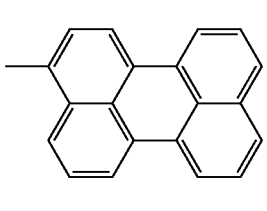 | 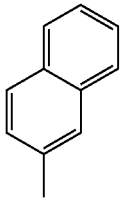 | 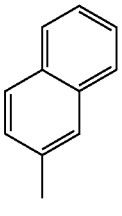 |
| 295 | 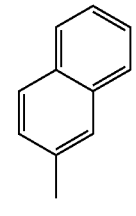 | 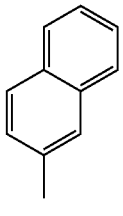 | 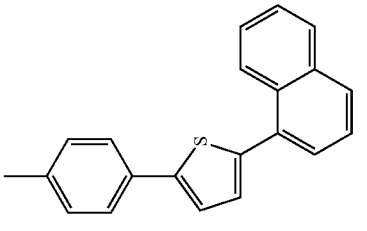 | 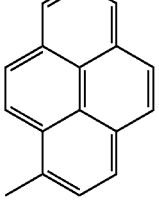 | 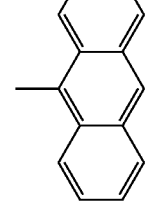 | 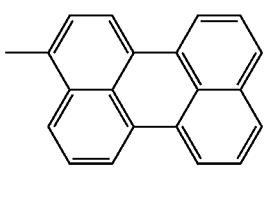 |
| 296 | 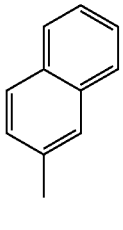 | 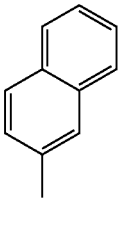 | 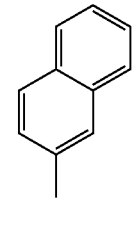 | 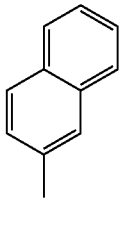 | 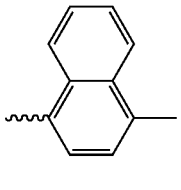 | 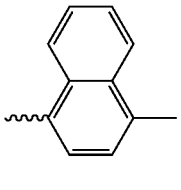 |
| 297 | 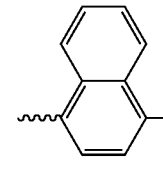 | 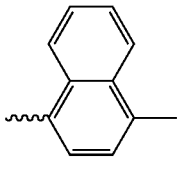 | 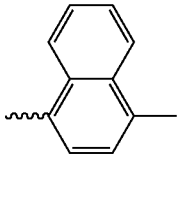 | 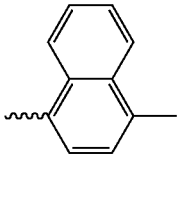 | 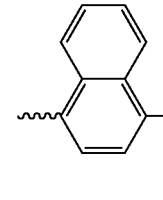 | 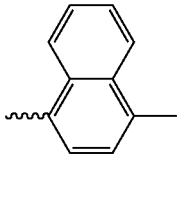 |

TABLE 1-continued
| | L1 | L2 | Ar1 | Ar2 | Ar3 | Ar4 |
|---|---|---|---|---|---|---|
| 298 | 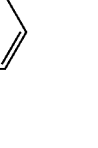 |  | 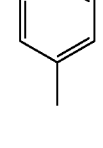 |  | 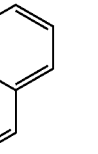 | 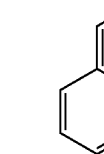 |
| 299 | 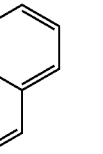 |  |  | 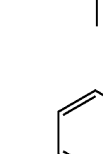 | 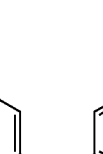 | 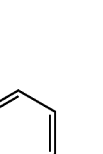 |
| 300 | 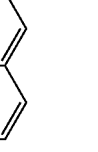 |  | 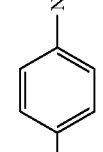 |  | 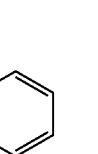 |  |
| 301 | 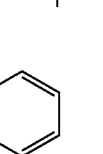 |  |  | 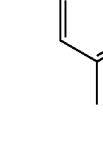 |  |  |

Further, the present invention provides a method for preparing the diamine derivative represented by Formula 1.

The diamine derivative according to the present invention can be prepared by reacting a dibromoaryl compound with an arylamine compound in the presence of a palladium catalyst. A specific preparation method will be described in the following Preparation Examples.

Further, the present invention provides an organic electronic device comprising the diamine derivative represented by Formula 1.

The diamine derivative according to the present invention can serve as a hole injecting, hole transporting, electron injecting, electron transporting, or light emitting material in an organic electronic device including an organic light emitting device. Particularly, it can serve as a light emitting dopant as used alone, in particular, a blue light emitting dopant. The organic electronic device according to the present invention exhibits excellent characteristics in terms of efficiency, drive voltage, life time, and stability.

The organic electronic device of the present invention can be prepared by usual methods and materials for preparing an organic electronic device, except that the above-described compounds are used to form at least one organic material layer.

Hereinbelow, the organic light emitting device will be exemplified.

The above-described compounds can serve as a hole injecting, hole transporting, electron injecting, electron transporting, or light emitting material, and particularly serve as a light emitting material as used alone, as well as a light emitting host with an appropriate light emitting dopant or a light emitting dopant with an appropriate light emitting host.

In one embodiment of the present invention, the organic light emitting device may have a structure that comprises a first electrode, a second electrode and organic material layers interposed therebetween, and can be prepared by usual methods and materials for preparing an organic light emitting device, except that the above-described compound according to the present invention is used to form at least one of the organic material layers in an organic light emitting device. The structure of the organic light emitting device according to the present invention is shown in FIG. 1.

For example, the organic light emitting device according to the present invention can be prepared by depositing a metal, a metal oxide having conductivity or an alloy thereof on a substrate using a PVD (physical vapor deposition) process such as sputtering and e-beam evaporation to form an anode; forming an organic material layer comprising a hole injecting layer, a hole transporting layer, a light emitting layer, and an electron transporting layer on the anode; and depositing a material, which can be used as a cathode, thereon. Alternatively, the organic light emitting device can be prepared by sequentially depositing a cathode material, an organic material layer, and an anode material on a substrate.

The organic material layer may be of a multilayer structure containing a hole injecting layer, a hole transporting layer, a light emitting layer, an electron transporting layer, and the like, but not limited thereto, and may be of a monolayer structure. Further, the organic material layer can be produced to have a fewer number of layers, by using a variety of polymeric materials, by means of a solvent process rather than a deposit process, such as spin coating, dip coating, doctor blading, screen printing, ink jet printing, and heat transfer processes.

The anode material is preferably a material having a large work function to facilitate hole injection usually to an organic material layer. Specific examples of the anode material which can be used in the present invention include metals such as vanadium, chromium, copper, zinc and gold, or an alloy thereof; metal oxides such as zinc oxide, indium oxide, indium-tin oxide (ITO), and indium zinc oxide (IZO); a combination of a metal and an oxide such as ZnO:Al and $SnO_2$:Sb; conductive polymers such as poly(3-methylthiophene), poly[3,4-(ethylene-1,2-dioxy)thiophene] (PEDT), polypyrrole and polyaniline, but not limited thereto.

The cathode material is preferably a material having a small work function to facilitate electron injection usually to an organic material layer. Specific examples of the cathode material include metals such as magnesium, calcium, sodium, potassium, titanium, indium, yttrium, lithium, gadolinium, aluminum, silver, tin and lead, or an alloy thereof; multilayer structure materials such as LiF/Al and $LiO_2$/Al, but not limited thereto.

The hole injecting material is a material facilitating hole injection from an anode at low voltage. The HOMO (highest occupied molecular orbital) level of the hole injecting material is preferably located between the work function of the anode materials and the HOMO level of its neighboring organic material layer. Specific examples of the hole injecting material include metal porphyrin, oligothiophene, organic materials of arylamine series, hexanitrile hexaazatriphenylene, organic materials of quinacridone series, organic materials of perylene series, anthraquinone, and conductive polymers of polyaniline and polythiophene series, but are not limited thereto.

The hole transporting material is preferably a material having high hole mobility, which can transfer holes from the anode or the hole injecting layer toward the light emitting layer. Specific examples thereof include organic materials of arylamine series, conductive polymers and block copolymers having both conjugated portions and non-conjugated portions, but are not limited thereto.

The light emitting material are a material capable of emitting visible light by accepting and recombining holes from the hole transporting layer and electrons from the electron transporting layer, preferably a material having high quantum efficiency for fluorescence and phosphorescence. Specific examples thereof include 8-hydroxyquinoline aluminum complex ($Alq_3$); compounds of carbazole series; dimerized styryl compounds; BAlq; 10-hydroxybenzoquinoline-metal compounds; compounds of benzoxazole, benzthiazole and benzimidazole series; polymers of poly(p-phenylenevinylene) (PPV) series; spiro compounds; and compounds of polyfluorene and rubrene series, but are not limited thereto.

The electron transporting material is suitably a material having high electron mobility, which can transfer electrons from the cathode to the light emitting layer. Specific examples thereof include 8-hydroxyquinoline aluminum complex; complexes including $Alq_3$; organic radical compounds; and hydroxyflavone-metal complexes, but are not limited thereto.

The organic light emitting device according to the present invention may be of a front-side, backside or double-sided light emission according to the materials used.

The compound according to the present invention can function in an organic electronic device including an organic solar cell, an organic photoconductor and an organic transistor, according to a principle similar to that applied to the organic light emitting device.

MODE FOR THE INVENTION

Hereinbelow, the preferred Examples of the present invention will be presented for further understanding the present invention. However, the following Examples are presented merely for illustrative purpose, and thus do not limit the scope of the present invention.

The compound of Formula 1 according to the present invention can be prepared in multi-step chemical reactions. The preparation of the compound is described by way of Examples below. As will be clear in Examples, a certain intermediate compound is first prepared, and then the intermediate compound is used to prepare the compound of Formula 1. Exemplary intermediate compounds are listed below as Compounds A through Y. In these compounds, Br or Cl may be substituted with any other reactive atoms or functional groups.

[Compound A]
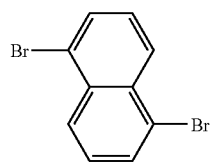

[Compound B]
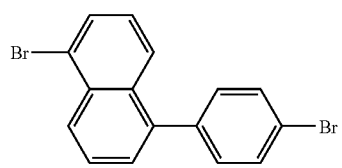

[Compound C]
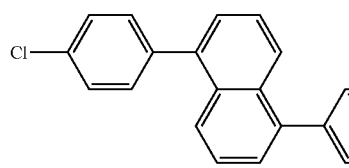

[Compound D]
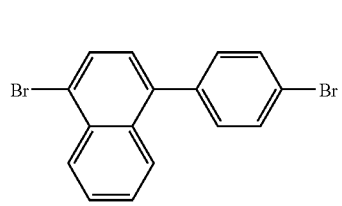

[Compound E]
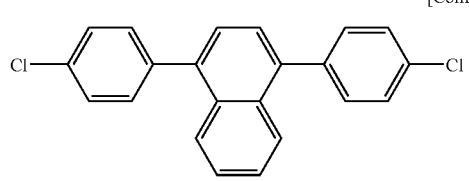

[Compound F]
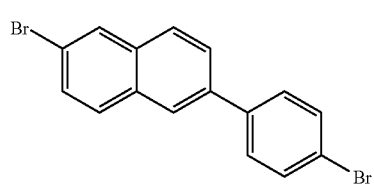

[Compound G]
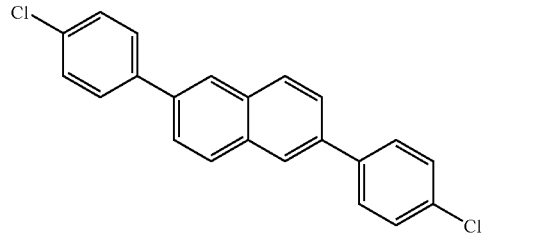

[Compound H]
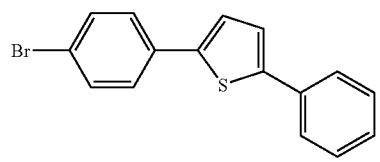

[Compound I]
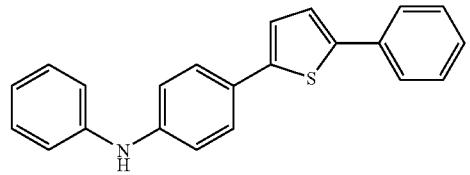

[Compound J]
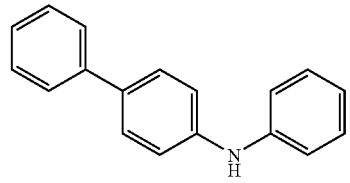

[Compound K]
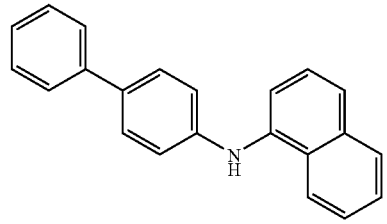

[Compound L]
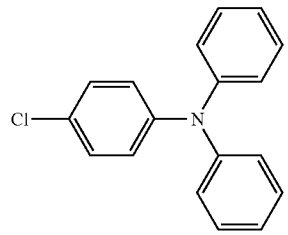

[Compound M]
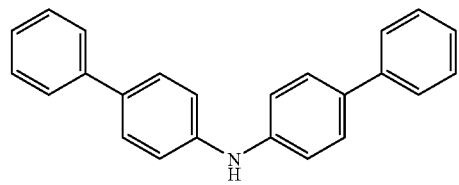

-continued

[Compound N]
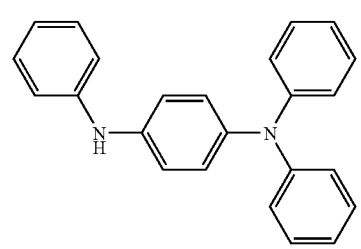

[Compound O]
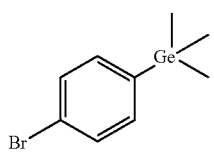

[Compound P]
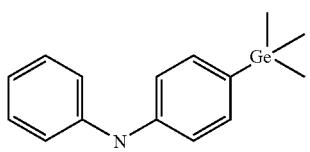

[Compound Q]
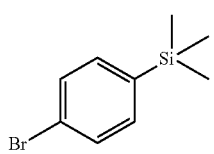

[Compound R]
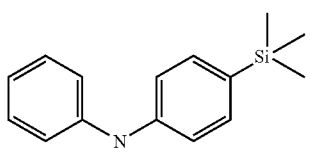

[Compound S]
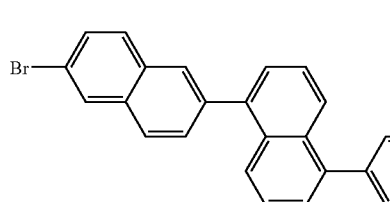

[Compound T]
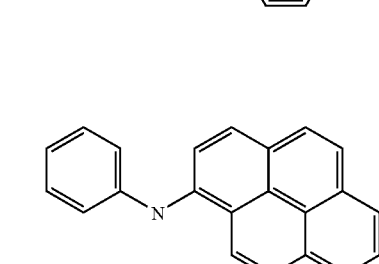

[Compound U]
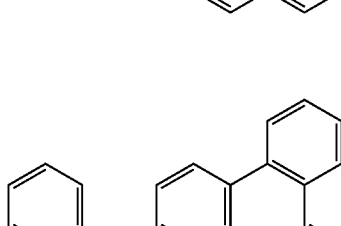

-continued

[Compound V]
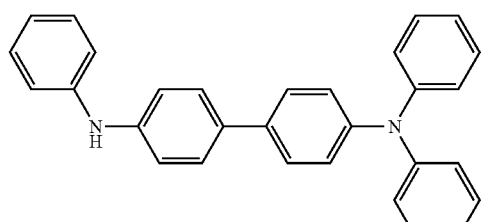

[Compound W]
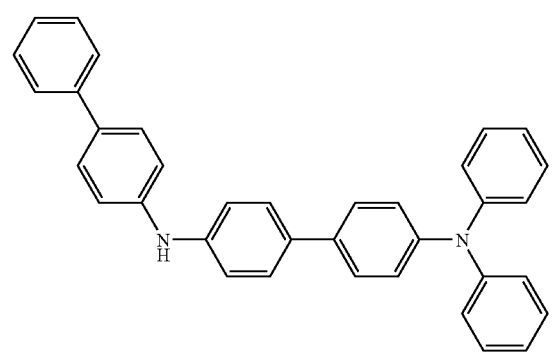

[Compound X]
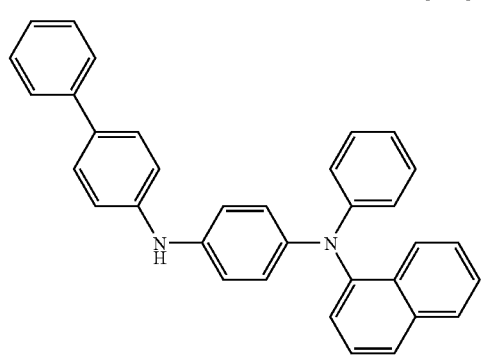

[Compound Y]
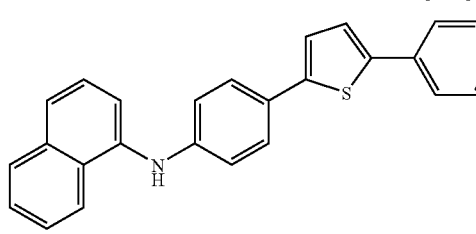

Preparation Example 1

Preparation of Compound A

Under cooling conditions, 1,5-diaminonaphthalene (12 g, 75.9 mmol) was dissolved in H$_2$O (300 mL) and concentrated sulfuric acid (20 mL). NaNO$_2$ dissolved in H$_2$O (300 mL) was slowly added dropwise, and then stirred at 0° C. for 45 min. The reaction mixture was filtered, and then CuBr$_2$ (30 g, 52.3 mmol), HBr (48%, 450 mL), and H$_2$O (450 mL) were added to the filtrate. The reaction solution was stirred at 0° C. for 1 hr and at room temperature for 2 hrs, and then stirred again at 70° C. for 30 min. The reaction solution was separated using benzene. The organic layer was dried over sodium sulfate,

Preparation Example 2

Preparation of Compound B

Under N$_2$ atmosphere, 1,5-dibromonaphthalene (5 g, 17.5 mmol), 4-bromophenylboronic acid (3.5 g, 17.5 mmol), and Pd(PPh$_3$)$_4$ (1.0 g, 0.88 mmol) were added to a 2 M K$_2$CO$_3$ aqueous solution (10 mL) and THF (tetrahydrofuran, 200 mL), and refluxed under stirring for about 24 hrs. After completion of the reaction, the mixture was cooled to room temperature, and the organic layer was separated from the reaction mixture. The organic layer was dried over magnesium sulfate, and then distilled under reduced pressure. The residue was purified by column chromatography to obtain a compound B (3.16 g, 50%).

MS: [M]=362.

Preparation Example 3

Preparation of Compound C

Under N$_2$ atmosphere, 1,5-dibromonaphthalene (5 g, 17.5 mmol), 4-chlorophenylboronic acid (6.6 g, 42.0 mmol), and Pd(PPh$_3$)$_4$ (1.0 g, 0.87 mmol) were added to a 2 M K$_2$CO$_3$ aqueous solution (20 mL) and THF (tetrahydrofuran, 200 mL), and refluxed under stirring for about 24 hrs. After completion of the reaction, the mixture was cooled to room temperature, and the organic layer was separated from the reaction mixture. The organic layer was dried over magnesium sulfate, and then distilled under reduced pressure. The residue was purified with THF/EtOH to obtain a compound C (5.9 g, 97%).

MS: [M+H]+=348.

Preparation Example 4

Preparation of Compound D

A compound D (3.16 g, 50%) was prepared in the same manner as in Preparation Example 2, except that 1.4-dibromonaphthalene (5 g, 17.5 mmol) was used instead of 1,5-dibromonaphthalene (5 g, 17.5 mmol) in Preparation Example 2.

MS: [M]=362.

Preparation Example 5

Preparation of Compound E

A compound E (5.9 g, 97%) was prepared in the same manner as in Preparation Example 3, except that 1.4-dibromonaphthalene (5 g, 17.5 mmol) was used instead of 1,5-dibromonaphthalene (5 g, 17.5 mmol) in Preparation Example 3.

MS: [M]=348.

Preparation Example 6

Preparation of Compound F

A compound F (3.16 g, 50%) was prepared in the same manner as in Preparation Example 2, except that 2.6-dibromonaphthalene (5 g, 17.5 mmol) was used instead of 1,5-dibromonaphthalene (5 g, 17.5 mmol) in Preparation Example 2.

MS: [M]=362.

Preparation Example 7

Preparation of Compound G

A compound G (5.9 g, 97%) was prepared in the same manner as in Preparation Example 3, except that 2.6-dibromonaphthalene (5 g, 17.5 mmol) was used instead of 1,5-dibromonaphthalene (5 g, 17.5 mmol) in Preparation Example 3.

MS: [M]=348.

Preparation Example 8

Preparation of Compound H

2-Thiophene boronic acid (10 g, 78.1 mmol) and bromo benzene (7.48 mL, 70.3 mmol) were dissolved in anhydrous THF (300 mL), and then Pd(PPh$_3$)$_4$ (4.51 g, 3.91 mmol) and a K$_2$CO$_3$ aqueous solution (156 mL, 312.4 mmol) were added thereto, refluxed for 3 hrs. The organic layer was extracted with ethyl acetate, and dried over magnesium sulfate. The organic layer was filtered under reduced pressure, and concentrated to remove the solvent. The residue was purified by column chromatography, and then recrystallized in THF and ethanol to obtain a white solid compound (10 g, £0%).

MS: [M+H]=161.

The prepared white solid compound (5 g, 31.3 mmol) were dissolved in anhydrous THF (200 mL), and then cooled to −10° C. Then, n-butyllithium (15 mL, 37.5 mmol) was slowly added dropwise, and stirred for 1 hr. Subsequently, the reaction temperature was decreased to −78° C., and then boronic acid trimethylester (10.5 mL, 93.75 mmol) was slowly added, stirred for 12 hrs. After the temperature was decreased to 0° C., a 2 N hydrochloric acid aqueous solution (16 mL) was added thereto, and stirred to obtain a white precipitate. The organic layer was extracted with THF, dried over magnesium sulfate, and then filtered under reduced pressure. The filtrate was concentrated to remove the solvent, and the resultant was dissolved in THF. An excessive amount of aqueous solution was added thereto, and the organic layer was separated with dimethylchloromethane. A hydrochloric acid aqueous solution was added to the separated aqueous layer, precipitated, filtered to obtain a compound (2.7 g, 42%).

3-Bromoiodobenzene (3.5 g, 12.3 mmol) and the above prepared compound (2.5 g, 12.3 mmol) were dissolved in anhydrous THF (100 mL), and Pd(PPh$_3$)$_4$ (0.71 g, 0.61 mmol) were added thereto. K$_2$CO$_3$ (3.4 g, 24.6 mmol) dissolved in H 0 (50 mL) was added thereto, and then refluxed under stirring. After 3 hrs, the resultant was washed with brine, and the organic layer was extracted with ethyl acetate. The organic layer was dried over magnesium sulfate, filtered under reduced pressure, and concentrated to remove the solvent. The residue was purified by column chromatography to obtain a compound H (2.9 g, 75%).

MS: [M+H]+=315.

Preparation Example 9

Preparation of Compound I

Aniline (10 ml, 109.74 mmol) and the compound H prepared in Preparation Example 8 (34.5 g, 109.7 mmol) were (continued from previous: and then distilled under reduced pressure. The residue was purified by column chromatography to obtain a compound A (5.9 g, 27%). MS: [M]=286.)

dissolved in 300 ml of toluene. Then, bis(dibenzylidene-acetone)palladium (0) (Pd(dba)$_2$, 1.26 g, 2.20 mmol), 50 wt % of tri-t-butylphosphine (1.30 ml, 3.29 mmol) and sodium t-butoxide (21.09 g, 219.5 mmol) were added thereto, and refluxed under nitrogen atmosphere for 2 hrs. Distilled water was added to the reaction solution to terminate the reaction. The organic layer was extracted, and separated by column chromatography using n-hexane/THF (10/1), stirred in pet. Ether, and dried under vacuum to obtain a compound I (15 g, yield 56%).

MS: [M+H]$^+$=327.

Preparation Example 10

Preparation of Compound J

Under nitrogen atmosphere, aniline (10 ml, 109.74 mmol) and 4-bromo biphenyl (25.6 g, 109.7 mmol) were dissolved in 300 ml of toluene. Then, bis(dibenzylidene-acetone)palladium (0) (Pd(dba)$_2$, 1.26 g, 2.20 mmol), 50 wt % of tri-t-butylphosphine (1.30 ml, 3.29 mmol) and sodium t-butoxide (21.09 g, 219.5 mmol) were added thereto, and refluxed under nitrogen atmosphere for 2 hrs. Distilled water was added to the reaction solution to terminate the reaction. The organic layer was extracted, and separated by column chromatography using n-hexane/THF (10/1), stirred in pet. Ether, and dried under vacuum to obtain a compound J (15 g, yield 56%).

MS: [M+H]$^+$=245.

Preparation Example 11

Preparation of Compound K

1-Aminonaphthalene (7.4 g, 51.48 mmol) and 4-bromobiphenyl (12 g, 51.48 mmol) were dissolved in 200 ml of toluene. Then, bis(dibenzylidene-acetone)palladium (0) (Pd(dba)$_2$, 0.89 g, 1.54 mmol), 50 wt % of tri-t-butylphosphine (0.60 ml, 1.54 mmol) and sodium t-butoxide (9.90 g, 103.0 mmol) were added thereto, and refluxed under nitrogen atmosphere for 2 hrs. Distilled water was added to the reaction solution to terminate the reaction. The organic layer was extracted, and separated by column chromatography using n-hexane/THF (15/1), stirred in pet. Ether, and dried under vacuum to obtain a compound K (6.3 g, yield 42%).

MS: [M+H]$^+$=295.

Preparation Example 12

Preparation of Compound L

Under nitrogen atmosphere, 4.18 g of N,N-diphenylamine (24.7 mmol) and 4.72 g of 1-bromo-4-chlorophenyl (24.7 mmol) were dissolved in 200 ml of toluene. Then, 5.94 g of sodium t-butoxide (61.8 mmol), 0.43 g of bis(dibenzylidene-acetone)palladium (0) (0.74 mmol), and 0.61 ml of 50 wt % tri-t-butylphosphine (1.24 mmol) were added thereto, and refluxed under nitrogen atmosphere for 5 hrs. Distilled water was added to the reaction solution to terminate the reaction. The organic layer was extracted, and separated by column chromatography using n-hexane/THF (10/1), stirred in pet. Ether, and dried under vacuum to obtain a compound L (2.9 g, yield 42%).

MS: [M+H]$^+$=279.

Preparation Example 13

Preparation of Compound M 4-aminobiphenyl (30.5 g, 180.17 mmol) and 4-bromo biphenyl (40 g, 171.59 mmol) were dissolved in 500 ml of toluene. Then, bis(dibenzylidene-acetone)palladium (0) (Pd(dba)$_2$, 2.07 g, 3.60 mmol), 50 wt % of tri-t-butylphosphine (2.2 ml, 5.41 mmol) and sodium t-butoxide (51.94 g, 540.5 mmol) were added thereto, and refluxed under nitrogen atmosphere for 2 hrs. Distilled water was added to the reaction solution to terminate the reaction. The organic layer was extracted, and separated by column chromatography using n-hexane/THF (15/1), stirred in pet. Ether, and dried under vacuum to obtain a compound M (32 g, yield 58%).

MS: [M+H]$^+$=321.

Preparation Example 14

Preparation of Compound N

Aniline (10 ml, 109.74 mmol) and the compound L prepared in Preparation Example 12 (30.7 g, 109.7 mmol) were dissolved in 300 ml of toluene. Then, bis(dibenzylidene-acetone)palladium (0) (Pd(dba)$_2$, 1.26 g, 2.20 mmol), 50 wt % of tri-t-butylphosphine (1.30 ml, 3.29 mmol) and sodium t-butoxide (21.09 g, 219.5 mmol) were added thereto, and refluxed under nitrogen atmosphere for 2 hrs. Distilled water was added to the reaction solution to terminate the reaction. The organic layer was extracted, and separated by column chromatography using n-hexane/THF (10/1), stirred in pet. Ether, and dried under vacuum to obtain a compound N (15 g, yield 56%).

MS: [M+H]$^+$=336.

Preparation Example 15

Preparation of Compound O

Dibromobenzene (20 g, 84.78 mmol) was dried under nitrogen atmosphere at room temperature, and dissolved in THF (200 mL). The solution was cooled to −78° C. n-Butyl lithium (34 mL, 2.5 M pentane solution) were slowly added to the solution at −78° C., and the temperature of the mixture was raised to 0° C. for about 1 hr. Trimethyl-germanium bromide (18 ml, 101.74 mmol) was added thereto, and the temperature was raised to room temperature for 1 hr. After completion of the reaction, the mixture was extracted with ethyl acetate, and then dried over magnesium sulfate. The residue was distilled under reduced pressure to obtain a compound O (20 g, 90%).

MS: (M+)=273.

Preparation Example 16

Preparation of Compound P

Under nitrogen atmosphere, the compound O (18 g, 65.45 mmol), aniline (6.6 ml, 72 mmol), Pd(dba)$_2$ (0.125 g, 0.13 mmol), P(t-Bu)$_3$ (0.04 g, 0.2 mmol) and sodium t-butoxide (1.80) g, 18.7 mmol) were added to toluene (200 mL), and refluxed for about 3 hrs. After completion of the reaction, the reaction mixture was cooled to room temperature, and added to a mixture of THF and H$_2$O. The organic layer was separated, dried over magnesium sulfate, and concentrated. The residue was purified by column chromatography to obtain a compound P (16 g, 85%).

MS: [M]=286.

Preparation Example 17

Preparation of Compound Q

Dibromobenzene (20 g, 84.78 mmol) was dried under nitrogen atmosphere at room temperature, and dissolved in THF (200 mL). The solution was cooled to −78° C. n-Butyl lithium (34 mL, 2.5 M pentane solution) were slowly added to the solution at −78° C., and the temperature of the mixture was raised to 0° C. for about 1 hr. Chloro trimethylsilane (13 ml, 101.74 mmol) was added thereto, and the temperature was raised to room temperature for 1 hr. After completion of the reaction, the mixture was extracted with ethyl acetate, and then dried over magnesium sulfate. The residue was distilled under reduced pressure to obtain a compound Q (18 g, 93%).
MS: (M+)=229.

Preparation Example 18

Preparation of Compound R

Under nitrogen atmosphere, the compound Q (15 g, 65.45 mmol), aniline (6.6 ml, 72 mmol), Pd(dba)$_2$ (0.125 g, 0.13 mmol), P(t-Bu)$_3$ (0.04 g, 0.2 mmol) and sodium t-butoxide (1.80 g, 18.7 mmol) were added to toluene (200 mL), and refluxed for about 3 hrs. After completion of the reaction, the reaction mixture was cooled to room temperature, and added to a mixture of THF and H$_2$O. The organic layer was separated, dried over magnesium sulfate, and concentrated. The residue was purified by column chromatography to obtain a compound R (15 g, 86%).
MS: [M]=143.

Preparation Example 19

Preparation of Compound S

Under N atmosphere, 1,5-diboronate naphthalene (6.65 g, 17.5 mmol), 2,6-dibromophenyl (10 g, 35.0 mmol), Pd(PPh$_3$)$_4$ (1.0 g, 0.87 mmol) were added to a 2 M K$_2$CO$_3$ aqueous solution (20 mL) and THF (200 mL), and refluxed under stirring for about 24 hrs. After completion of the reaction, the mixture was cooled to room temperature, and the organic layer was separated from the reaction mixture. The organic layer was dried over magnesium sulfate, and purified by column chromatography to obtain a compound S (2.8 g, 30%).
MS: [M+H]+=538.

Preparation Example 20

Preparation of Compound T

Aniline (10 ml, 109.74 mmol) and 1-bromopyrene (30.84 g, 109.7 mmol) were dissolved in 300 ml of toluene. Then, bis(dibenzylidene-acetone)palladium (0) (Pd(dba)$_2$, 1.26 g, 2.20 mmol), 50 wt % of tri-t-butylphosphine (1.30 ml, 3.29 mmol) and sodium t-butoxide (21.09 g, 219.5 mmol) were added thereto, and refluxed under nitrogen atmosphere for 2 hrs. Distilled water was added to the reaction solution to terminate the reaction. The organic layer was extracted, and separated by column chromatography using n-hexane/THF (10/1), stirred in pet. Ether, and dried under vacuum to obtain a compound T (18.3 g, yield 56%).
MS: [M+H]$^+$=298.

Preparation Example 21

Preparation of Compound U

Aniline (10 ml, 109.74 mmol) and 1-bromoperylene (36.33 g, 109.7 mmol) were dissolved in 300 ml of toluene. Then, bis(dibenzylidene-acetone)palladium (0) (Pd(dba)$_2$, 1.26 g, 2.20 mmol), 50 wt % of tri-t-butylphosphine (1.30 ml, 3.29 mmol) and sodium t-butoxide (21.09 g, 219.5 mmol) were added thereto, and refluxed under nitrogen atmosphere for 2 hrs. Distilled water was added to the reaction solution to terminate the reaction. The organic layer was extracted, and separated by column chromatography using n-hexane/THF (10/1), stirred in pet. Ether, and dried under vacuum to obtain a compound U (20 g, yield 56%).
MS: [M+H]$^+$=331.

Preparation Example 22

Preparation of Compound V

Under nitrogen atmosphere, 4.00 g of 4-chlorobiphenyl-N,N-diphenylamine (11.2 mmol) and 1.13 ml of aniline (12.4 mmol) were dissolved in 100 ml of toluene. Then, sodium t-butoxide (2.70 g, 28.1 mmol), bis(dibenzylidene-acetone)palladium (0) (0.13 g, 0.23 mmol), and 50 wt % of a tri-t-butylphosphine toluene solution (0.17 ml, 0.34 mmol) were added thereto, and refluxed under nitrogen atmosphere for 5 hrs. Distilled water was added to the reaction solution to terminate the reaction. The organic layer was extracted, and separated by column chromatography using n-hexane/THF (10/1), stirred in pet. Ether, and dried under vacuum to obtain a compound V (3.8 g, yield 81%).
MS: [M+H]$^+$=412.

Preparation Example 23

Preparation of Compound W

Under nitrogen atmosphere, 8.80 g of 4-chlorobiphenyl-N,N-diphenylamine (24.7 mmol) and 6.28 g of 4-aminobiphenyl (37.1 mmol) were dissolved in 200 ml of toluene. Then, sodium t-butoxide (5.94 g, 61.8 mmol), bis(dibenzylidene-acetone)palladium (0) (0.43 g, 0.74 mmol), and 50 wt % of a tri-t-butylphosphine toluene solution (0.61 ml, 1.24 mmol) were added thereto, and refluxed under nitrogen atmosphere for 5 hrs. Distilled water was added to the reaction solution to terminate the reaction. The organic layer was extracted, and separated by column chromatography using n-hexane/THF (10/1), stirred in pet. Ether, and dried under vacuum to obtain a compound W (7.0 g, yield 58%).
MS: [M+H]$^+$=489.

Preparation Example 24

Preparation of Compound X

Under nitrogen atmosphere, 6.28 g of 4-aminobiphenyl (37.1 mmol), 8.12 g of 4-chlorophenyl-N,N-(1-naphthyl)phenylamine (24.7 mmol) were dissolved in 300 ml of toluene. Then, bis(dibenzylidene-acetone)palladium (0) (Pd(dba)$_2$, 1.26 g, 2.20 mmol), 50 wt % of tri-t-butylphosphine (1.30 ml, 3.29 mmol) and sodium t-butoxide (21.09 g, 219.5 mmol) were added thereto, and refluxed under nitrogen atmosphere for 2 hrs. Distilled water was added to the reaction solution to terminate the reaction. The organic layer was extracted, and separated by column chromatography using n-hexane/THF (10/1), stirred in pet. Ether, and dried under vacuum to obtain a compound X (6.39 g, yield 56%).
MS: [M+H]$^+$=462.

Preparation Example 25

Preparation of Compound Y

1-Aminonaphthalene (16.37 g, 109.74 mmol) and the compound H prepared in Preparation Example 8 (34.5 g, 109.7 mmol) were dissolved in 300 ml of toluene. Then, bis(dibenzylidene-acetone)palladium (0) (Pd(dba)$_2$, 1.26 g, 2.20 mmol), 50 wt % of tri-t-butylphosphine (1.30 ml, 3.29 mmol) and sodium t-butoxide (21.09 g, 219.5 mmol) were added thereto, and refluxed under nitrogen atmosphere for 2 hrs. Distilled water was added to the reaction solution to terminate the reaction. The organic layer was extracted, and separated by column chromatography using n-hexane/THF (10/1), stirred in pet. Ether, and dried under vacuum to obtain a compound Y (23 g, yield 56%).

MS: [M+]$^+$=377.

Example 1

Preparation of Compound 2-1

Under nitrogen atmosphere, the compound A prepared in Preparation Example 1 (2.4 g, 8.5 mmol), the compound R prepared in Preparation Example 18 (2.9 g, 20.4 mmol), Pd(dba)$_2$ (0.097 g, 0.17 mmol), P(t-Bu)$_3$ (0.05 g, 0.255 mmol) and sodium t-butoxide (2.45 g, 25.5 mmol) were dissolved in toluene (100 mL), and refluxed for 2 hrs. After completion of the reaction, the mixture was cooled to room temperature, and the reaction mixture was added to a mixture of THF and H$_2$O. The organic layer was separated, dried over MgSO$_4$, and concentrated. The residue was purified by column chromatography to obtain a compound 2-1 (3.19 g, 62%).

MS: [M]=606.

Example 2

Preparation of Compound 2-6

Under nitrogen atmosphere, the compound A prepared in Preparation Example 1 (2.4 g, 8.5 mmol), the compound P prepared in Preparation Example 16 (5.83 g, 20.4 mmol), Pd(dba)$_2$ (0.097 g, 0.17 mmol), P(t-Bu)$_3$ (0.05 g, 0.255 mmol) and sodium t-butoxide (2.45 g, 25.5 mmol) were dissolved in toluene (100 mL), and refluxed for 2 hrs. After completion of the reaction, the mixture was cooled to room temperature, and the reaction mixture was added to a mixture of THF and H$_2$O. The organic layer was separated, dried over MgSO$_4$, and concentrated. The residue was purified by column chromatography to obtain a compound 2-6 (3.64 g, (60%)).

MS: [M]=696.

Example 3

Preparation of Compound 2-12

Under nitrogen atmosphere, the compound A prepared in Preparation Example 1 (2.4 g, 8.5 mmol), the compound H prepared in Preparation Example 8 (6.43 g, 20.4 mmol), Pd(dba)$_2$ (0.097 g, 0.17 mmol), P(t-Bu)$_3$ (0.05 g, 0.255 mmol) and sodium t-butoxide (2.45 g, 25.5 mmol) were dissolved in toluene (100 mL), and refluxed for 2 hrs. After completion of the reaction, the mixture was cooled to room temperature, and the reaction mixture was added to a mixture of THF and H$_2$O. The organic layer was separated, dried over MgSO$_4$, and concentrated. The residue was purified by column chromatography to obtain a compound 2-12 (4.29 g, 65%).

MS: [M]=778.

Example 4

Preparation of Compound 2-52

Under nitrogen atmosphere, the compound B prepared in Preparation Example 2 (3.07 g, 8.5 mmol), the compound J prepared in Preparation Example 10 (5.00 g, 20.4 mmol), Pd(dba)$_2$ (0.097 g, 0.17 mmol), P(t-Bu)$_3$ (0.05 g, 0.255 mmol) and sodium t-butoxide (2.45 g, 25.5 mmol) were dissolved in toluene (100 mL), and refluxed for 2 hrs. After completion of the reaction, the mixture was cooled to room temperature, and the reaction mixture was added to a mixture of THF and H$_2$O. The organic layer was separated, dried over MgSO$_4$, and concentrated. The residue was purified by column chromatography to obtain a compound 2-52 (3.64 g, (0%)).

MS: [M]=690.

Example 5

Preparation of Compound 3-52

A Compound 3-52 (3.64 g, 60%) was obtained in the same manner as in Example 4, except that the compound F (3.07 g, 8.5 mmol) prepared in Preparation Example 6 was used instead of compound B (3.07 g, 8.5 mmol) prepared in Preparation Example 2 in Example 4.

MS: [M]=690.

Example 6

Preparation of Compound 4-52

A Compound 4-52 (3.64 g, 60%) was obtained in the same manner as in Example 4, except that the compound D (3.07 g, 8.5 mmol) prepared in Preparation Example 4 was used instead of compound B (3.07 g, 8.5 mmol) prepared in Preparation Example 2 in Example 4.

MS: [M]=690.

Example 7

Preparation of Compound 2-64

A Compound 2-64 (4.5 g, 62%) was obtained in the same manner as in Example 3, except that the compound B (3.07 g, 8.5 mmol) prepared in Preparation Example 2 was used instead of compound A (2.43 g, 8.5 mmol) prepared in Preparation Example 1 in Example 3.

MS: [M]=854.

Example 8

Preparation of Compound 2-68

A Compound 2-68 (4.01 g, 60%) was obtained in the same manner as in Example 3, except that the compound T (6.08 g, 20.4 mmol) prepared in Preparation Example 20 was used instead of compound J (5.00 g, 20.4 mmol) prepared in Preparation Example 10 in Example 4.

MS: [M]=786.

Example 9

Preparation of Compound 2-70

A Compound 2-70 (3.77 g, 50%) was obtained in the same manner as in Example 4, except that the compound U (7.00 g, 20.4 mmol) prepared in Preparation Example 21 was used instead of compound J (5.00 g, 20.4 mmol) prepared in Preparation Example 10 in Example 4.

MS: [M]=886.

Example 10

Preparation of Compound 2-78

Under nitrogen atmosphere, the compound B prepared in Preparation Example 2 (3.07 g, 8.5 mmol), the compound M prepared in Preparation Example 13 (6.56 g, 20.4 mmol), Pd(dba)$_2$ (0.097 g, 0.17 mmol), P(t-Bu)$_3$ (0.05 g, 0.255 mmol) and sodium t-butoxide (2.45 g, 25.5 mmol) were dissolved in toluene (150 mL), and refluxed for 2 hrs. After completion of the reaction, the mixture was cooled to room temperature, and the reaction mixture was added to a mixture of THF and H$_2$O. The organic layer was separated, dried over MgSO$_4$, and concentrated. The residue was purified by column chromatography to obtain a compound 2-78 (4.65 g, 65%).

MS: [M]=842.

Example 11

Preparation of Compound 3-78

A Compound 3-78 (3.64 g, 60%) was obtained in the same manner as in Example 10, except that the compound F (3.07 g, 8.5 mmol) prepared in Preparation Example 6 was used instead of compound B (3.07 g, 8.5 mmol) prepared in Preparation Example 2 in Example 10.

MS: [M]=842.

Example 12

Preparation of Compound 4-78

A Compound 4-78 (3.64 g, 60%) was obtained in the same manner as in Example 10, except that the compound D (3.07 g, 8.5 mmol) prepared in Preparation Example 4 was used instead of compound B (3.07 g, 8.5 mmol) prepared in Preparation Example 2 in Example 10.

MS: [M]=842.

Example 13

Preparation of Compound 2-104

Under nitrogen atmosphere, the compound C prepared in Preparation Example 3 (2.96 g, 8.5 mmol), the compound J prepared in Preparation Example 10 (5.00 g, 20.4 mmol), Pd(dba)$_2$ (0.097 g, 0.17 mmol), P(t-Bu)$_3$ (0.05 g, 0.255 mmol) and sodium t-butoxide (2.45 g, 25.5 mmol) were dissolved in toluene (150 mL), and refluxed for 2 hrs. After completion of the reaction, the mixture was cooled to room temperature, and the reaction mixture was added to a mixture of THF and H$_2$O. The organic layer was separated, dried over MgSO$_4$, and concentrated. The residue was purified by column chromatography to obtain a compound 2-104 (4.23 g, 65%).

MS: [M]=766.

Example 14

Preparation of Compound 2-113

Under nitrogen atmosphere, the compound C prepared in Preparation Example 3 (2.96 g, 8.5 mmol), the compound M prepared in Preparation Example 13 (6.56 g, 20.4 mmol), Pd(dba)$_2$ (0.097 g, 0.17 mmol), P(t-Bu)$_3$ (0.05 g, 0.255 mmol) and sodium t-butoxide (2.45 g, 25.5 mmol) were dissolved in toluene (150 mL), and refluxed for 2 hrs. After completion of the reaction, the mixture was cooled to room temperature, and the reaction mixture was added to a mixture of THF and H$_2$O. The organic layer was separated, dried over MgSO$_4$, and concentrated. The residue was purified by column chromatography to obtain a compound 2-113 (5.07 g, 65%).

MS: [M]=918.

Example 15

Preparation of Compound 2-119

A Compound 2-119 (4.39 g, 60%) was obtained in the same manner as in Example 13, except that the compound T (6.08 g, 20.4 mmol) prepared in Preparation Example 20 was used instead of compound J (5.00 g, 20.4 mmol) prepared in Preparation Example 10 in Example 13.

MS: [M]=862.

Example 16

Preparation of Compound 2-121

A Compound 2-121 (4.08 g, 50%) was obtained in the same manner as in Example 13, except that the compound U (7.00 g, 20.4 mmol) prepared in Preparation Example 21 was used instead of compound J (5.00 g, 20.4 mmol) prepared in Preparation Example 10 in Example 13.

MS: [M]=962.

Example 17

Preparation of Compound 2-125

A Compound 2-125 (6.08 g, 65%) was obtained in the same manner as in Example 13, except that the compound V (8.41 g, 20.4 mmol) prepared in Preparation Example 22 was used instead of compound J (5.00 g, 20.4 mmol) prepared in Preparation Example 10 in Example 13.

MS: [M]=1100.

Example 18

Preparation of Compound 2-127

A Compound 2-127 (6.12 g, 60 %) was obtained in the same manner as in Example 13, except that the compound X (9.44 g, 20.4 mmol) prepared in Preparation Example 24 was used instead of compound J (5.00 g, 20.4 mmol) prepared in Preparation Example 10 in Example 13.

MS: [M]=1200.

Example 19

Preparation of Compound 2-131

A Compound 2-131 (5.25 g, 60%) was obtained in the same manner as in Example 13, except that the compound Y (7.70 g, 20.4 mmol) prepared in Preparation Example 25 was used instead of compound J (5.00 g, 20.4 mmol) prepared in Preparation Example 10 in Example 13.

MS: [M]=1030.

Example 20

Preparation of Compound 2-155

Under nitrogen atmosphere, the compound S prepared in Preparation Example 19 (4.58 g, 8.5 mmol), the compound J prepared in Preparation Example 10 (5.00 g, 20.4 mmol), Pd(dba)$_2$ (0.097 g, 0.17 mmol), P(t-Bu)$_3$ (0.05 g, 0.255 mmol) and sodium t-butoxide (2.45 g, 25.5 mmol) were dissolved in toluene (150 mL), and refluxed for 2 hrs. After completion of the reaction, the mixture was cooled to room temperature, and the reaction mixture was added to a mixture of THF and H$_2$O. The organic layer was separated, dried over MgSO$_4$, and concentrated. The residue was purified by column chromatography to obtain a compound 2-155 (4.78 g, 65%).

MS: [M]=866.

Example 21

Preparation of Compound 2-179

A Compound 2-179 (5.19 g, (60%) was obtained in the same manner as in Example 13, except that the compound M

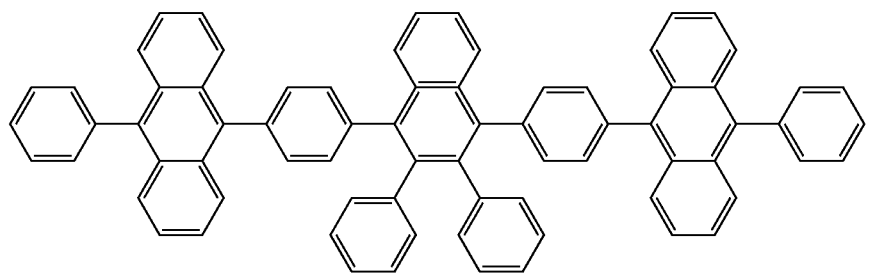

[Compound Z]

(6.56 g, 20.4 mmol) prepared in Preparation Example 13 was used instead of compound J (5.00 g, 20.4 mmol) prepared in Preparation Example 10 in Example 13.

MS: [M]=1018.

Experimental Example 1

A glass substrate (Corning 7059 glass), on which a thin film of ITO (indium tin oxide) was coated to a thickness of 1,000 Å, was immersed in distilled water having a detergent dissolved therein to wash the substrate with ultrasonic waves. The detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using solvents such as isopropyl alcohol, acetone and methanol. The resultant product was dried, and then transported to a plasma washing machine. The substrate was washed for 5 minutes using an oxygen plasma, and then transported to a vacuum depositing machine.

On the ITO electrode, 3,6-bis-2-naphthylphenylamino-N-[4-(2-naphthylphenyl)aminophenyl]carbazole (800 Å), and 4,4'-bis[N-(1-naphthyl)-N-phenyl amino]biphenyl (NPB) (300 Å) were sequentially deposited to form a hole injecting layer and a hole transporting layer, respectively. The compound 2-1 prepared in Example 1 (2 wt %) was deposited thereon with the following compound Z (300 Å) to form a light emitting layer, and then 9,10-bis-2-naphthyl-2-[4-(N-phenylbenzoimidazoyl)phenyl]anthracene (300 Å) was coated by thermal vacuum deposition to form an electron transporting layer.

Lithium fluoride (LiF) and aluminum were sequentially deposited on the electron transporting layer to thicknesses of 12 Å and 2,000 Å, respectively, to form a cathode, thereby obtaining an organic light emitting device.

In the above process, the deposition rate of the organic material was maintained at 0.4 to 0.7 Å/sec and the deposition rate of lithium fluoride on the cathode was maintained at 0.3 Å/sec and the deposition rate of aluminum was maintained at 2 Å/sec. The degree of vacuum upon deposition was maintained at $2 \times 10^{-7}$ to $5 \times 10^{-8}$ torr.

When a forward electric field of 7.8 V was applied to the organic light emitting device as prepared above, blue light emission of 4.9 cd/A was observed with x=0.170, and y=0.150 based on the 1931 CIE color coordinate at a current density of 100 mA/cm$^2$.

Experimental Example 2

An organic light emitting device was prepared in the same manner as in Experimental Example 1, except that the compound 2-68 prepared in Example 8 was used instead of the compound 2-1 in Experimental Example 1.

When a forward electric field of 7.9 V was applied to the organic light emitting device as prepared above, blue light emission of 4.7 cd/A was observed with x=0.170, and y=0.151 based on the 1931 CIE color coordinate at a current density of 100 mA/cm$^2$.

Experimental Example 3

An organic light emitting device was prepared in the same manner as in Experimental Example 1, except that the compound 2-70 prepared in Example 9 was used instead of the compound 2-1 in Experimental Example 1.

When a forward electric field of 7.7 V was applied to the organic light emitting device as prepared above, blue light emission of 4.8 cd/A was observed with x=0.171, and y=0.153 based on the 1931 CIE color coordinate at a current density of 100 mA/cm$^2$.

Experimental Example 4

An organic light emitting device was prepared in the same manner as in Experimental Example 1, except that the compound 2-119 prepared in Example 15 was used instead of the compound 2-1 in Experimental Example 1.

When a forward electric field of 7.7 V was applied to the organic light emitting device as prepared above, blue light emission of 4.9 cd/A was observed with x=0.171, and y=0.153 based on the 1931 CIE color coordinate at a current density of 100 mA/cm$^2$.

Experimental Example 5

An organic light emitting device was prepared in the same manner as in Experimental Example 1, except that the compound 2-121 prepared in Example 16 was used instead of the compound 2-1 in Experimental Example 1.

When a forward electric field of 7.8 V was applied to the organic light emitting device as prepared above, blue light emission of 4.8 cd/A was observed with x=0.172, and y=0.153 based on the 1931 CIE color coordinate at a current density of 100 mA/cm².

Experimental Example 6

An organic light emitting device was prepared in the same manner as in Experimental Example 1, except that the compound 2-179 prepared in Example 21 was used instead of the compound 2-1 in Experimental Example 1.

When a forward electric field of 7.9 V was applied to the organic light emitting device as prepared above, blue light emission of 4.9 cd/A was observed with x=0.173, and y=0.152 based on the 1931 CIE color coordinate at a current density of 100 mA/cm².

Experimental Example 7

On the ITO electrode thus prepared, hexanitrile hexaazatriphenylene (hereinafter, referred to as HAT) of the following Formula was coated to thicknesses of 500 by thermal vacuum deposition, so as to form anode comprising an ITO conducting layer and an n-type organic material.

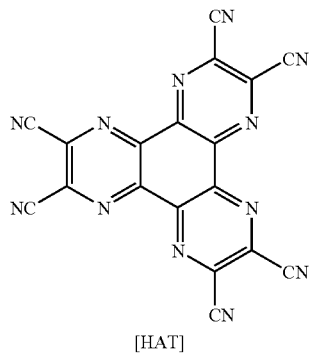

[HAT]

On the layer, the compound 2-52 (400 Å) prepared in Example 4 was vacuum-deposited to form a hole transporting layer. On the hole transporting layer, Alq₃ was vacuum-deposited to a thickness of 300 Å, thus to form a light emitting layer. On the light emitting layer, the electron transporting layer material of the following Formula was deposited to a thickness of 200 Å, thus to form an electron transporting layer.

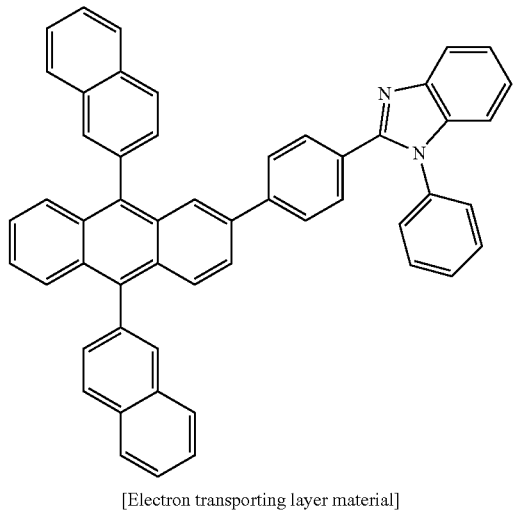

[Electron transporting layer material]

On the electron transporting layer, lithium fluoride (LiF) and aluminum were sequentially vacuum-deposited to a thickness of 12 Å and 2,000 Å, respectively, to form a cathode.

In the above process, the deposition rate of the organic material was maintained at 0.3 to 0.8 Å/sec and the deposition rates of lithium fluoride and aluminum of the cathode were maintained at 0.3 Å/sec and 1.5 to 2.5 Å/sec, respectively. The vacuum degree during deposition was maintained at $1 \times 10^{-7} \sim 3 \times 10^{-7}$ torr.

An electric field of 4.54 V was observed in the above prepared device at a forward current density of 100 mA/cm², and spectrum was observed with a light efficiency of 1.89 lm/W. Light emitting by the device at the above drive voltage indicates that the compound 2-52 of Example 4 formed between the hole injecting layer and light emitting layer functions to transport a hole.

Experimental Example 8

An organic light emitting device was prepared in the same manner as in Experimental Example 7, except that the compound 3-78 prepared in Example 11 was used instead of the compound 2-52 used as a hole transporting layer in Experimental Example 7.

An electric field of 4.52 V was observed in the above prepared device at a forward current density of 100 mA/cm², and spectrum was observed with a light efficiency of 1.91 lm/W. Light emitting by the device at the above drive voltage indicates that the compound 3-78 formed between the thin film on the substrate and hole transporting layer functions to transport a hole.

Experimental Example 9

An organic light emitting device was prepared in the same manner as in Experimental Example 7, except that the compound 4-78 prepared in Example 12 was used instead of the compound 2-52 used as a hole transporting layer in Experimental Example 7.

An electric field of 4.53 V was observed in the above prepared device at a forward current density of 100 mA/cm², and spectrum was observed with a light efficiency of 1.90 lm/W. Light emitting by the device at the above drive voltage indicates that the compound 4-78 formed between the thin film on the substrate and hole transporting layer functions to transport a hole.

Experimental Example 10

An organic light emitting device was prepared in the same manner as in Experimental Example 7, except that the compound 2-104 prepared in Example 13 was used instead of the compound 2-52 used as a hole transporting layer in Experimental Example 7.

An electric field of 4.50 V was observed in the above prepared device at a forward current density of 100 mA/cm$^2$, and spectrum was observed with a light efficiency of 1.89 lm/W. Light emitting by the device at the above drive voltage indicates that the compound 2-104 formed between the thin film on the substrate and hole transporting layer functions to transport a hole.

Experimental Example 11

An organic light emitting device was prepared in the same manner as in Experimental Example 7, except that the compound 2-113 prepared in Example 14 was used instead of the compound 2-52 used as a hole transporting layer in Experimental Example 7.

An electric field of 4.31 V was observed in the above prepared device at a forward current density of 100 mA/cm$^2$, and spectrum was observed with a light efficiency of 1.98 lm/W. Light emitting by the device at the above drive voltage indicates that the compound 2-113 formed between the thin film on the substrate and hole transporting layer functions to transport a hole.

Experimental Example 12

An organic light emitting device was prepared in the same manner as in Experimental Example 7, except that the compound 2-125 prepared in Example 17 was used instead of the compound 2-52 used as a hole transporting layer in Experimental Example 7.

An electric field of 4.52 V was observed in the above prepared device at a forward current density of 100 mA/cm$^2$, and spectrum was observed with a light efficiency of 1.91 lm/W. Light emitting by the device at the above drive voltage indicates that the compound 2-125 formed between the thin film on the substrate and hole transporting layer functions to transport a hole.

Experimental Example 13

An organic light emitting device was prepared in the same manner as in Experimental Example 7, except that the compound 2-127 prepared in Example 18 was used instead of the compound 2-52 used as a hole transporting layer in Experimental Example 7.

An electric field of 4.53 V was observed in the above prepared device at a forward current density of 100 mA/cd, and spectrum was observed with a light efficiency of 1.90 lm/W. Light emitting by the device at the above drive voltage indicates that the compound 2-127 formed between the thin film on the substrate and hole transporting layer functions to transport a hole.

Experimental Example 14

An organic light emitting device was prepared in the same manner as in Experimental Example 7, except that the compound 2-131 prepared in Example 19 was used instead of the compound 2-52 used as a hole transporting layer in Experimental Example 7.

An electric field of 4.31 V was observed in the above prepared device at a forward current density of 100 mA/cm$^2$, and spectrum was observed with a light efficiency of 1.96 lm/W. Light emitting by the device at the above drive voltage indicates that the compound 2-131 formed between the thin film on the substrate and hole transporting layer functions to transport a hole.

Experimental Example 15

An organic light emitting device was prepared in the same manner as in Experimental Example 7, except that the compound 2-155 prepared in Example 20 was used instead of the compound 2-52 used as a hole transporting layer in Experimental Example 7.

An electric field of 4.52 V was observed in the above prepared device at a forward current density of 100 mA/cd, and spectrum was observed with a light efficiency of 1.91 lm/W. Light emitting by the device at the above drive voltage indicates that the compound 2-155 formed between the thin film on the substrate and hole transporting layer functions to transport a hole.

Comparative Experimental Example 1

An organic light emitting device was prepared in the same manner as in Experimental Example 7, except that a commercial NPB material of the following Formula was used instead of the compound 2-52 used as a hole transporting layer in Experimental Example 7.

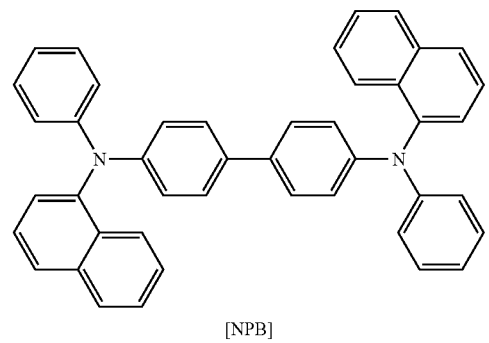

[NPB]

An electric field of 4.82 V was observed in the above prepared device at a forward current density of 100 mA/cm$^2$, and spectrum was observed with a light efficiency of 1.87 lm/W.

The diamine derivative according to the present invention was found to exhibit effects of lower operating voltage and increased efficiency of an organic electronic device.

The invention claimed is:
1. A diamine derivative represented by any one of the following Formulae 2, 3, 5 and 6:

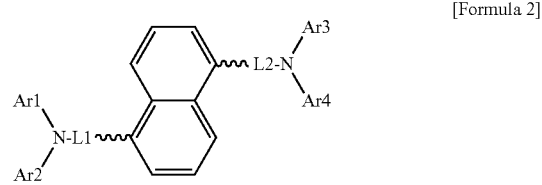

[Formula 2]

-continued

[Formula 3]

[Formula 5]

[Formula 6]

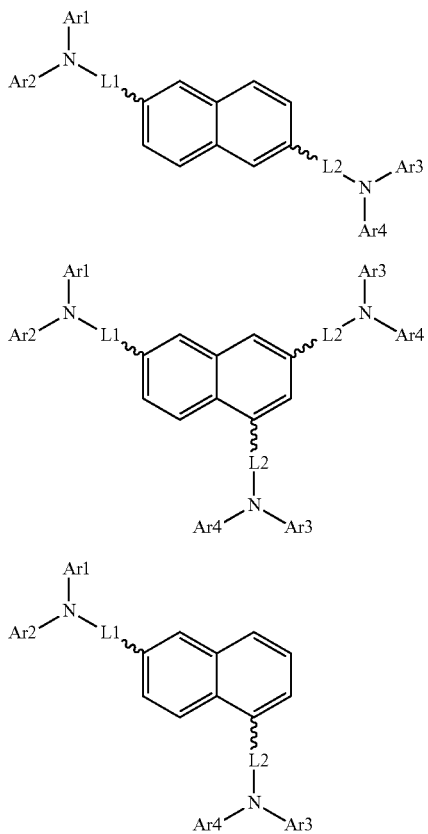

wherein at least one of L1 and L2 of Formulae 2, 3, 5 and 6 is a $C_6$~$C_{20}$ arylene group unsubstituted or substituted with one or more groups selected from the group consisting of a $C_1$~$C_{20}$ alkyl group, a $C_2$~$C_{20}$ alkenyl group, a $C_2$~$C_{20}$ alkynyl group, a $C_3$~$C_{20}$ cycloalkyl group, a $C_2$~$C_{20}$ heterocycloalkyl group, a $C_6$~$C_{20}$ aryl group and a $C_5$~$C_{20}$ heteroaryl group; or a $C_5$~$C_{20}$ heteroarylene group unsubstituted or substituted with one or more groups selected from the group consisting of a $C_1$~$C_{20}$ alkyl group, a $C_2$~$C_{20}$ alkenyl group, a $C_2$~$C_{20}$ alkynyl group, a $C_3$~$C_{20}$ cycloalkyl group, a $C_2$~$C_{20}$ heterocycloalkyl group, a $C_6$~$C_{20}$ aryl group and a $C_5$~$C_{20}$ heteroaryl group, the rest is a direct bond; a $C_6$~$C_{10}$ arylene group unsubstituted or substituted with one or more groups selected from the group consisting of a $C_1$~$C_{10}$ alkyl group, a $C_2$~$C_{20}$ alkenyl group, a $C_2$~$C_{20}$ alkynyl group, a $C_2$~$C_{20}$ cycloalkyl group, a $C_2$~$C_{20}$ heterocycloalkyl group, a $C_6$~$C_{20}$ aryl group and a $C_5$~$C_{20}$ heteroaryl group; or a $C_5$~$C_{20}$ heteroarylene group unsubstituted or substituted with one or more groups selected from the group consisting of a $C_1$~$C_{20}$ alkyl group, a $C_2$~$C_{20}$ alkenyl group, a $C_2$~$C_{20}$ alkynyl group, a $C_3$~$C_{10}$ cycloalkyl group, a $C_2$~$C_{20}$ heterocycloalkyl group, a $C_6$~$C_{20}$ aryl group and a $C_5$~$C_{20}$ heteroaryl group; and Ar1, Ar2, Ar3 and Ar4 are same or different from each other, and are each independently hydrogen, a $C_6$~$C_{20}$ aryl group unsubstituted or substituted with halogen, CN, $NO_2$, a $C_1$~$C_{20}$ alkyl group, a $C_1$~$C_{20}$ alkoxy group, a $C_6$~$C_{20}$ aryl group, a $C_5$~$C_{20}$ heteroaryl group, a $C_6$~$C_{20}$ aryl amine group, a $C_6$~$C_{20}$ aryl thiophene group, a $C_3$~$C_{20}$ cycloalkyl group, —OR, —SR, —SeR, —TeR, —BRR', —AlRR', —SiRR'R", —GeRR'R", or —SnRR'R"; a $C_5$~$C_{20}$ heterocyclic group comprising O, N or S; or a condensed ring formed by fusing a $C_5$~$C_{20}$ alkylene group with a $C_6$~$C_{20}$ aryl group, wherein R, R', and R" are same or different from each other, and are each independently hydrogen, a $C_1$~$C_{20}$ alkyl group, a $C_3$~$C_{20}$ cycloalkyl group, a $C_6$~$C_{20}$ aryl group or a $C_5$~$C_{20}$ heterocyclic group.

2. The diamine derivative according to claim 1, wherein at least one of L1 and L2 of Formulae 2, 3, 5 and 6 is a $C_6$~$C_{20}$ arylene group, the rest is a direct bond or a $C_6$~$C_{20}$ arylene group.

3. The diamine derivative according to claim 1, wherein at least one of L1 and L2 of Formulae 2, 3, 5 and 6 is selected from the group consisting of a phenylene group and a naphthylene group, the rest is selected from the group consisting of a direct bond, a phenylene group, and a naphthylene group.

4. The diamine derivative according to claim 1, wherein Ar1 and Ar3 of Formulae 2, 3, 5 and 6 are same or different from each other, and are each independently selected from the group consisting of a phenyl group, a biphenyl group, a naphthyl group, and a phenyl group substituted with —SiRR'R" or —GeRR'R", wherein R, R', and R" are same or different from each other, and are each independently hydrogen, a $C_1$~$C_{20}$ alkyl group, a $C_3$~$C_{20}$ cycloalkyl group, a $C_6$~$C_{20}$ aryl group or a $C_5$~$C_{20}$ heterocyclic group.

5. The diamine derivative according to claim 1, wherein Ar2 and Ar4 of Formulae 2, 3, 5 and 6 are same or different from each other, and are each independently selected from the group consisting of a phenyl group, a biphenyl group, a naphthyl group, an anthracenyl group, a pyrenyl group, a phenylenyl group, a phenyl group substituted with —SiRR'R" or —GeRR'R", a $C_5$~$C_{20}$ heterocyclic group comprising S, a $C_6$~$C_{20}$ aryl amine group, and a $C_6$~$C_{20}$ aryl group, wherein R, R', and R" are same or different from each other, and are each independently hydrogen, a $C_1$~$C_{20}$ alkyl group, a $C_3$~$C_{20}$ cycloalkyl group, a $C_6$~$C_{20}$ aryl group or a $C_5$~$C_{20}$ heterocyclic group.

6. The diamine derivative according to claim 1, wherein L1, L2, Ar1, Ar2, Ar3, and Ar4 of Formulae 2, 3, 5 and 6 are selected from the groups of the following Table 1.

TABLE 1

| | L1 | L2 | Ar1 |
|---|---|---|---|
| 49 | — | ⌬-⌬ | -⌬ |
| 50 | — | ⌬-⌬ | -⌬ |

TABLE 1-continued
| 51 | — | 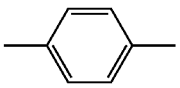 | 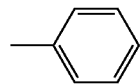 |
| 52 | — |  | 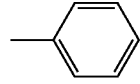 |
| 53 | — | 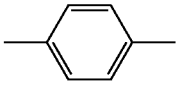 | 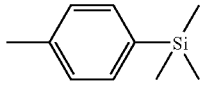 |
| 54 | — | 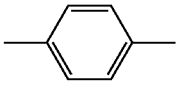 | 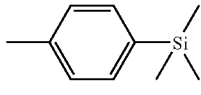 |
| 55 | — | 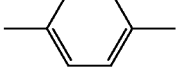 | 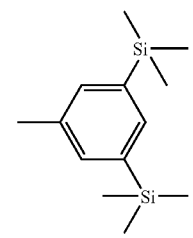 |
| 56 | — | 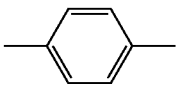 | 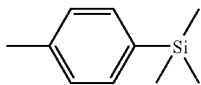 |
| 57 | — | 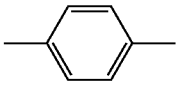 | 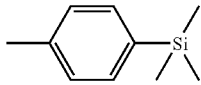 |
| 58 | — |  | 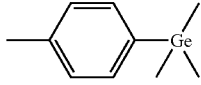 |
| 59 | — |  | 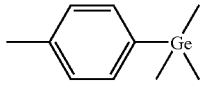 |
| 60 | — | 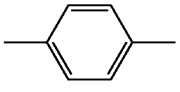 | 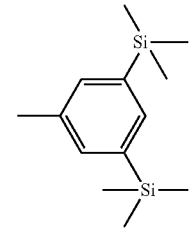 |
| 61 | — | 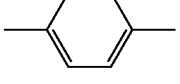 | 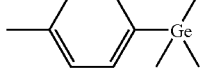 |
| 62 | — | 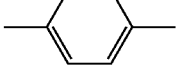 | 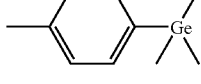 |
| 63 | — | 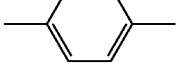 | 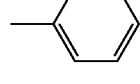 |

TABLE 1-continued
| | | | |
|---|---|---|---|
| 64 | — | 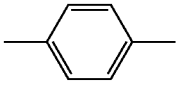 | 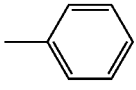 |
| 65 | — | 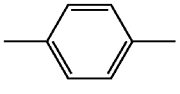 | 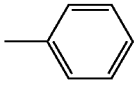 |
| 66 | — | 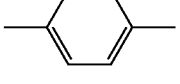 | 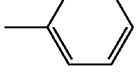 |
| 67 | — | 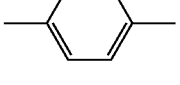 | 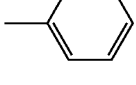 |
| 68 | — | 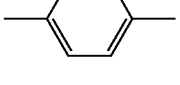 | 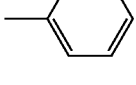 |
| 69 | — | 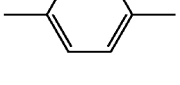 | 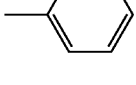 |
| 70 | — | 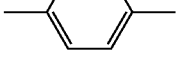 | 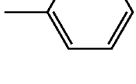 |
| 71 | — | 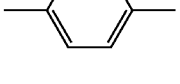 | 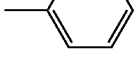 |
| 72 | — | 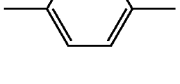 | 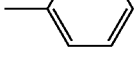 |
| 73 | — | 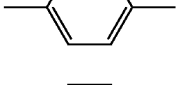 | 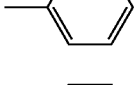 |
| 74 | — | 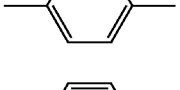 | 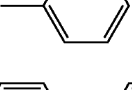 |
| 75 | — | 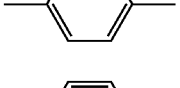 | 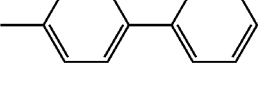 |
| 76 | — | 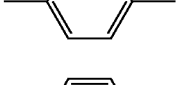 |  |
| 77 | — | 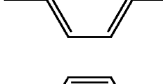 | 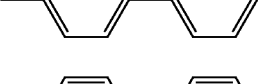 |
| 78 | — | 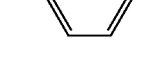 | 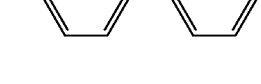 |

TABLE 1-continued
| | | | |
|---|---|---|---|
| 79 | — |  | 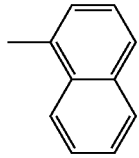 |
| 80 | — | 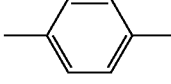 | 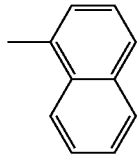 |
| 81 | — | 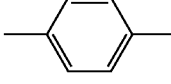 | 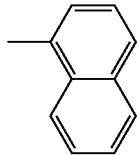 |
| 82 | — | 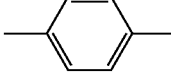 | 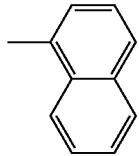 |
| 83 | — | 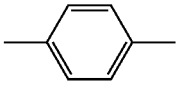 | 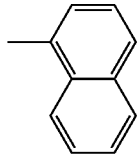 |
| 84 | — | 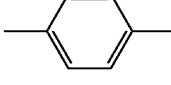 | 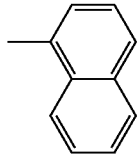 |
| 85 | — | 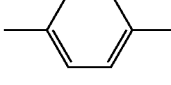 | 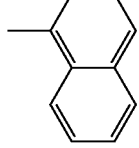 |
| 86 | — | 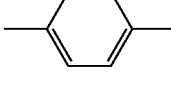 | 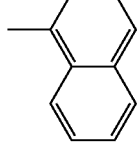 |
| 87 | — | 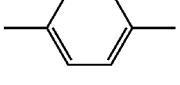 | 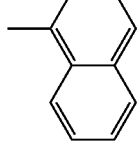 |

TABLE 1-continued
| | | | |
|---|---|---|---|
| 88 | — | 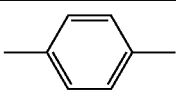 | 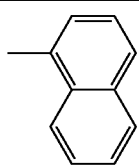 |
| 89 | — | 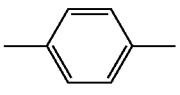 | 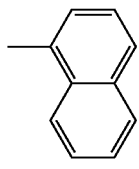 |
| 90 | — | 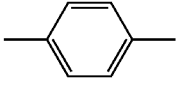 | 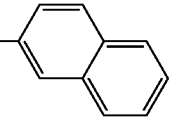 |
| 91 | — | 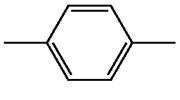 | 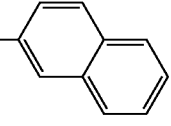 |
| 92 | — | 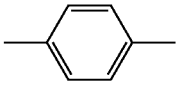 | 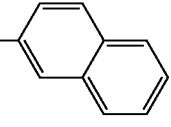 |
| 93 | — | 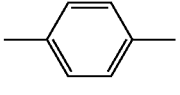 | 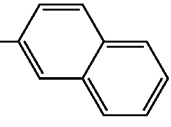 |
| 94 | — | 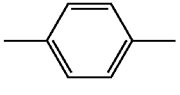 | 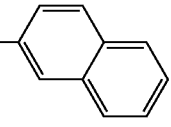 |
| 95 | — | 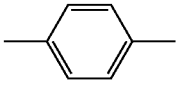 | 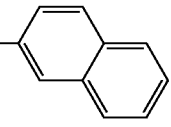 |
| 96 | — | 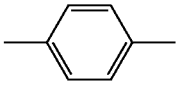 | 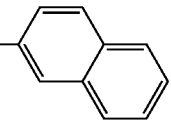 |
| 97 | — | 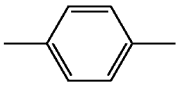 | 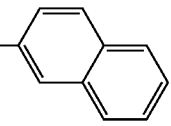 |
| 98 | — | 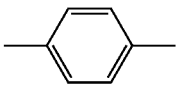 | 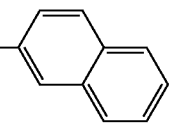 |

TABLE 1-continued
| | 197 | | 198 |
|---|---|---|---|
| 99 | — | 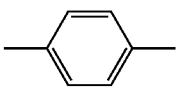 | 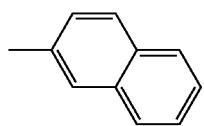 |
| 100 | — | 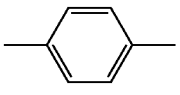 | 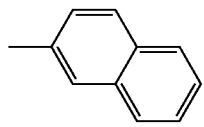 |
| 101 | 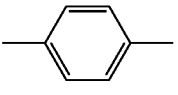 | 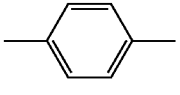 | 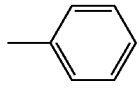 |
| 102 | 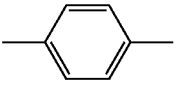 | 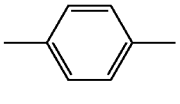 | 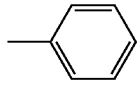 |
| 103 | 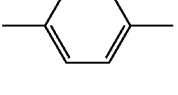 | 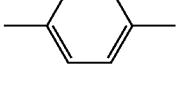 | 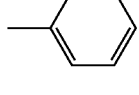 |
| 104 | 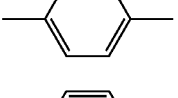 | 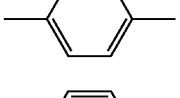 | 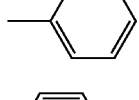 |
| 105 | 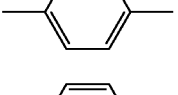 | 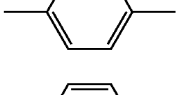 | 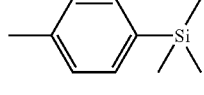 |
| 106 | 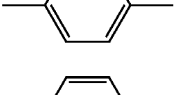 | 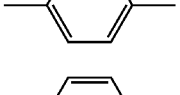 | 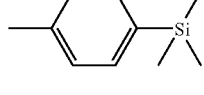 |
| 107 | 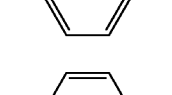 | 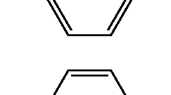 | 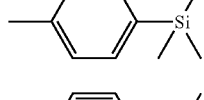 |
| 108 | 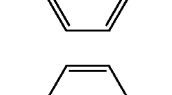 | 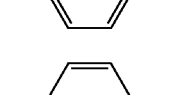 | 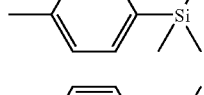 |
| 109 | 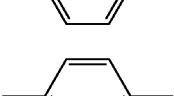 | 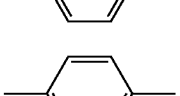 | 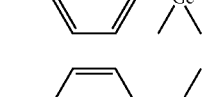 |
| 110 | 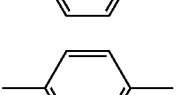 | 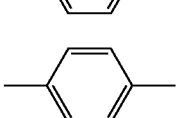 | 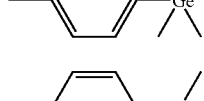 |
| 111 | 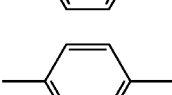 | 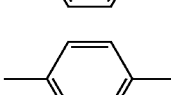 |  |
| 112 | 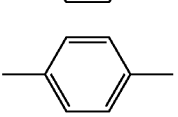 | 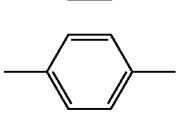 | 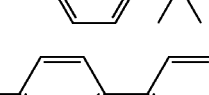 |
| 113 |  |  | 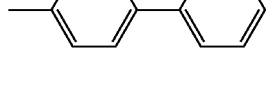 |

TABLE 1-continued
| | | | |
|---|---|---|---|
| 114 | 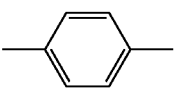 | 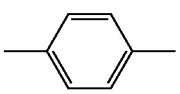 | 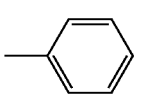 |
| 115 | 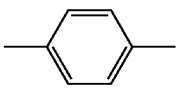 | 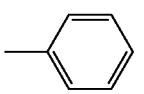 | 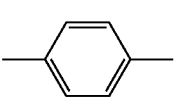 |
| 116 | 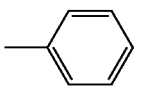 |  |  |
| 117 | 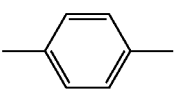 | 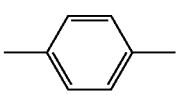 | 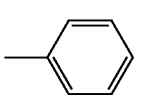 |
| 118 | 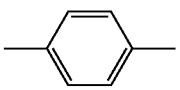 | 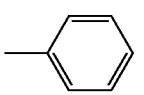 |  |
| 119 | 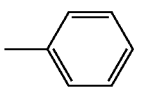 |  | 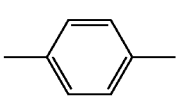 |
| 120 |  | 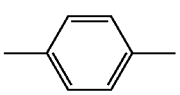 | 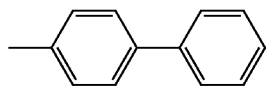 |
| 121 | 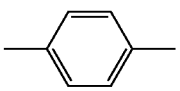 | 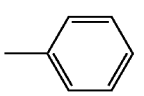 |  |
| 122 | 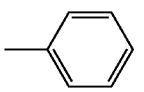 |  | 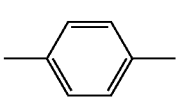 |
| 123 |  | 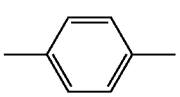 | 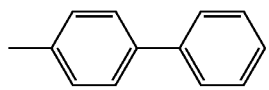 |
| 124 | 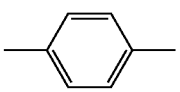 | 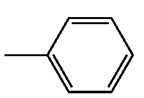 |  |
| 125 | 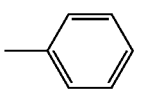 |  | 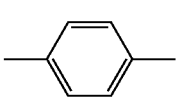 |
| 126 |  | 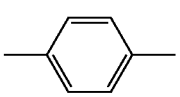 | 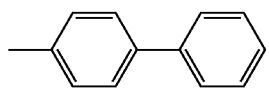 |
| 127 | 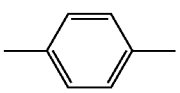 | 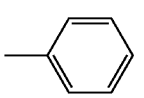 | 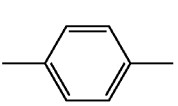 |
| 128 | 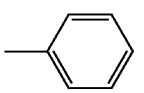 |  | 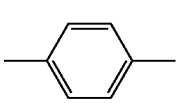 |
| 129 |  |  | 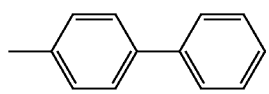 |

TABLE 1-continued
| | 201 | | 202 |
|---|---|---|---|
| 130 |  |  | 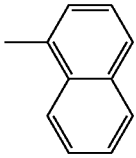 |
| 131 |  | 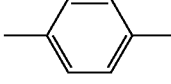 | 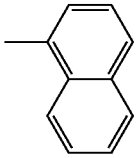 |
| 132 |  | 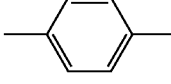 | 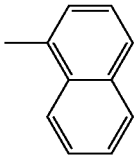 |
| 133 |  | 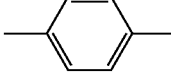 | 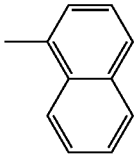 |
| 134 | 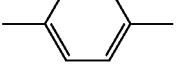 | 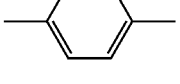 | 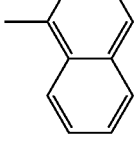 |
| 135 | 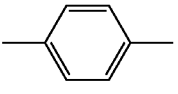 | 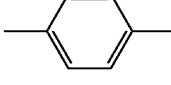 | 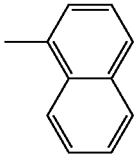 |
| 136 |  | 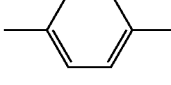 | 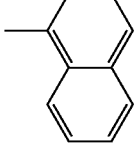 |
| 137 |  | 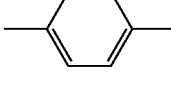 | 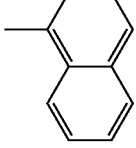 |
| 138 |  | 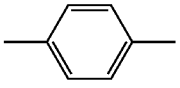 | 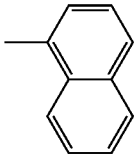 |

TABLE 1-continued

| | | | |
|---|---|---|---|
| 139 | phenylene | phenylene | 1-naphthyl |
| 140 | phenylene | phenylene | 1-naphthyl |
| 141 | phenylene | phenylene | 2-naphthyl |
| 142 | phenylene | phenylene | 2-naphthyl |
| 143 | phenylene | phenylene | 2-naphthyl |
| 144 | phenylene | phenylene | 2-naphthyl |
| 145 | phenylene | phenylene | 2-naphthyl |
| 146 | phenylene | phenylene | 2-naphthyl |
| 147 | phenylene | phenylene | 2-naphthyl |
| 148 | phenylene | phenylene | 2-naphthyl |
| 149 | phenylene | phenylene | 2-naphthyl |

TABLE 1-continued

| | 205 | | 206 |
|---|---|---|---|
| 150 | *p-phenylene* | *p-phenylene* | *2,6-naphthylene* |
| 151 | *p-phenylene* | *p-phenylene* | *2,6-naphthylene* |
| 152 | *2,6-naphthylene* | *2,6-naphthylene* | *phenyl* |
| 153 | *2,6-naphthylene* | *2,6-naphthylene* | *phenyl* |
| 154 | *2,6-naphthylene* | *2,6-naphthylene* | *phenyl* |
| 155 | *2,6-naphthylene* | *2,6-naphthylene* | *phenyl* |
| 156 | *2,6-naphthylene* | *2,6-naphthylene* | *p-(trimethylsilyl)phenyl* |
| 157 | *2,6-naphthylene* | *2,6-naphthylene* | *p-(trimethylsilyl)phenyl* |
| 158 | *2,6-naphthylene* | *2,6-naphthylene* | *p-(trimethylsilyl)phenyl* |
| 159 | *2,6-naphthylene* | *2,6-naphthylene* | *p-(trimethylsilyl)phenyl* |
| 160 | *2,6-naphthylene* | *2,6-naphthylene* | *p-(trimethylgermyl)phenyl* |
| 161 | *2,6-naphthylene* | *2,6-naphthylene* | *p-(trimethylgermyl)phenyl* |
| 162 | *2,6-naphthylene* | *2,6-naphthylene* | *p-(trimethylgermyl)phenyl* |
| 163 | *2,6-naphthylene* | *2,6-naphthylene* | *p-(trimethylgermyl)phenyl* |

TABLE 1-continued
| | | | |
|---|---|---|---|
| 164 | 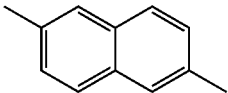 | 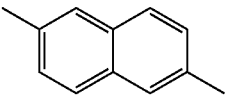 | 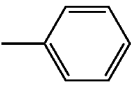 |
| 165 | 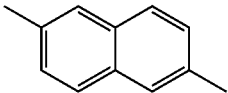 | 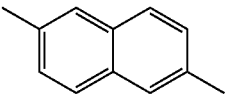 | 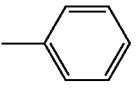 |
| 166 | 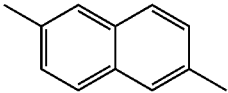 | 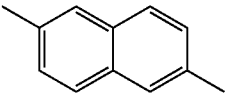 | 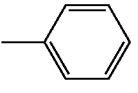 |
| 167 | 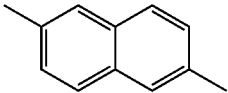 | 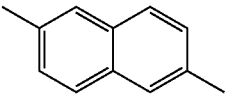 | 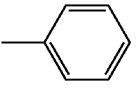 |
| 168 | 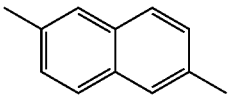 | 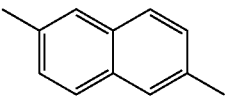 | 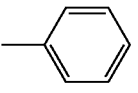 |
| 169 | 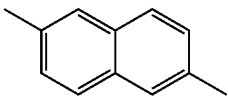 | 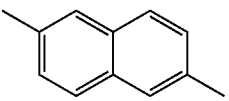 | 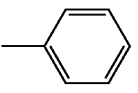 |
| 170 | 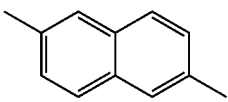 | 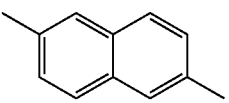 | 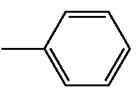 |
| 171 | 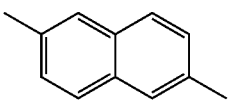 | 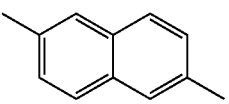 | 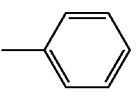 |
| 172 | 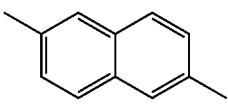 | 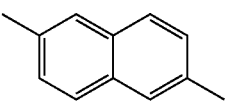 | 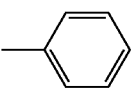 |
| 173 | 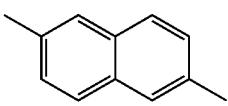 | 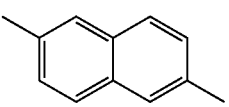 | 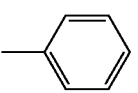 |
| 174 | 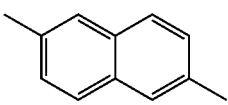 | 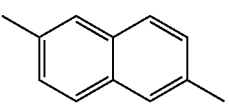 | 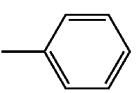 |
| 175 | 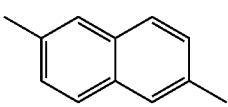 | 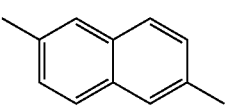 | 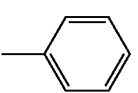 |
| 176 | 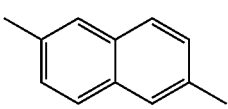 | 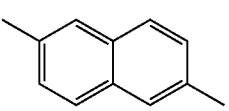 | 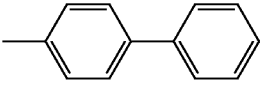 |
| 177 | 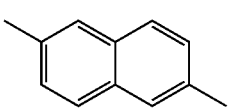 | 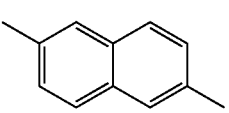 | 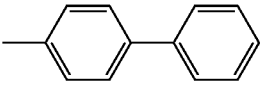 |

TABLE 1-continued
| | | | |
|---|---|---|---|
| 178 | 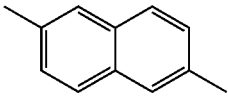 | 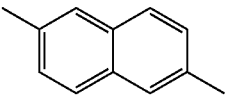 | 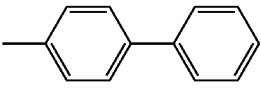 |
| 179 | 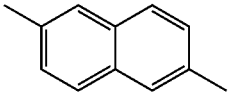 | 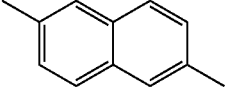 | 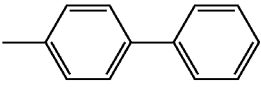 |
| 180 | 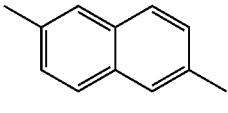 | 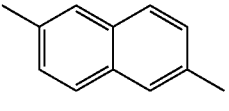 | 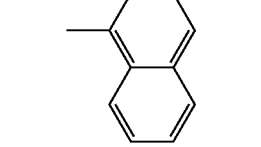 |
| 181 | 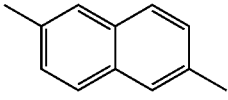 | 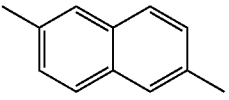 | 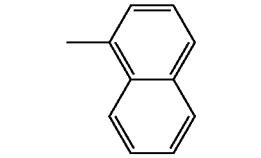 |
| 182 | 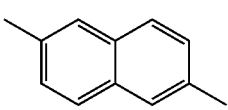 | 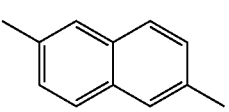 | 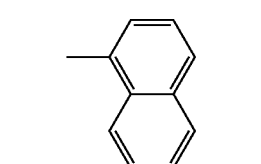 |
| 183 | 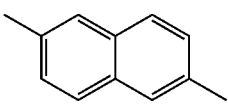 | 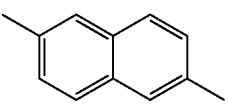 | 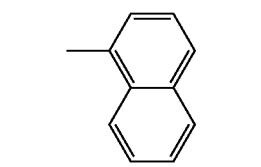 |
| 184 | 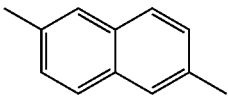 | 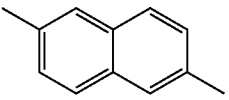 | 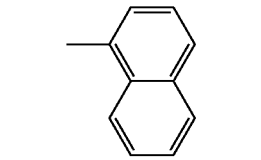 |
| 185 | 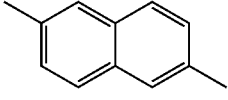 | 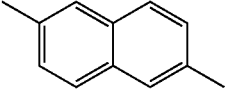 | 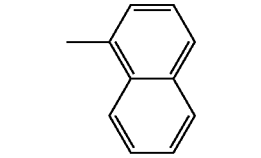 |
| 186 | 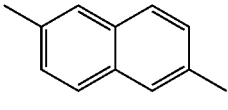 | 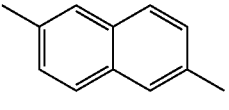 | 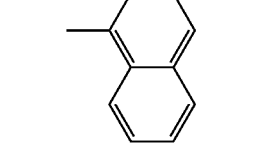 |
| 187 | 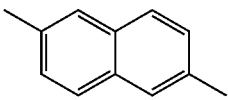 | 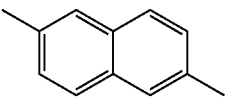 | 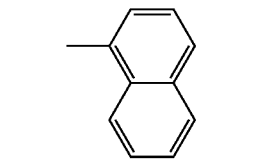 |

TABLE 1-continued
| | 211 | | 212 |
|---|---|---|---|
| 188 | 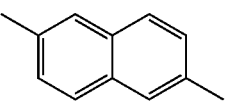 | 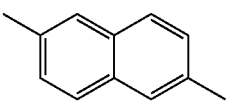 | 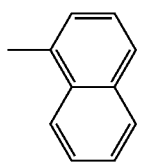 |
| 189 | 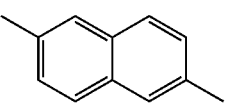 | 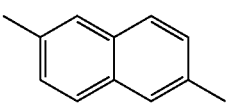 | 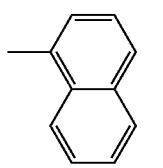 |
| 190 | 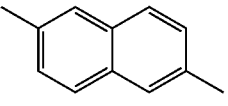 | 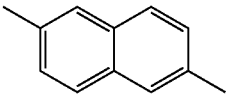 | 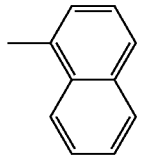 |
| 191 | 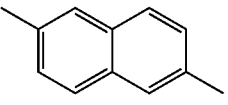 | 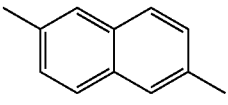 | 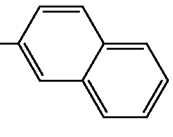 |
| 192 | 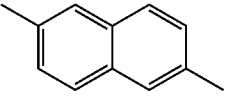 | 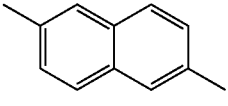 | 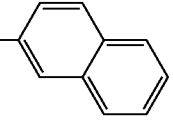 |
| 193 | 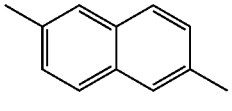 | 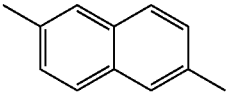 | 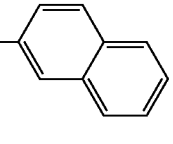 |
| 194 | 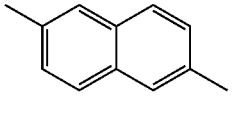 | 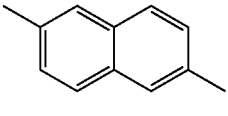 | 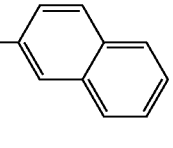 |
| 195 | 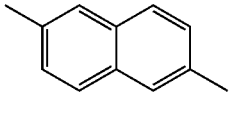 | 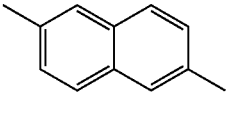 | 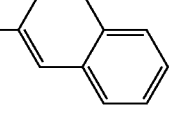 |
| 196 | 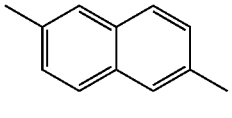 | 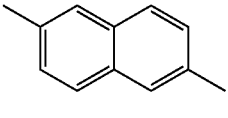 | 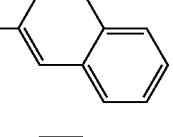 |
| 197 | 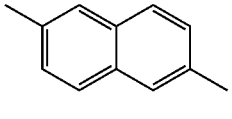 | 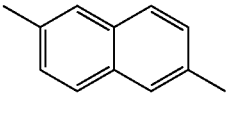 | 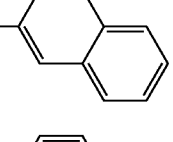 |
| 198 | 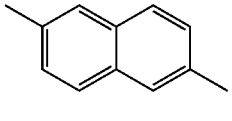 | 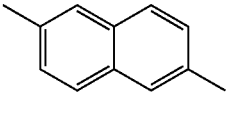 | 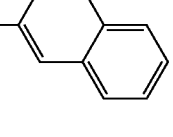 |

TABLE 1-continued
| | 213 | | 214 |
|---|---|---|---|
| 199 | 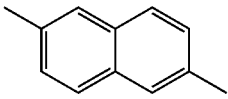 | 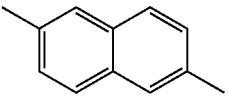 | 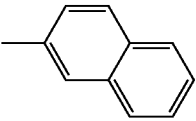 |
| 200 | 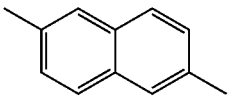 | 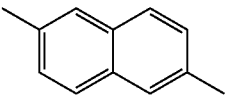 | 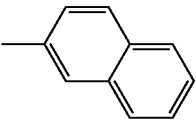 |
| 201 | 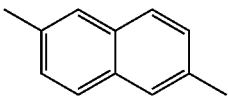 | 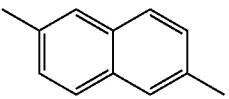 | 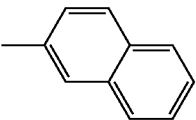 |
| 202 | 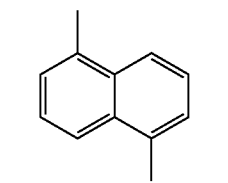 | 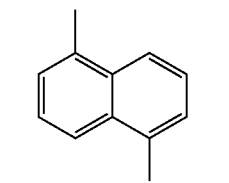 | 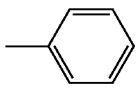 |
| 203 | 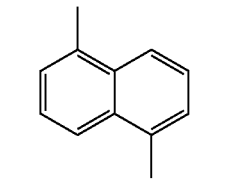 | 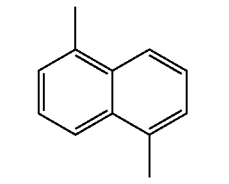 | 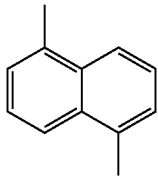 |
| 204 | 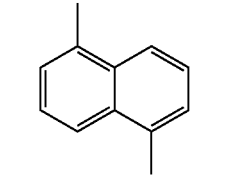 | 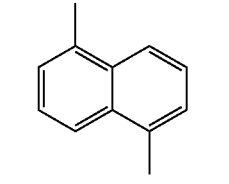 | 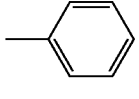 |
| 205 | 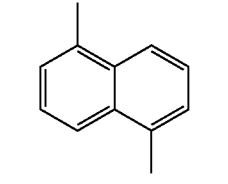 | 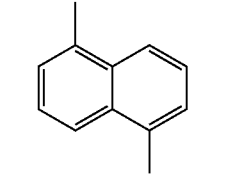 | 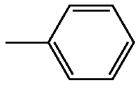 |
| 206 | 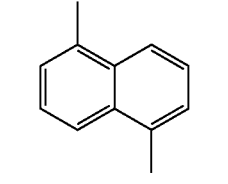 | 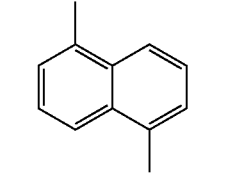 | 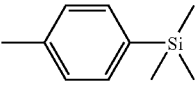 |
| 207 | 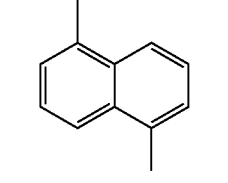 | 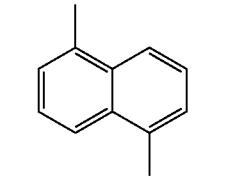 | 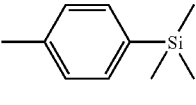 |

TABLE 1-continued
| | 215 | | 216 |
|---|---|---|---|
| 208 | 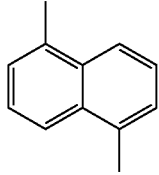 | 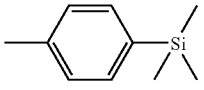 | 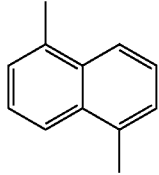 |
| 209 | 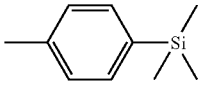 | 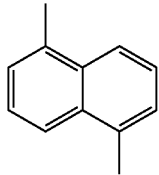 | 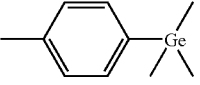 |
| 210 | 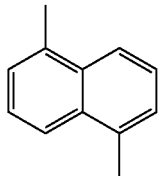 | 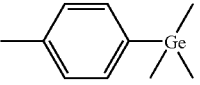 | 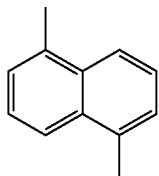 |
| 211 | 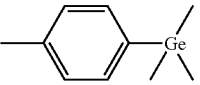 | 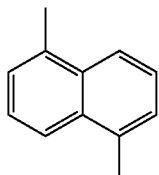 | 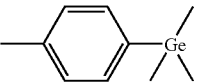 |
| 212 | 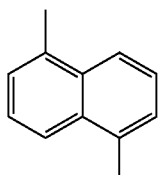 | 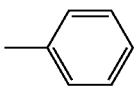 | 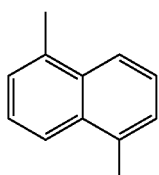 |
| 213 | 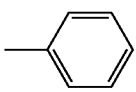 | | |

TABLE 1-continued
| | 217 | | 218 |
|---|---|---|---|
| 216 | 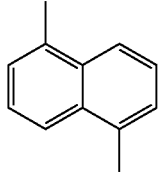 | 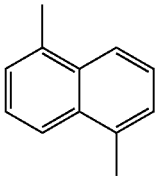 | 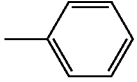 |
| 217 | 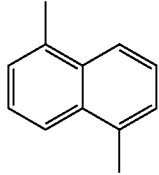 | 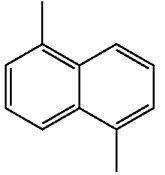 | 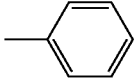 |
| 218 | 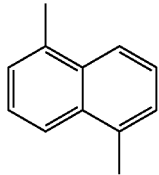 | 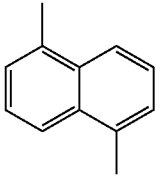 | 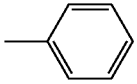 |
| 219 | 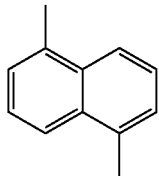 | 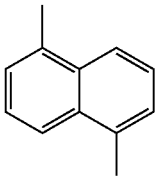 | 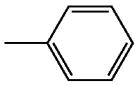 |
| 220 | 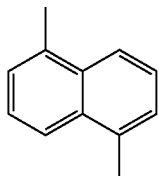 | 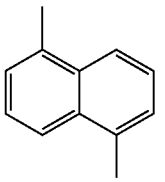 | 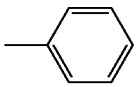 |
| 221 | 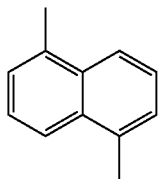 | 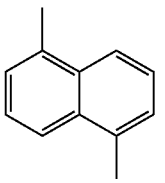 | 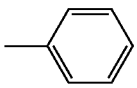 |
| 222 | 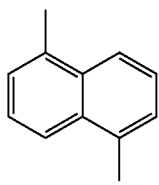 | 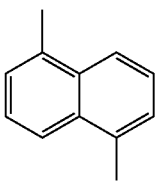 | 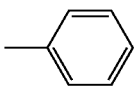 |
| 223 | 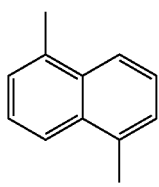 | 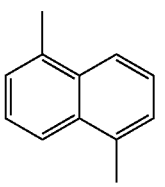 | 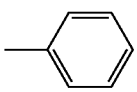 |

TABLE 1-continued
| | 219 | | 220 |
|---|---|---|---|
| 224 | 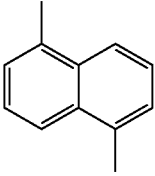 | 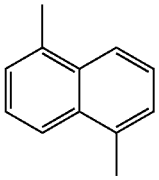 | 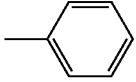 |
| 225 | 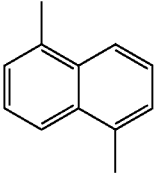 | 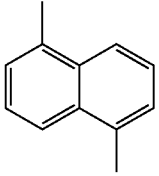 | 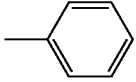 |
| 226 | 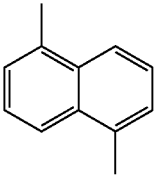 | 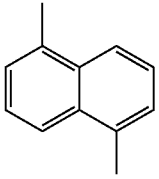 | 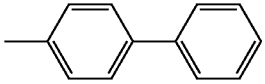 |
| 227 | 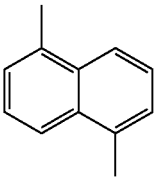 | 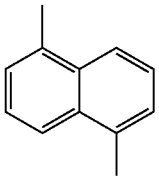 | 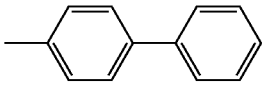 |
| 228 | 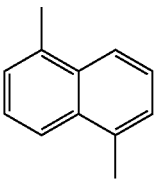 | 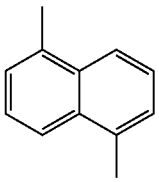 | 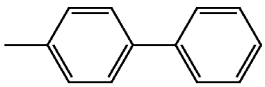 |
| 229 | 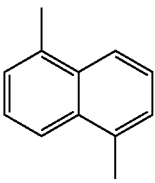 | 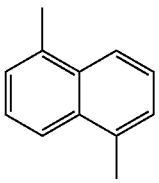 | 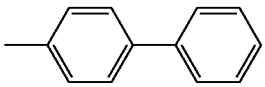 |
| 230 | 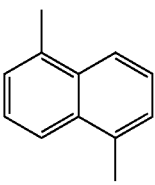 | 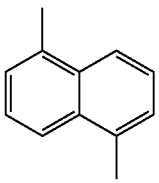 | 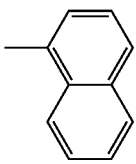 |
| 231 | 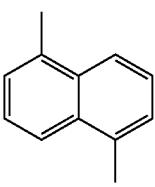 | 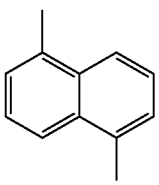 | 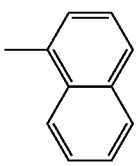 |

TABLE 1-continued
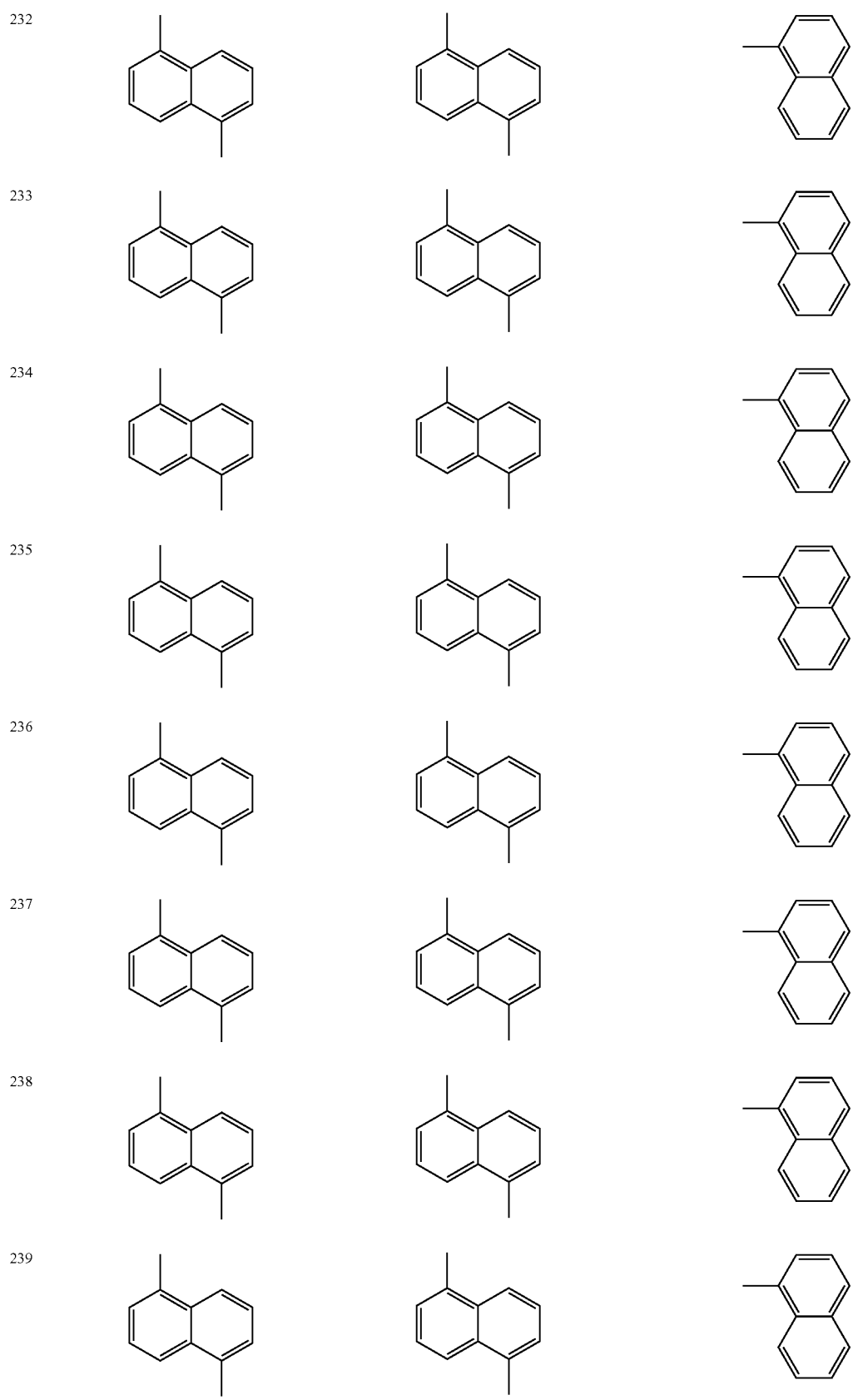

TABLE 1-continued
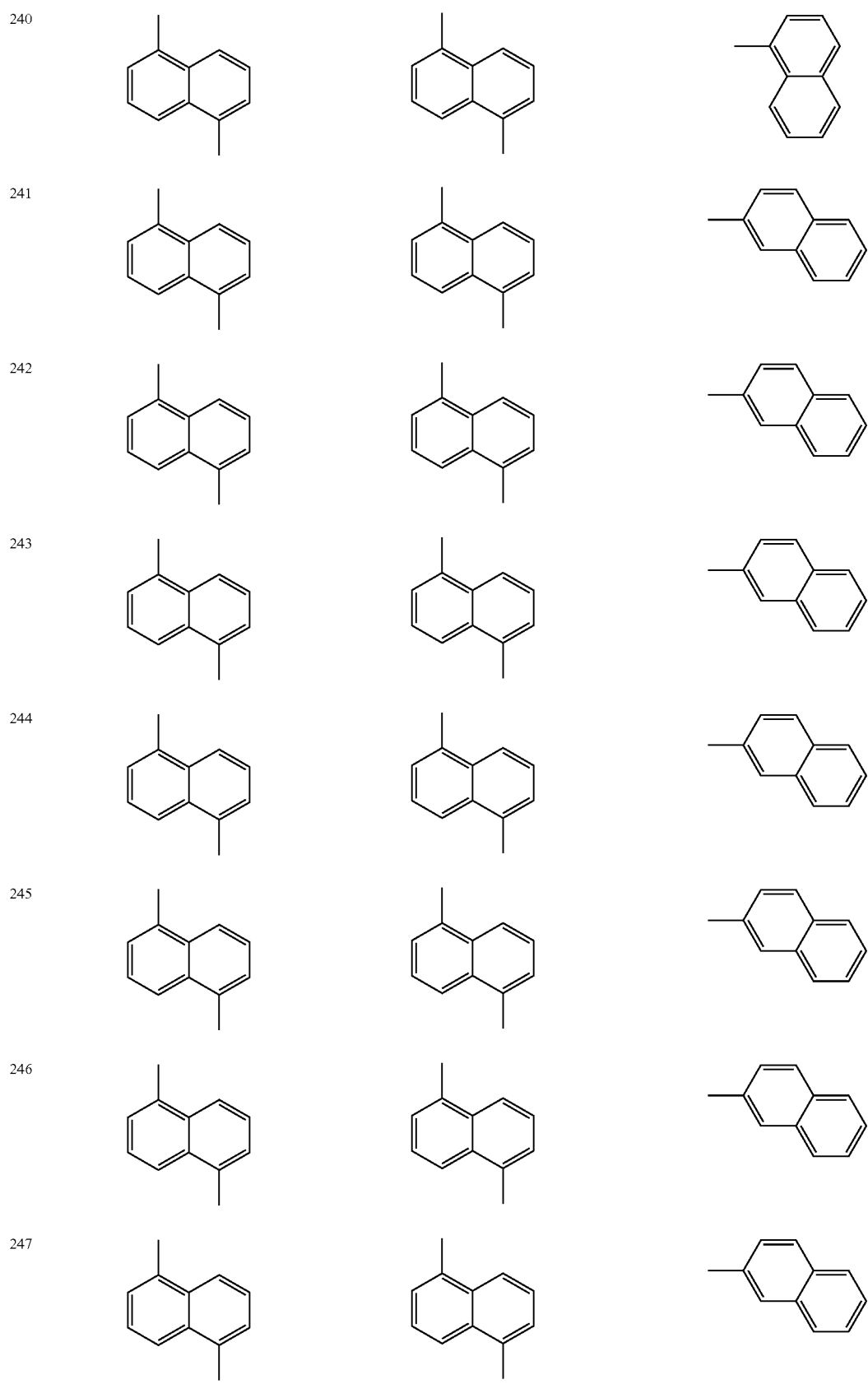

TABLE 1-continued
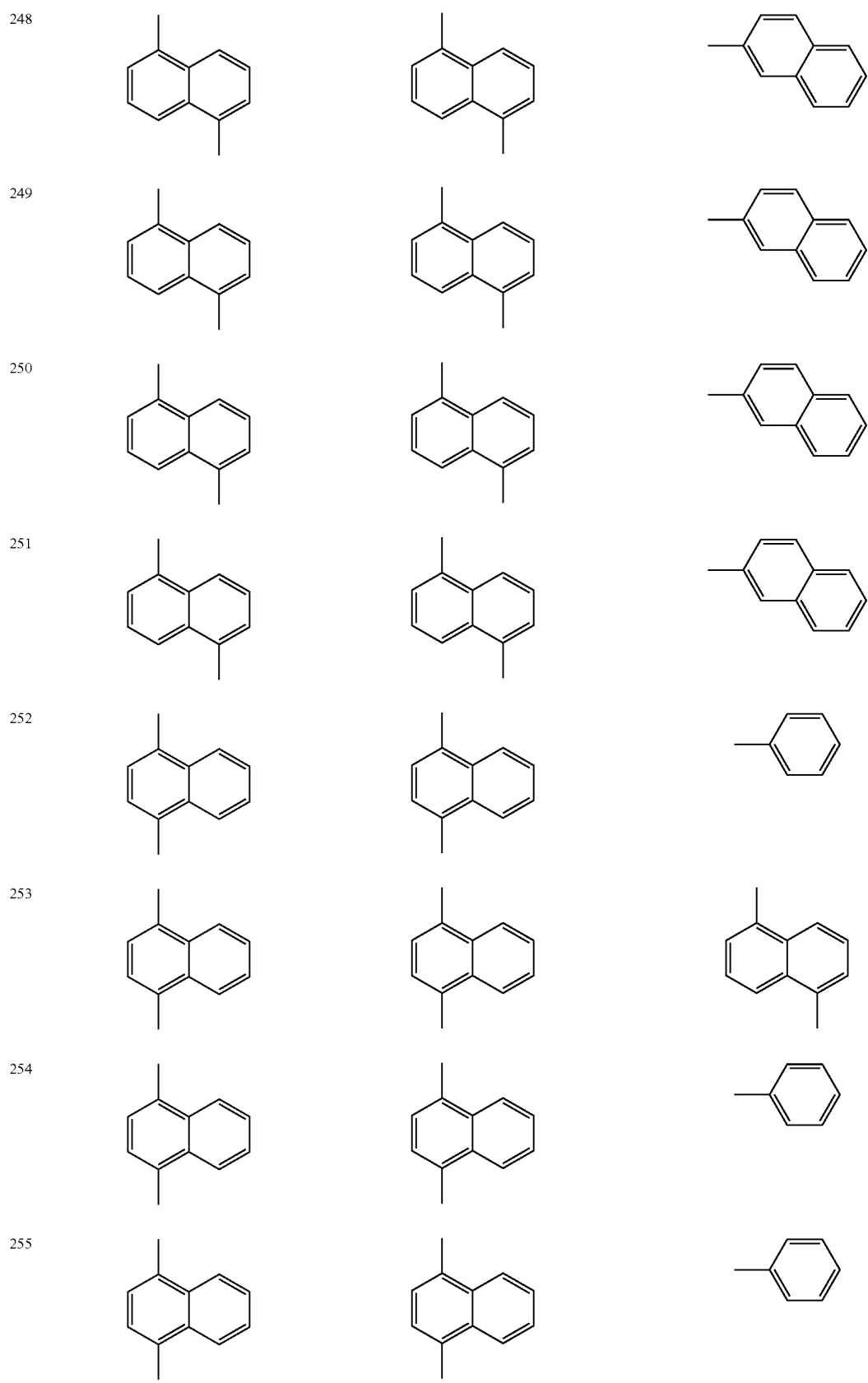

TABLE 1-continued
| | 227 | | 228 |
|---|---|---|---|
| 256 | 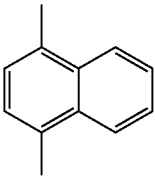 | 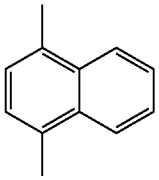 | 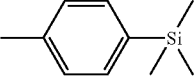 |
| 257 | 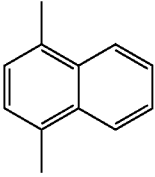 | 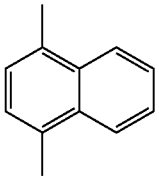 | 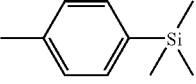 |
| 258 | 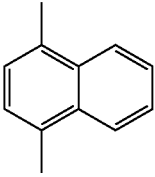 | 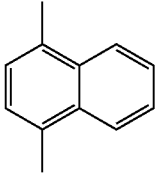 | 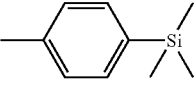 |
| 259 | 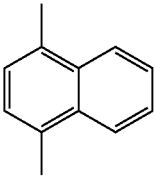 | 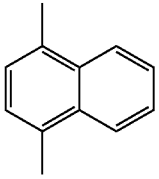 | 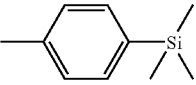 |
| 260 | 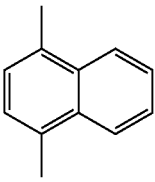 | 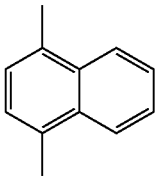 | 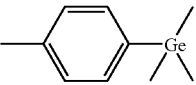 |
| 261 | 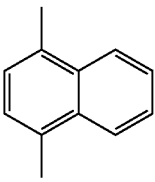 | 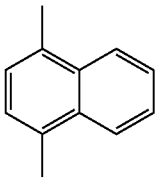 | 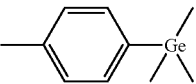 |
| 262 | 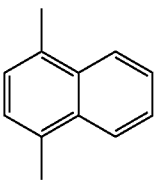 | 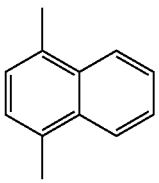 | 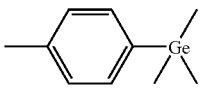 |
| 263 | 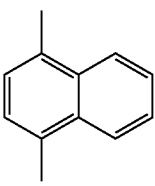 | 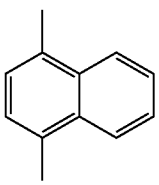 | 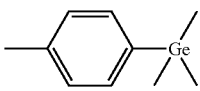 |

TABLE 1-continued
| | | | |
|---|---|---|---|
| 264 | 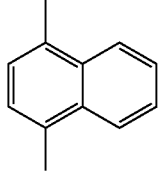 | 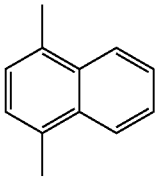 | 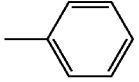 |
| 265 | 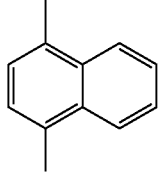 | 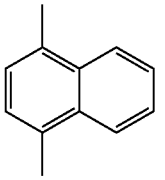 | 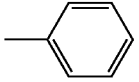 |
| 266 | 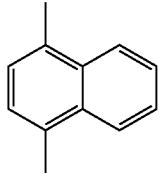 | 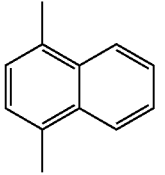 | 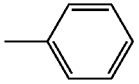 |
| 267 | 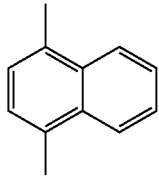 | 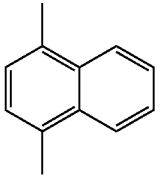 | 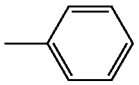 |
| 268 | 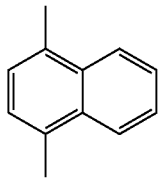 | 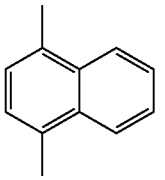 | 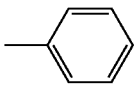 |
| 269 | 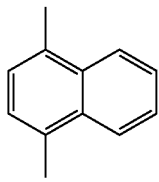 | 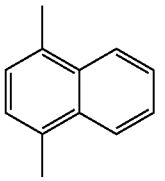 | 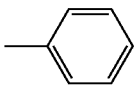 |
| 270 | 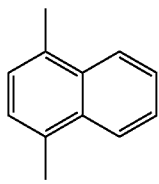 | 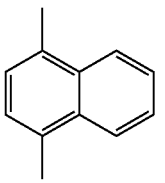 | 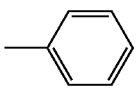 |
| 271 | 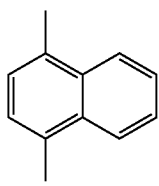 | 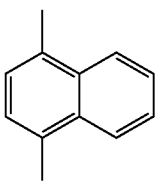 | 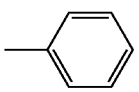 |

TABLE 1-continued
| | 231 | | 232 |
|---|---|---|---|
| 272 | 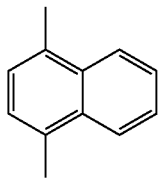 | 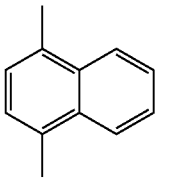 | 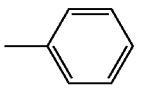 |
| 273 | 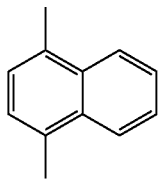 | 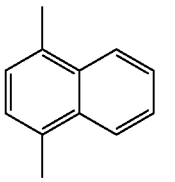 | 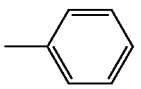 |
| 274 | 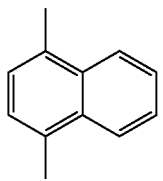 | 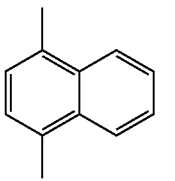 | 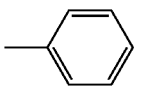 |
| 275 | 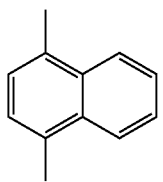 | 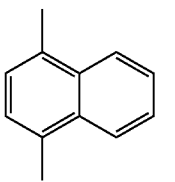 | 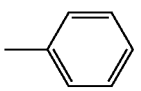 |
| 276 | 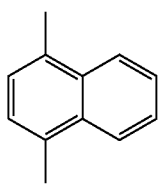 | 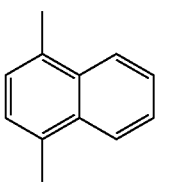 | 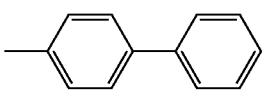 |
| 277 | 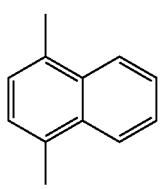 | 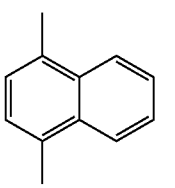 | 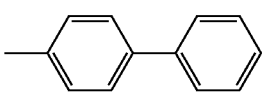 |
| 278 | 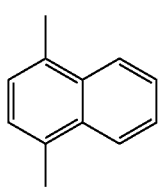 | 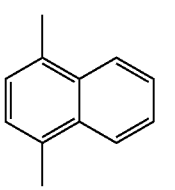 | 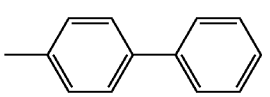 |
| 279 | 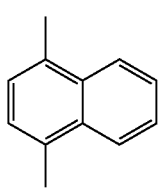 | 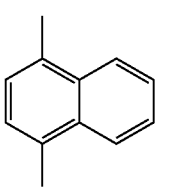 | 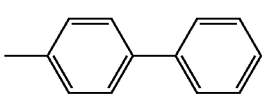 |

TABLE 1-continued
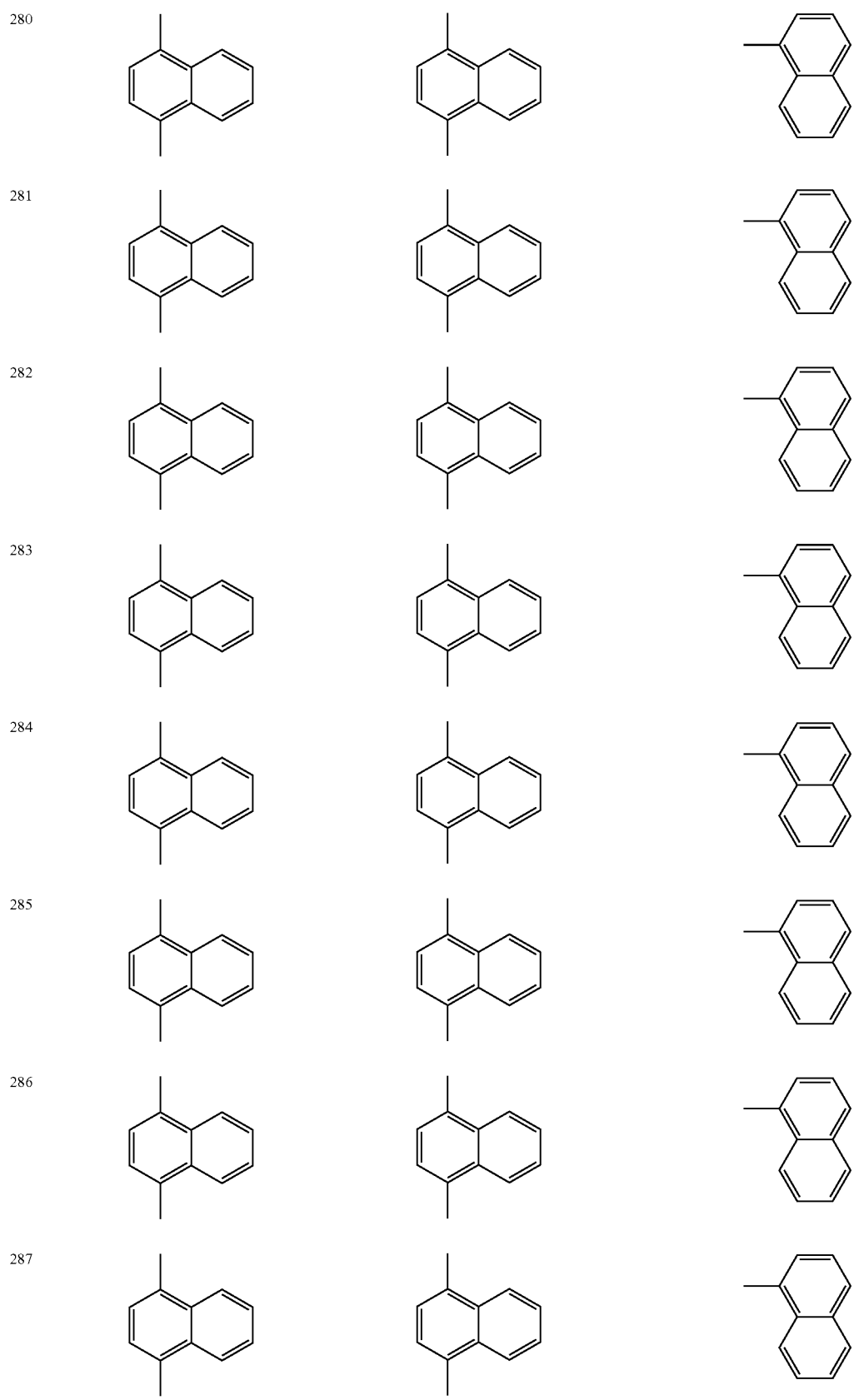

TABLE 1-continued
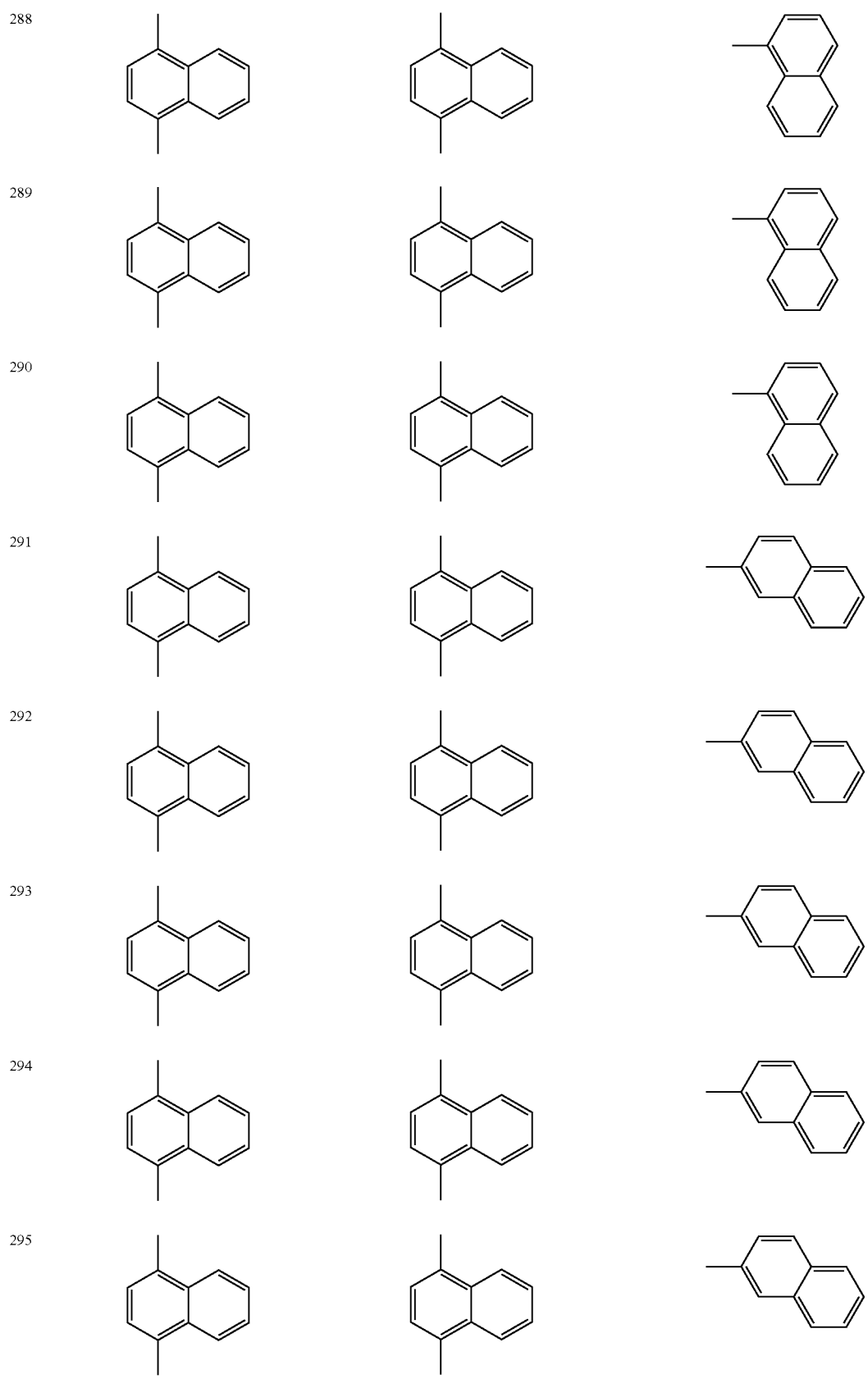

TABLE 1-continued
| | 237 | | 238 |
|---|---|---|---|
| 296 | 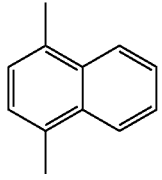 | 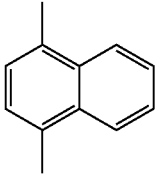 | 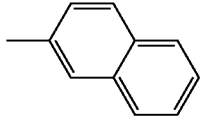 |
| 297 | 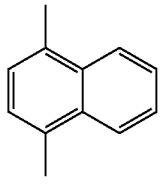 | 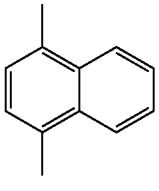 | 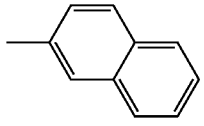 |
| 298 | 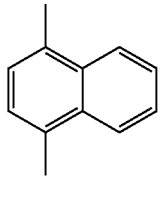 | 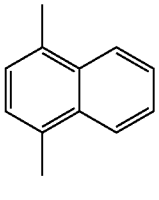 | 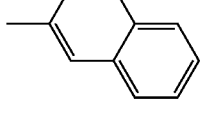 |
| 299 | 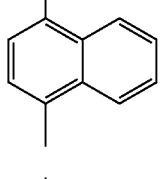 | 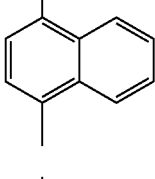 | 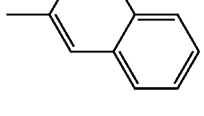 |
| 300 | 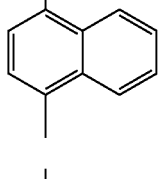 | 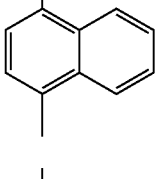 | 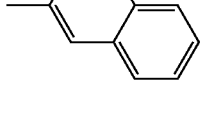 |
| 301 | 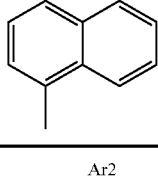 | 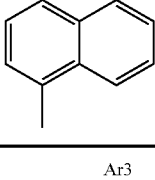 | 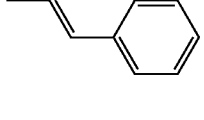 |
| | Ar2 | Ar3 | Ar4 |
|---|---|---|---|
| 49 | 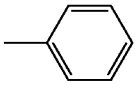 | 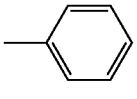 | 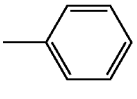 |
| 50 | 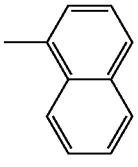 | 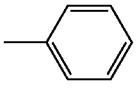 | 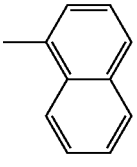 |
| 51 | 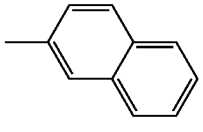 | 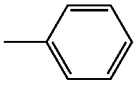 | 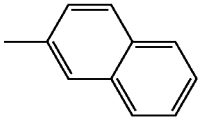 |

TABLE 1-continued
| | | | |
|---|---|---|---|
| 52 | 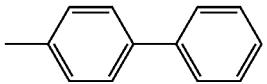 | 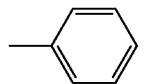 | 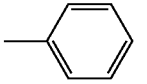 |
| 53 | 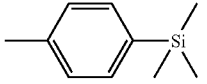 | 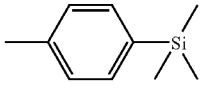 | 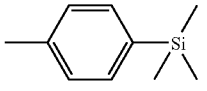 |
| 54 | 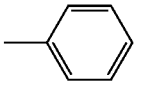 | 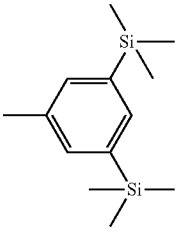 | 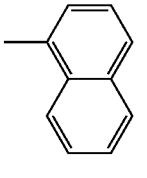 |
| 55 | 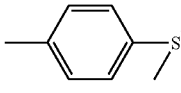 | 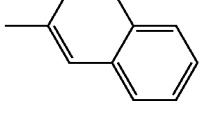 | 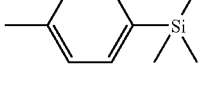 |
| 56 | 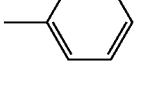 | 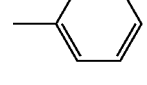 | 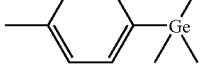 |
| 57 | 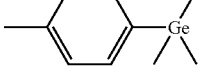 | 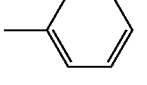 | 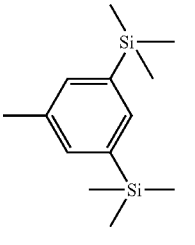 |
| 58 | 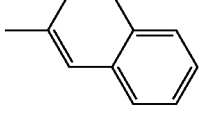 | 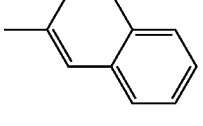 | 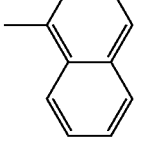 |
| 59 | 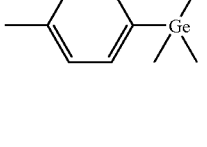 | | |
| 60 | | | |
| 61 | | | |
| 62 | | | |

TABLE 1-continued
| | 241 | | 242 |
|---|---|---|---|
| 63 | 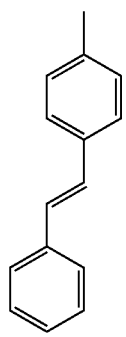 | 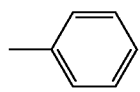 | 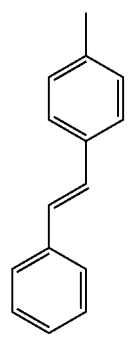 |
| 64 | 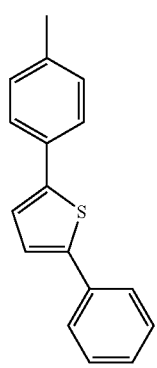 | 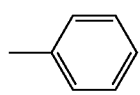 | 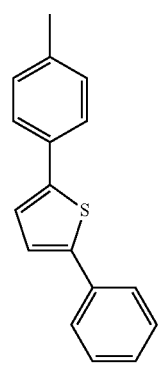 |
| 65 | 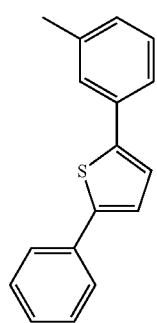 | 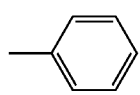 | 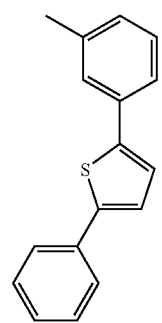 |
| 66 | 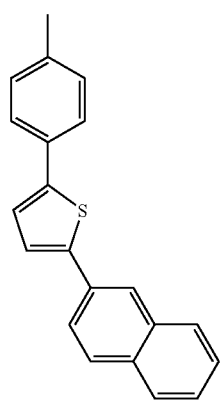 | 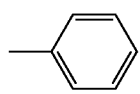 | 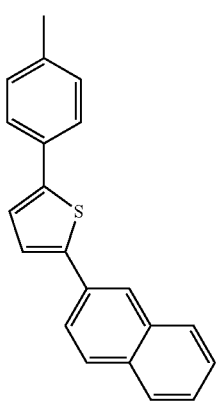 |

TABLE 1-continued

| | | | |
|---|---|---|---|
| 67 | (4-methylphenyl-thiophene-naphthyl) | phenyl | (4-methylphenyl-thiophene-naphthyl) |
| 68 | methylpyrene | phenyl | methylpyrene |
| 69 | methylanthracene | phenyl | methylanthracene |
| 70 | methylperylene | phenyl | methylperylene |
| 71 | methylanthracene (2-substituted) | phenyl | methylanthracene (2-substituted) |
| 72 | 4-methylphenyl-diphenylamine | phenyl | 4-methylphenyl-diphenylamine |
| 73 | 4-methylphenyl-phenyl-naphthyl-amine | phenyl | 4-methylphenyl-phenyl-naphthyl-amine |

TABLE 1-continued
| 74 | 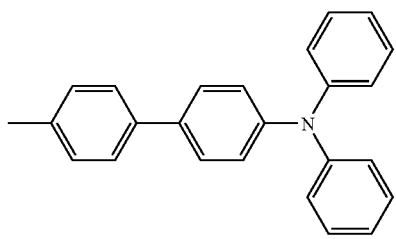 | 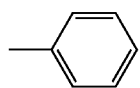 | 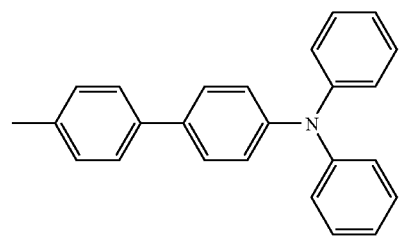 |
| 75 | 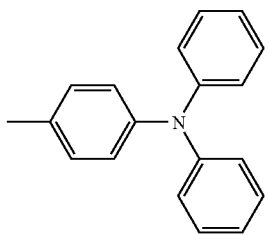 | 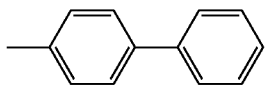 | 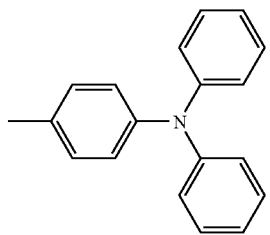 |
| 76 | 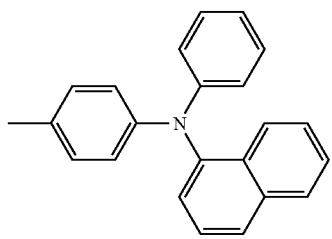 | 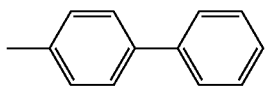 | 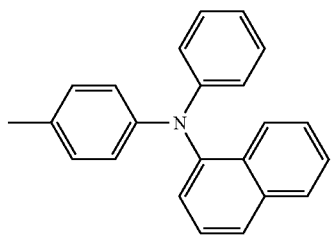 |
| 77 | 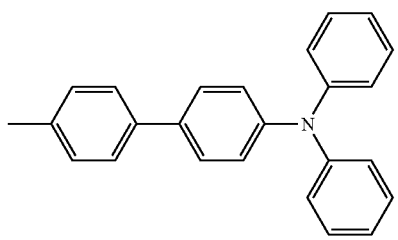 | 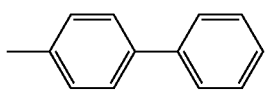 | 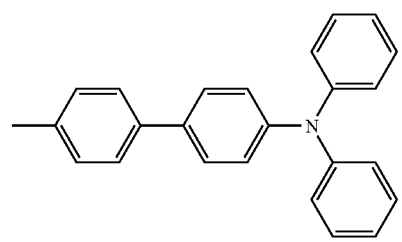 |
| 78 | 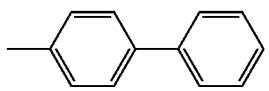 | 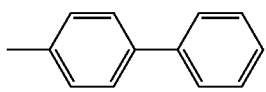 | 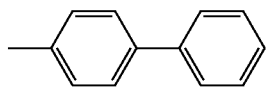 |
| 79 | 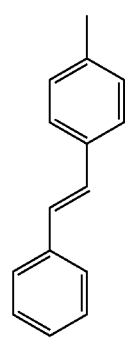 | 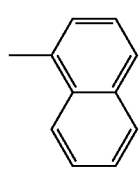 | 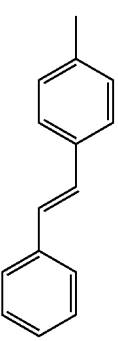 |

TABLE 1-continued
| | | | |
|---|---|---|---|
| 80 | 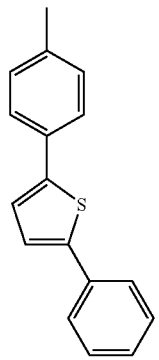 | 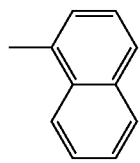 | 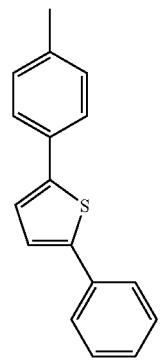 |
| 81 | 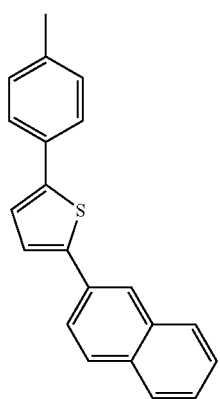 | 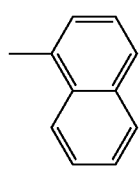 | 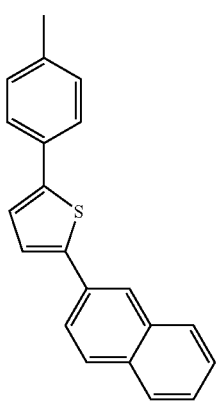 |
| 82 | 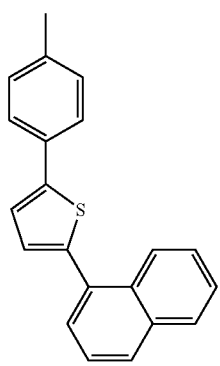 | 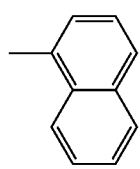 | 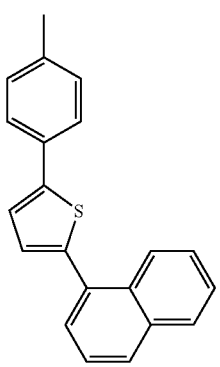 |
| 83 | 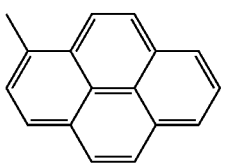 | 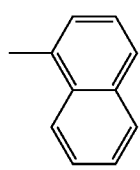 | 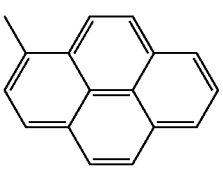 |
| 84 | 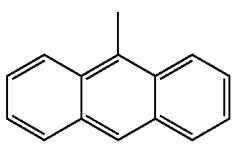 | 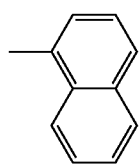 | 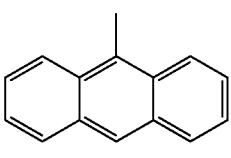 |

TABLE 1-continued
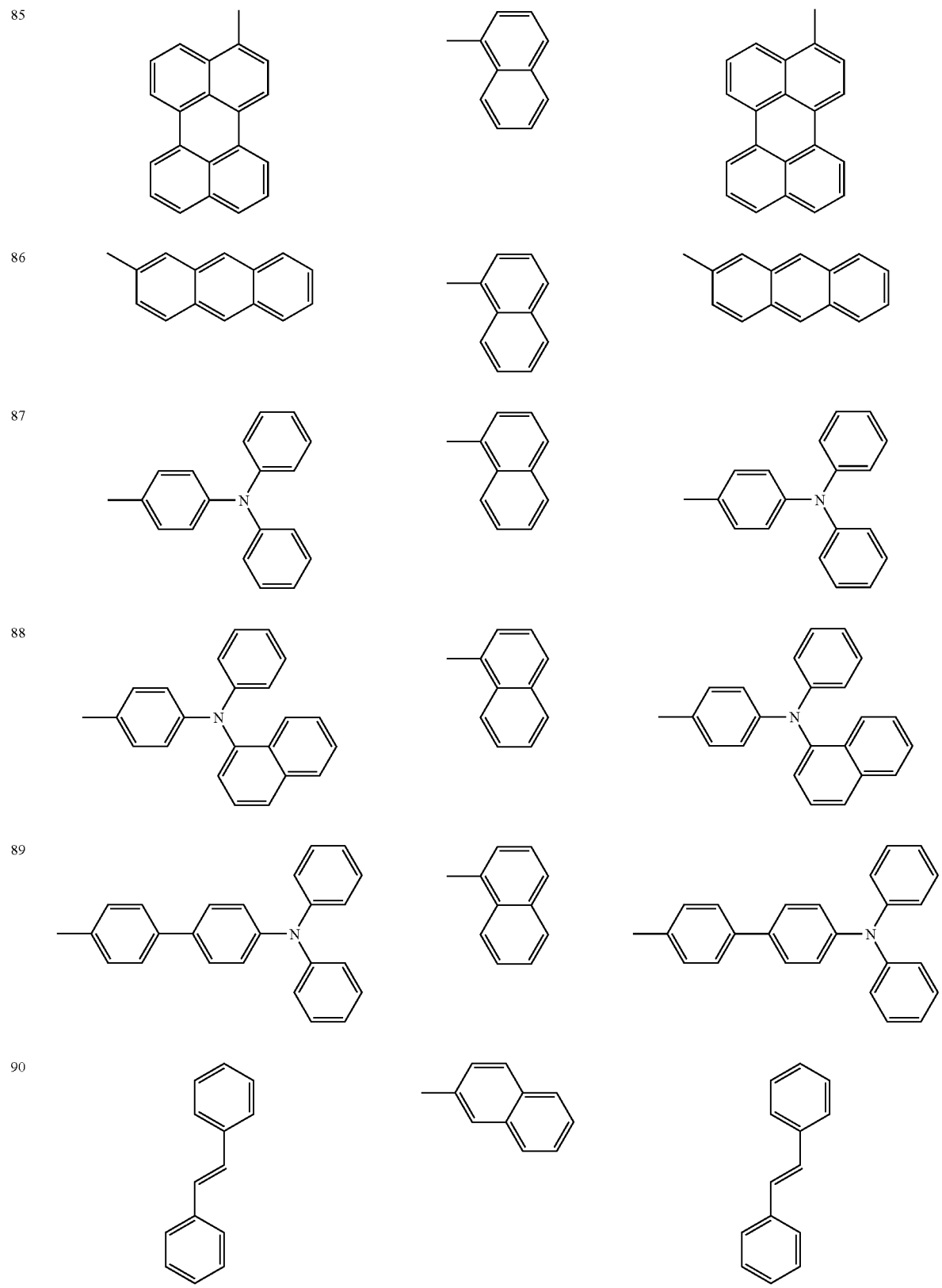

US 8,026,514 B2
TABLE 1-continued
| | 251 | | 252 |
|---|---|---|---|
| 91 | 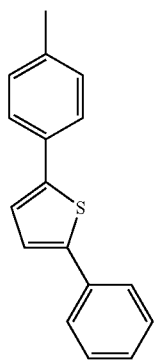 | 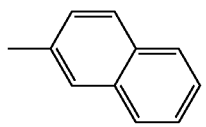 | 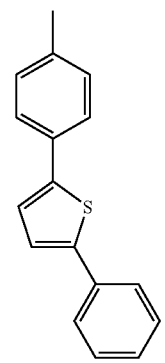 |
| 92 | 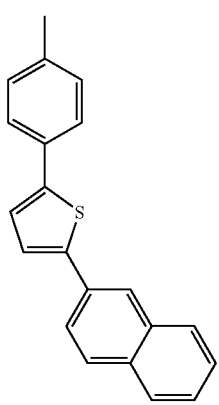 | 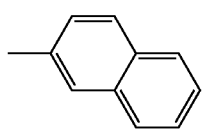 | 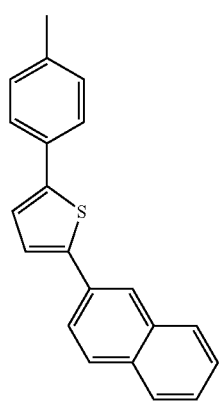 |
| 93 | 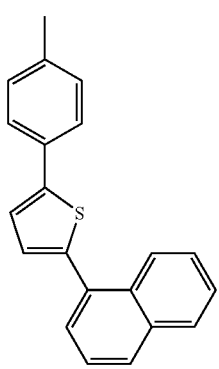 | 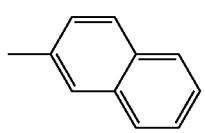 | 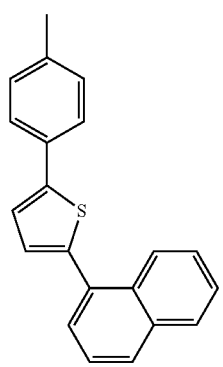 |
| 94 | 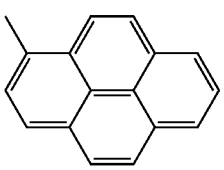 | 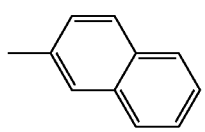 | 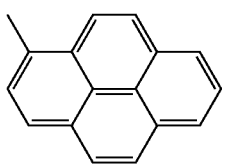 |
| 95 | 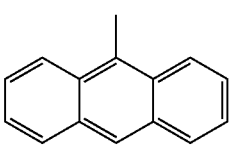 | 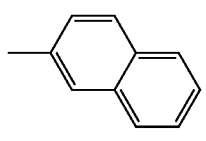 | 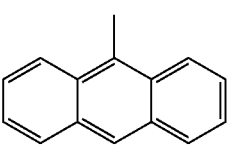 |

TABLE 1-continued
| | | | |
|---|---|---|---|
| 96 | 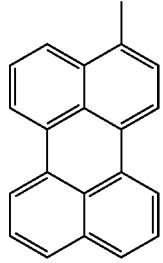 | 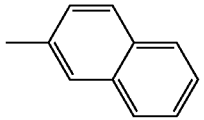 | 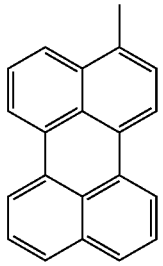 |
| 97 | 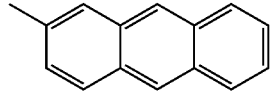 | 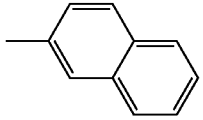 | 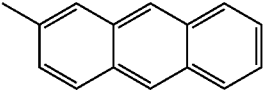 |
| 98 | 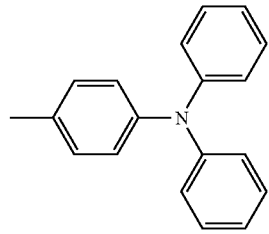 | 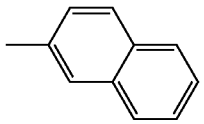 | 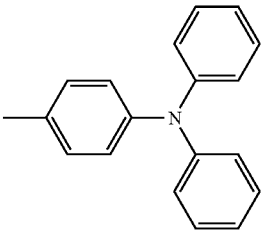 |
| 99 | 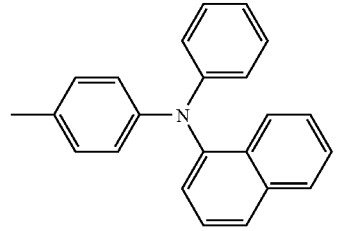 | 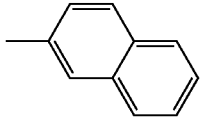 | 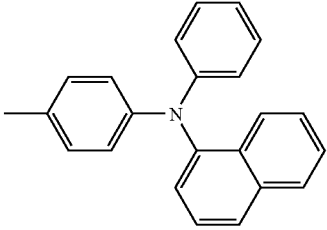 |
| 100 | 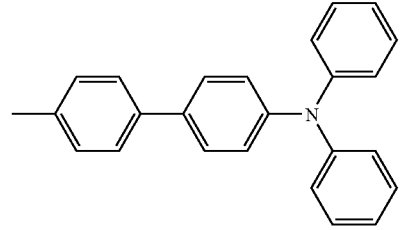 | 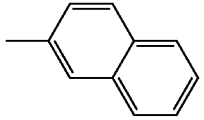 | 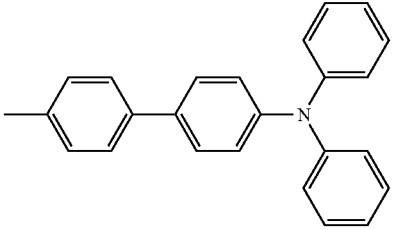 |
| 101 | 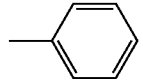 | 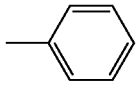 | 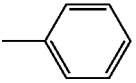 |
| 102 | 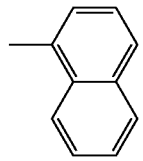 | 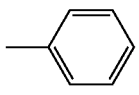 | 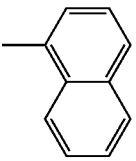 |
| 103 | 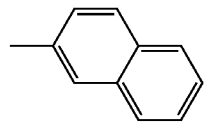 | 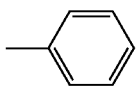 | 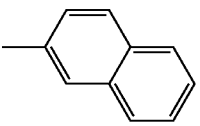 |
| 104 | 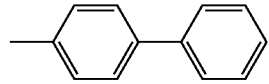 | 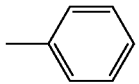 | 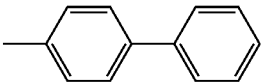 |

US 8,026,514 B2
TABLE 1-continued
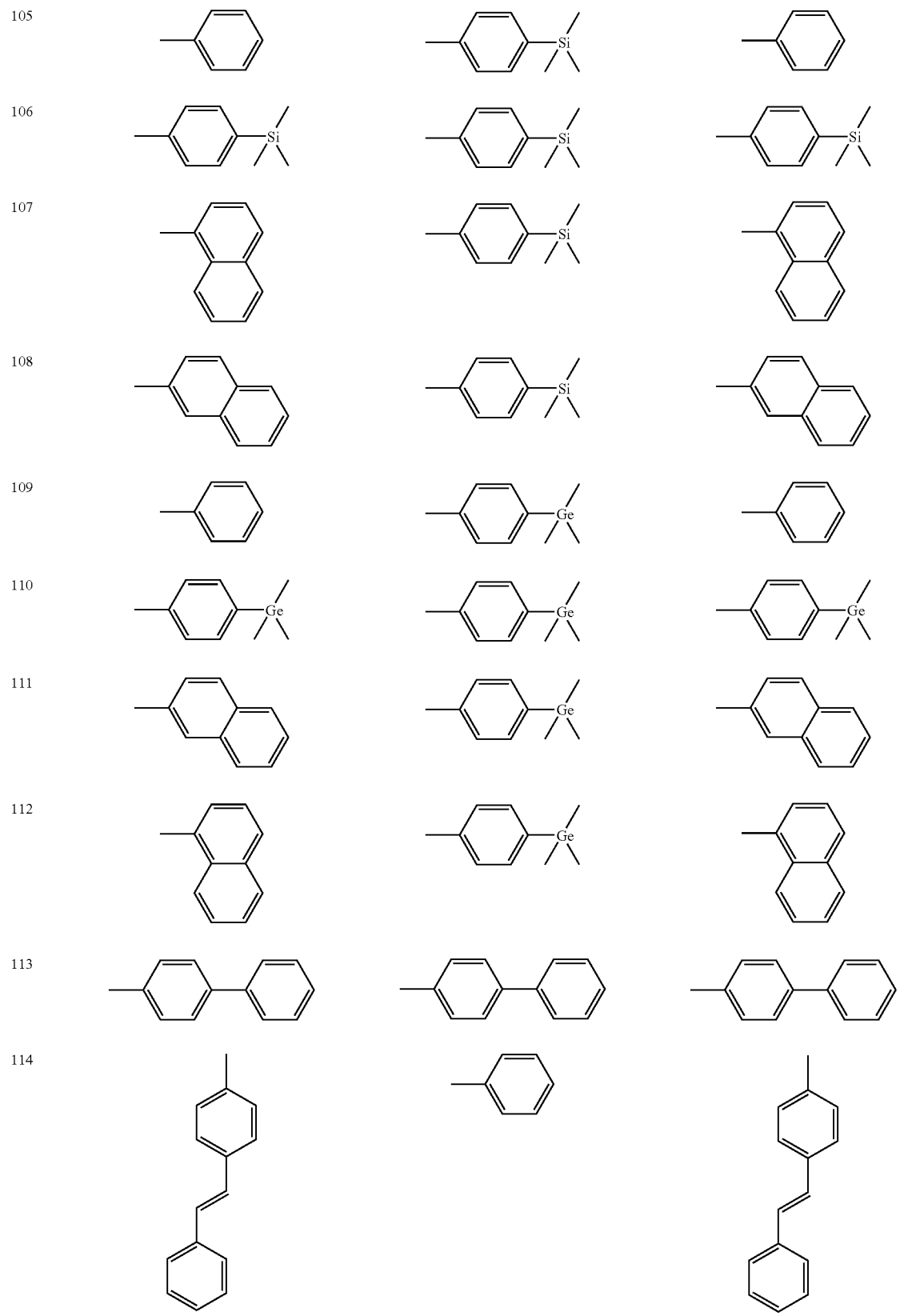

TABLE 1-continued
| | 257 | | 258 |
|---|---|---|---|
| 115 | 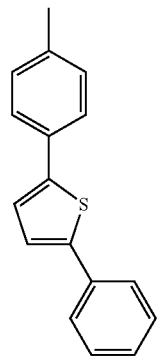 | 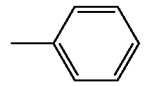 | 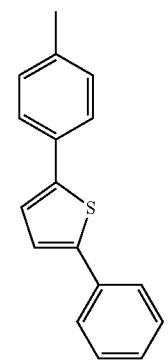 |
| 116 | 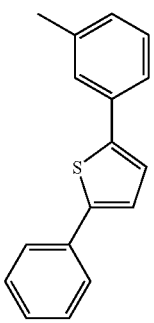 | 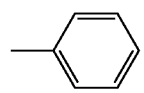 | 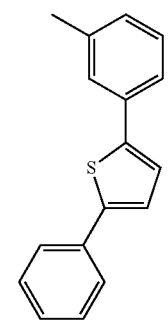 |
| 117 | 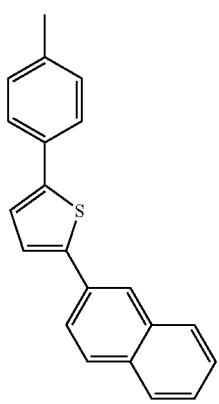 | 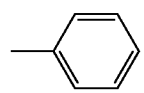 | 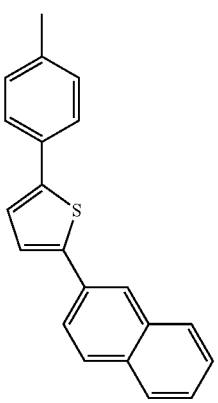 |
| 118 | 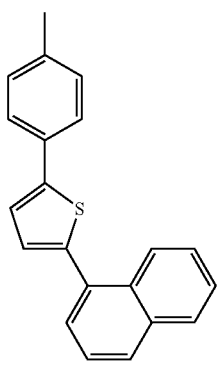 | 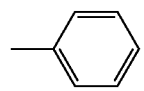 | 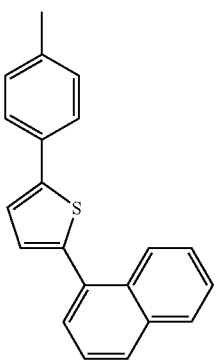 |
| 119 | 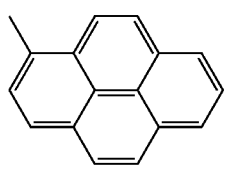 | 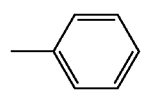 | 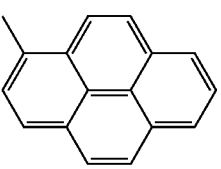 |

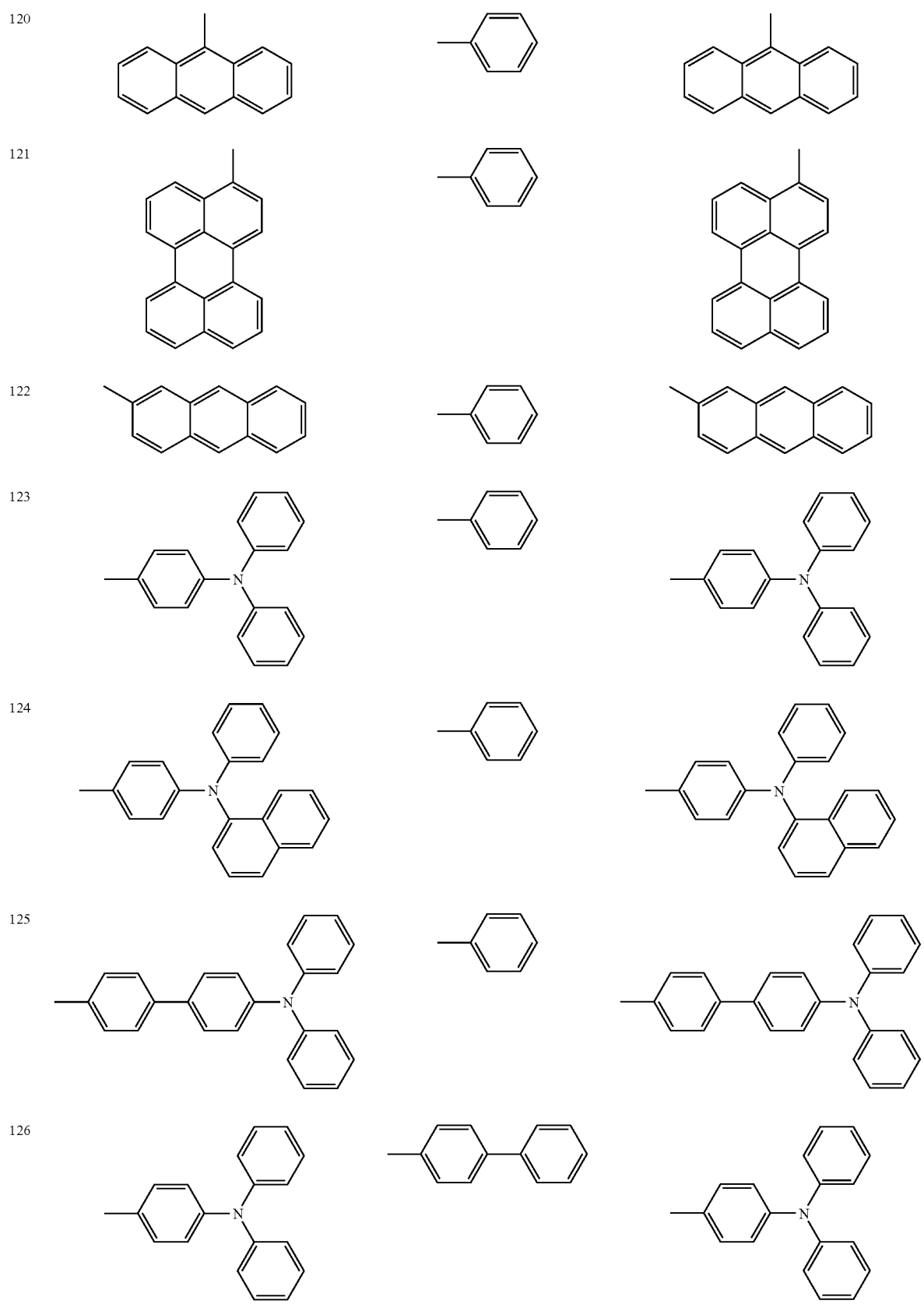

US 8,026,514 B2
TABLE 1-continued
| | 261 | | 262 |
|---|---|---|---|
| 127 | 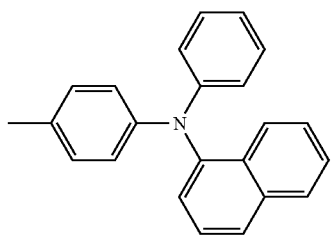 | 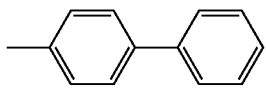 | 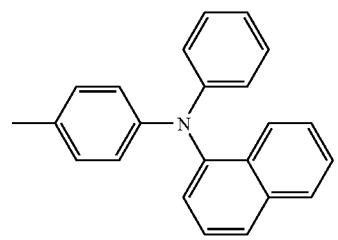 |
| 128 | 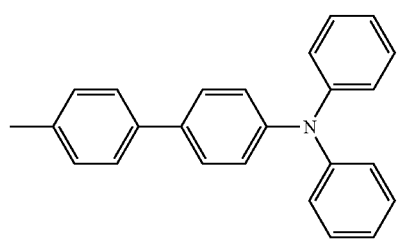 | 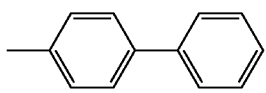 | 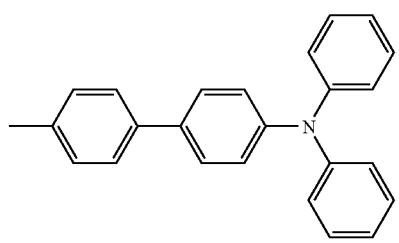 |
| 129 | 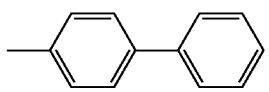 | 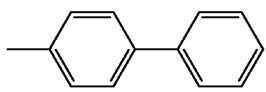 | 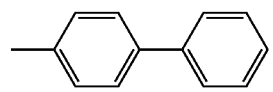 |
| 130 | 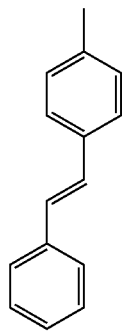 | 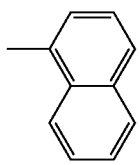 | 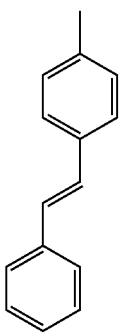 |
| 131 | 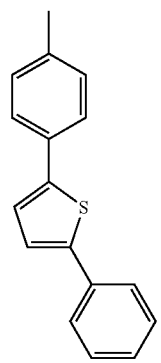 | 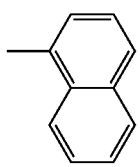 | 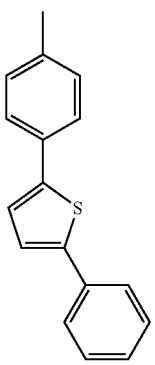 |

TABLE 1-continued
| | | | |
|---|---|---|---|
| 132 | 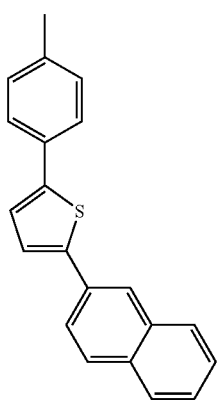 | 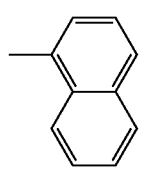 | 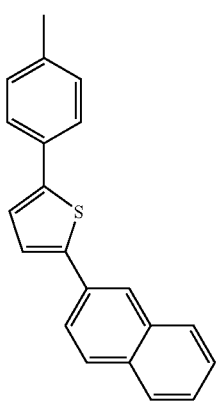 |
| 133 | 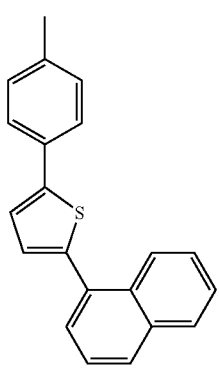 | 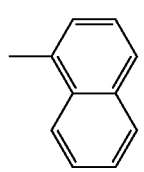 | 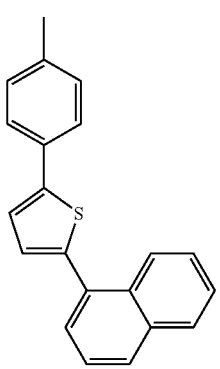 |
| 134 | 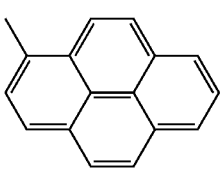 | 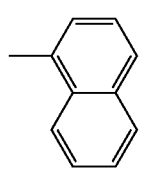 | 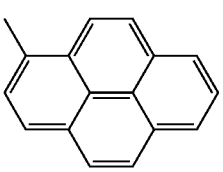 |
| 135 | 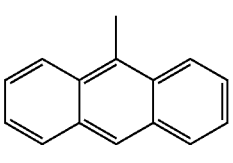 | 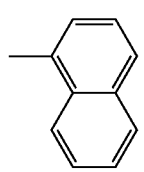 | 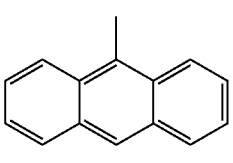 |
| 136 | 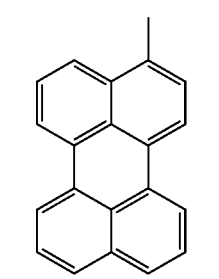 | 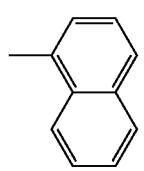 | 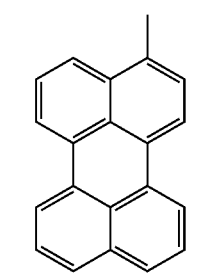 |
| 137 | 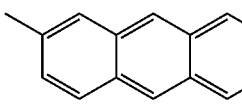 | 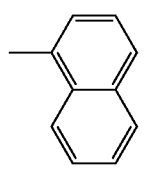 | 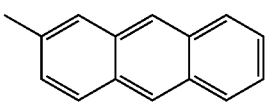 |

TABLE 1-continued
| 138 | 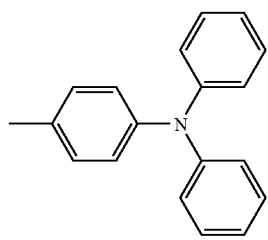 | 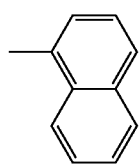 | 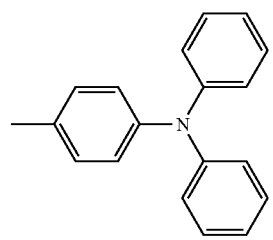 |
| 139 | 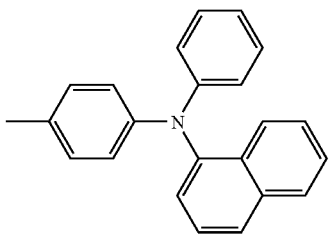 | 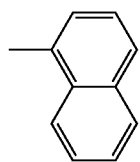 | 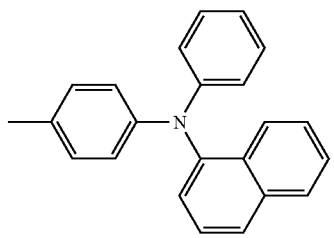 |
| 140 | 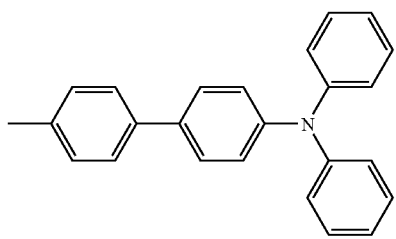 | 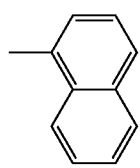 | 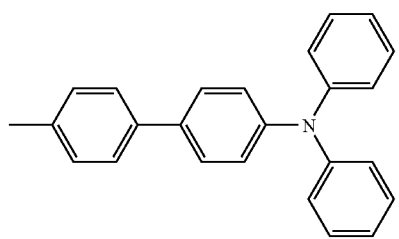 |
| 141 | 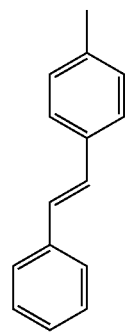 | 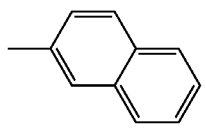 | 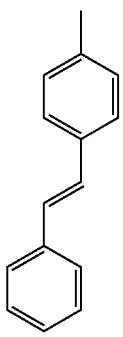 |
| 142 | 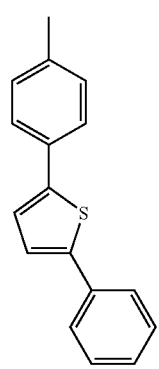 | 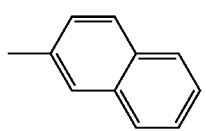 | 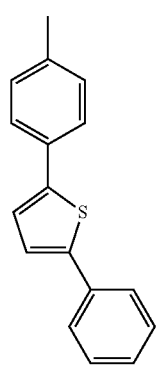 |

TABLE 1-continued
| | | | |
|---|---|---|---|
| 143 | 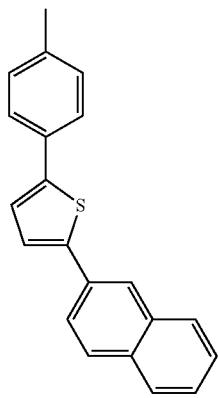 | 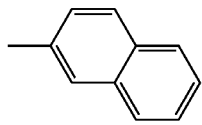 | 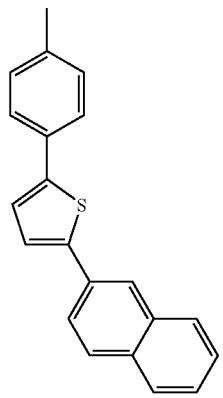 |
| 144 | 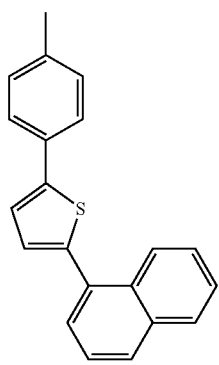 | 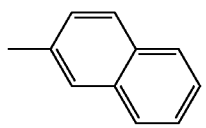 | 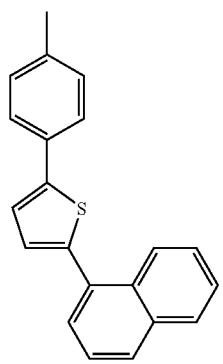 |
| 145 | 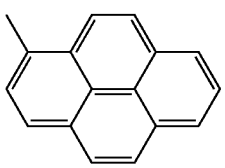 | 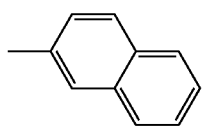 | 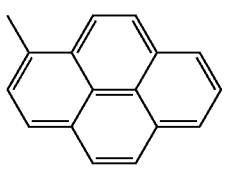 |
| 146 | 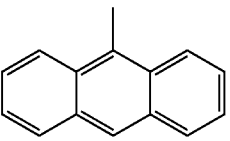 | 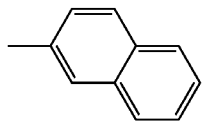 | 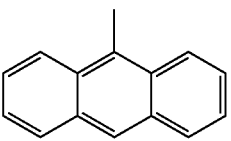 |
| 147 | 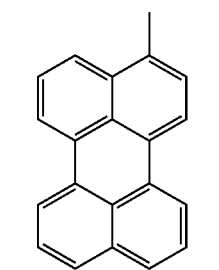 | 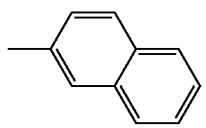 | 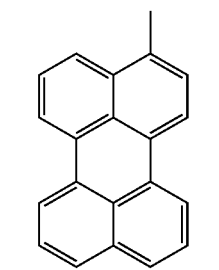 |
| 148 | 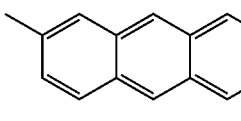 | 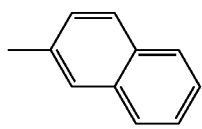 | 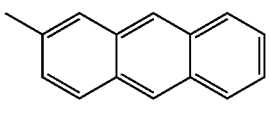 |

TABLE 1-continued
| | | | |
|---|---|---|---|
| 149 | 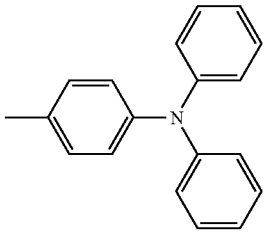 | 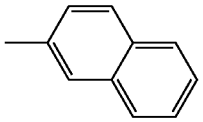 | 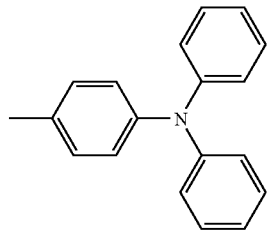 |
| 150 | 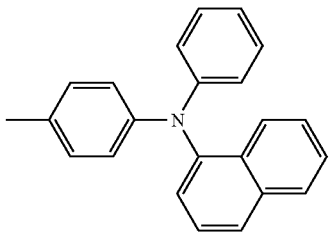 | 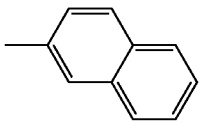 | 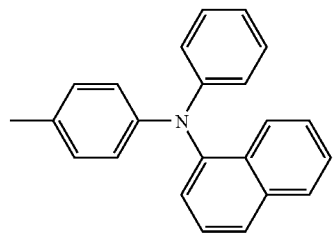 |
| 151 | 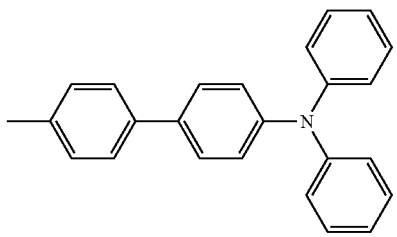 | 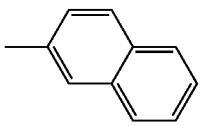 | 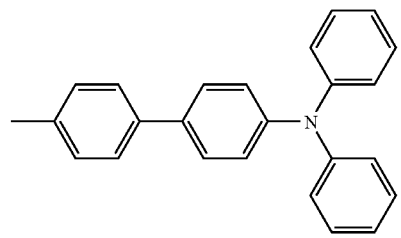 |
| 152 | 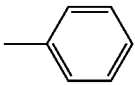 | 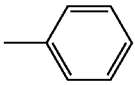 | 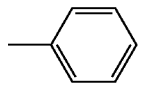 |
| 153 | 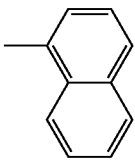 | 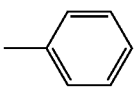 | 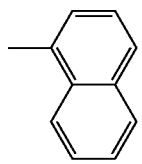 |
| 154 | 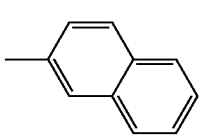 | 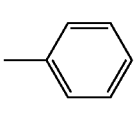 | 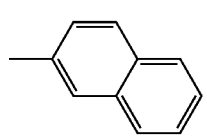 |
| 155 | 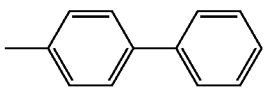 | 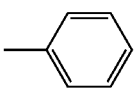 | 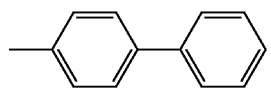 |
| 156 | 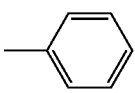 | 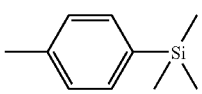 | 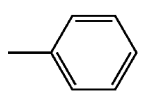 |
| 157 | 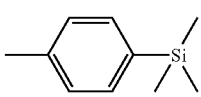 | 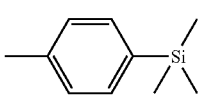 |  |
| 158 | 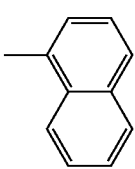 | 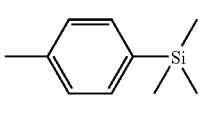 | 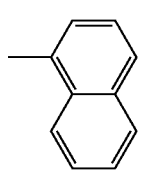 |

TABLE 1-continued
| | 271 | | 272 |
|---|---|---|---|
| 159 | 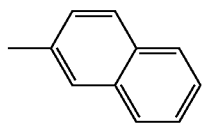 | 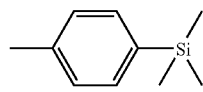 | 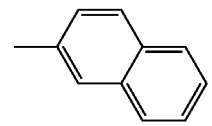 |
| 160 | 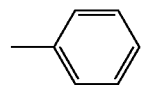 | 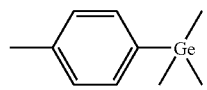 | 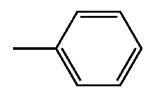 |
| 161 | 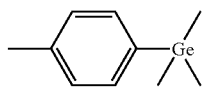 | 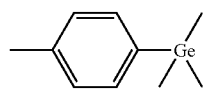 |  |
| 162 | 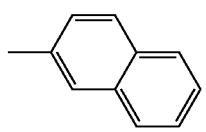 | 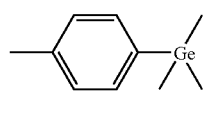 | 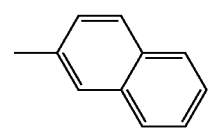 |
| 163 | 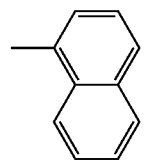 | 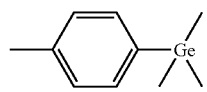 | 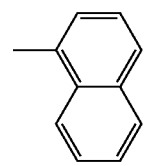 |
| 164 | 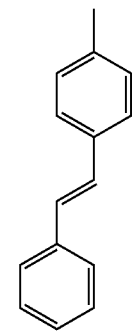 | 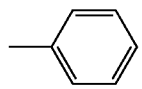 | 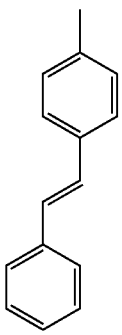 |
| 165 | 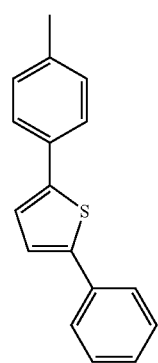 | 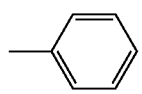 | 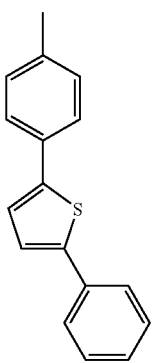 |

TABLE 1-continued
| 166 | 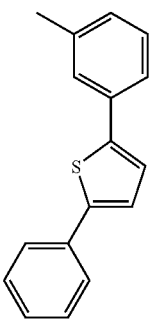 | 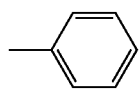 | 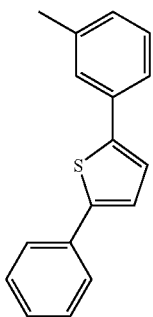 |
| 167 | 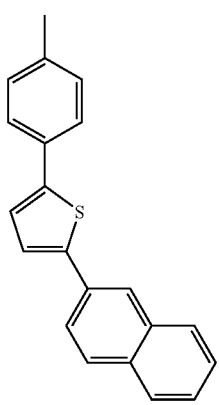 | 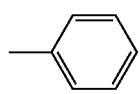 | 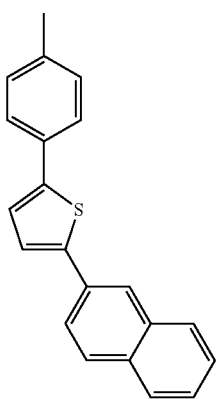 |
| 168 | 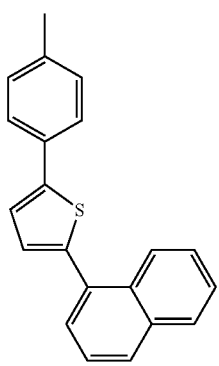 | 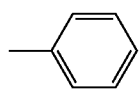 | 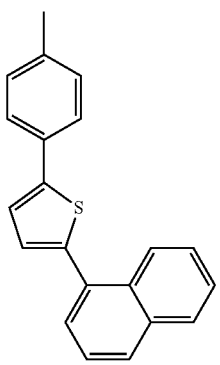 |
| 169 | 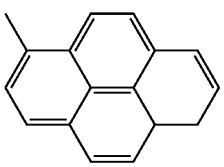 | 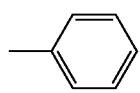 | 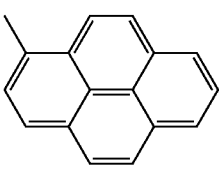 |
| 170 | 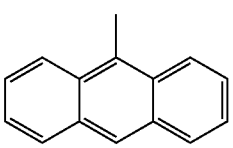 | 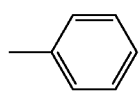 | 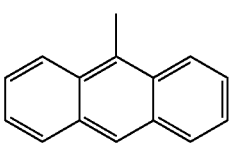 |

TABLE 1-continued
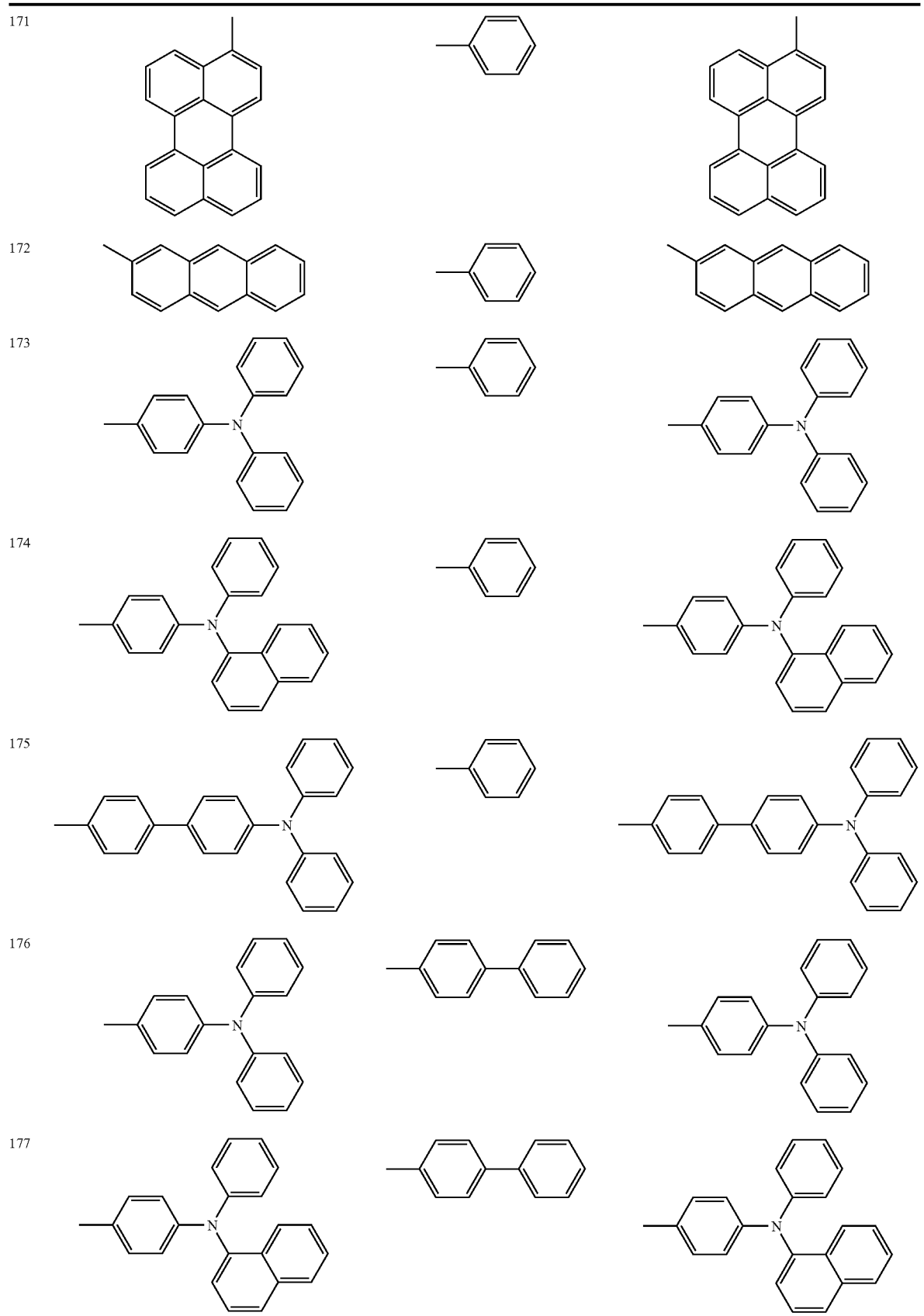

TABLE 1-continued
| | | | |
|---|---|---|---|
| 178 | 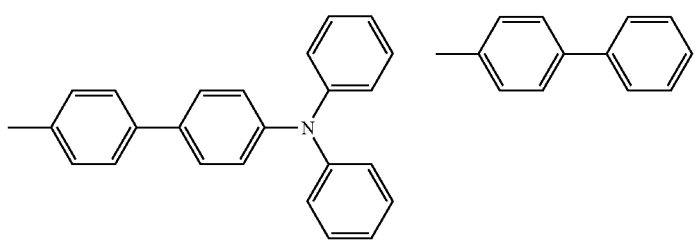 | 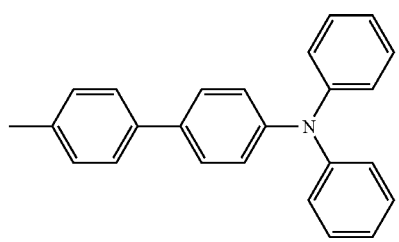 | 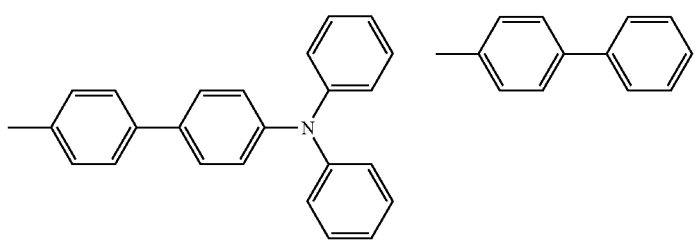 |
| 179 |  |  |  |
| 180 | 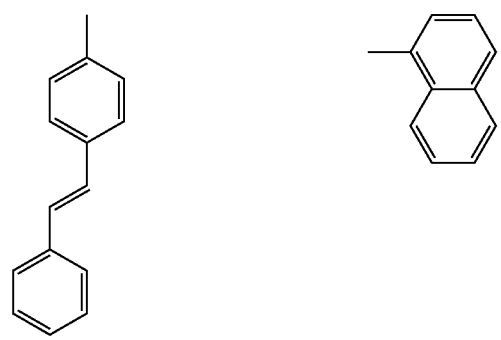 | 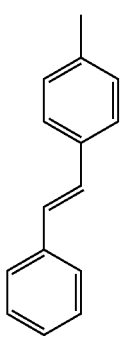 | 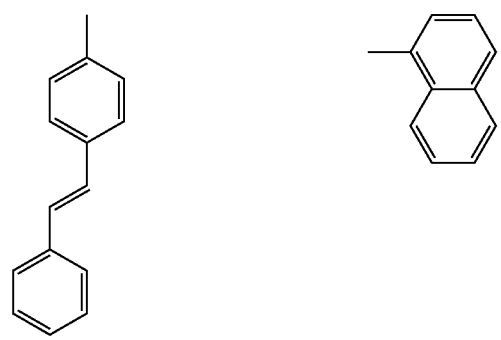 |
| 181 | 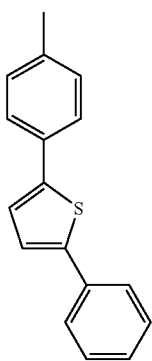 | 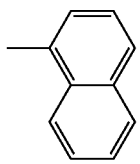 | 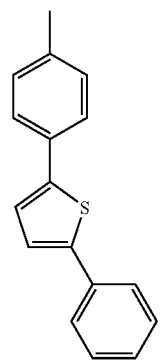 |
| 182 | 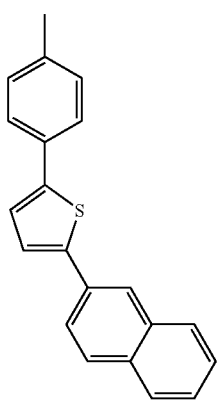 | 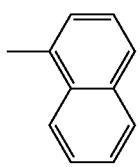 | 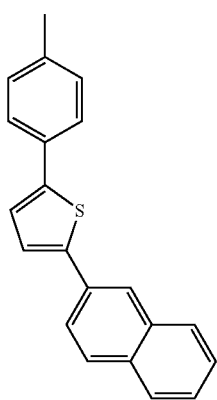 |

TABLE 1-continued

| | | | |
|---|---|---|---|
| 183 | | | |
| 184 | | | |
| 185 | | | |
| 186 | | | |
| 187 | | | |
| 188 | | | |
| 189 | | | |

US 8,026,514 B2
TABLE 1-continued
| 190 | 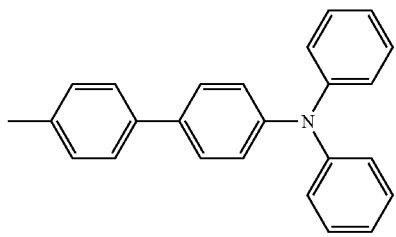 | 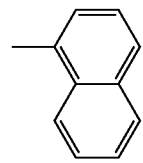 | 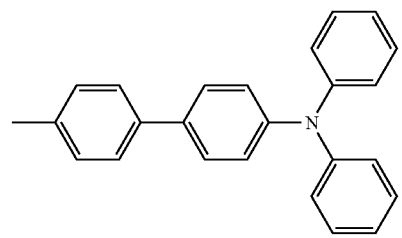 |
| --- | --- | --- | --- |
| 191 | 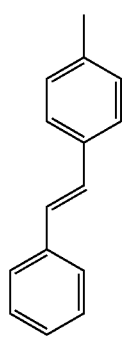 | 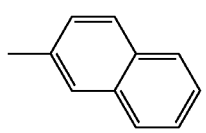 | 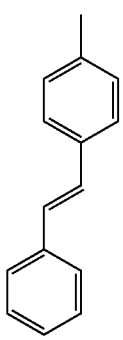 |
| 192 | 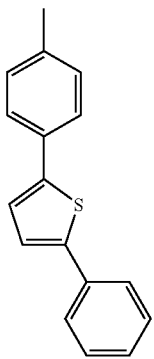 | 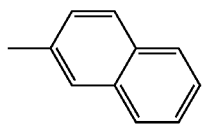 | 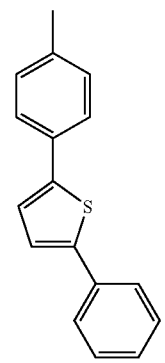 |
| 193 | 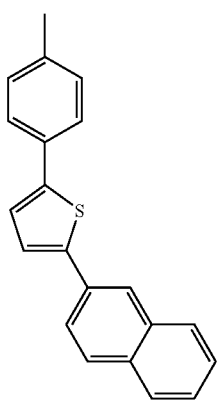 | 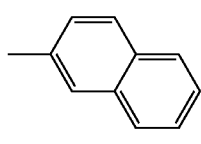 | 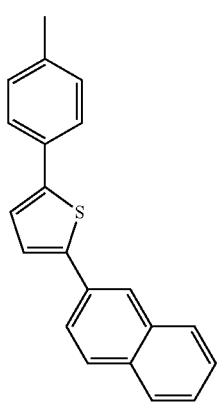 |

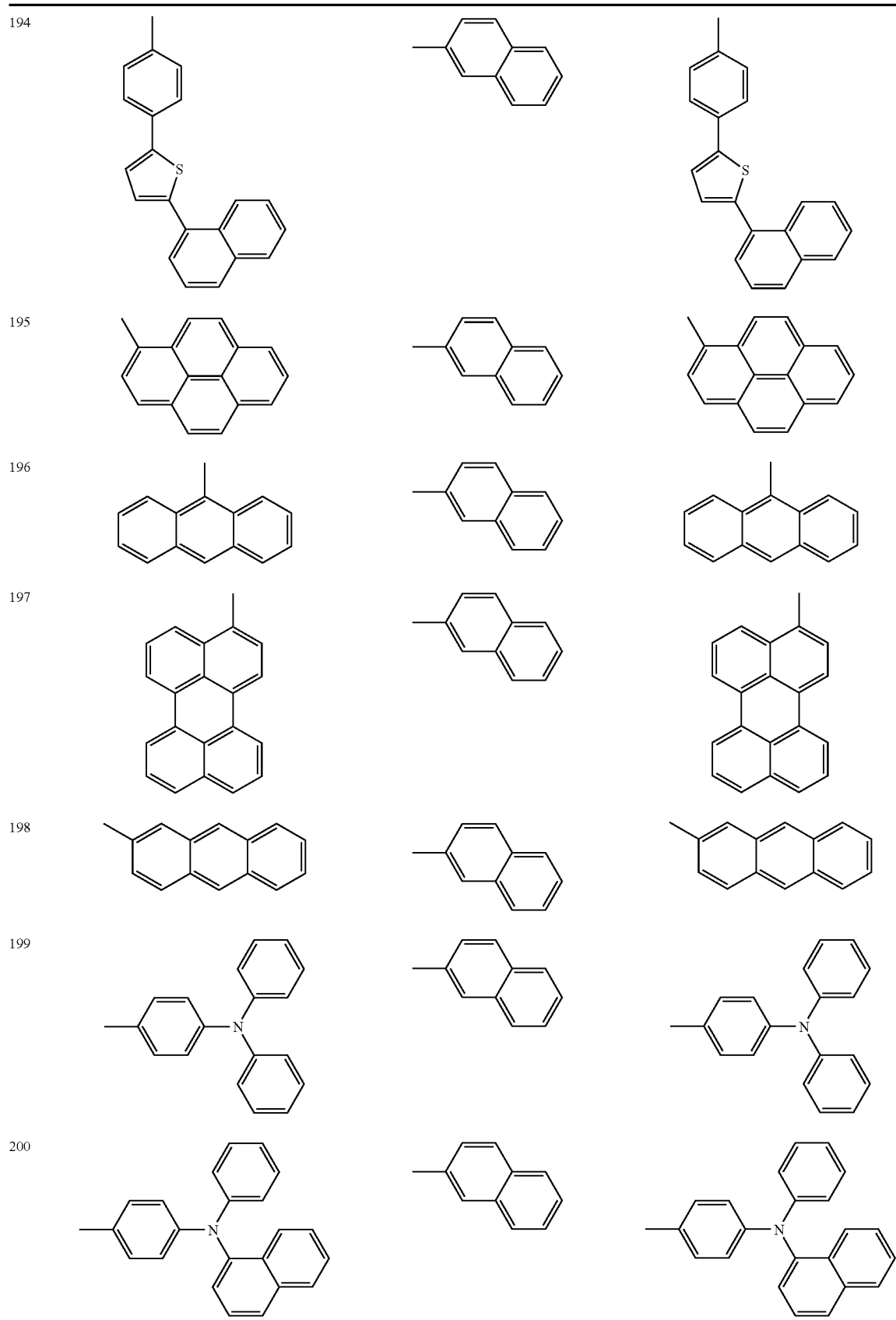

TABLE 1-continued

US 8,026,514 B2
TABLE 1-continued
| 213 | 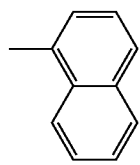 | 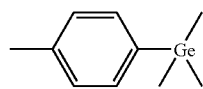 | 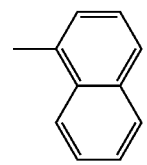 |
| 214 | 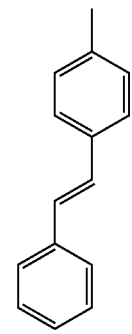 | 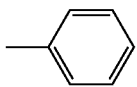 | 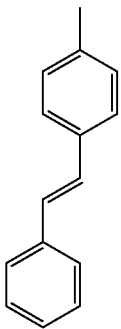 |
| 215 | 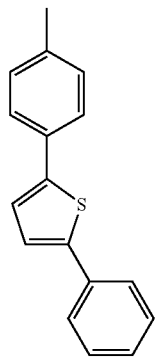 | 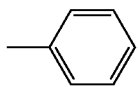 | 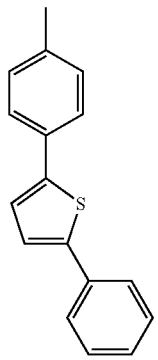 |
| 216 | 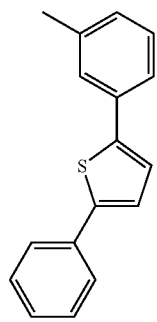 | 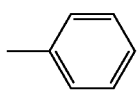 | 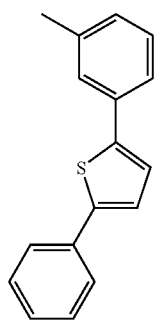 |
| 217 | 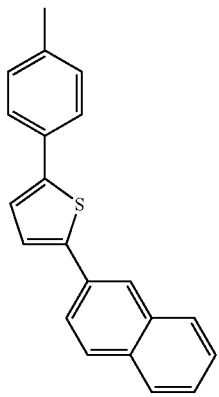 | 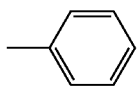 | 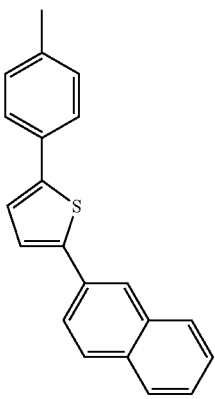 |

TABLE 1-continued
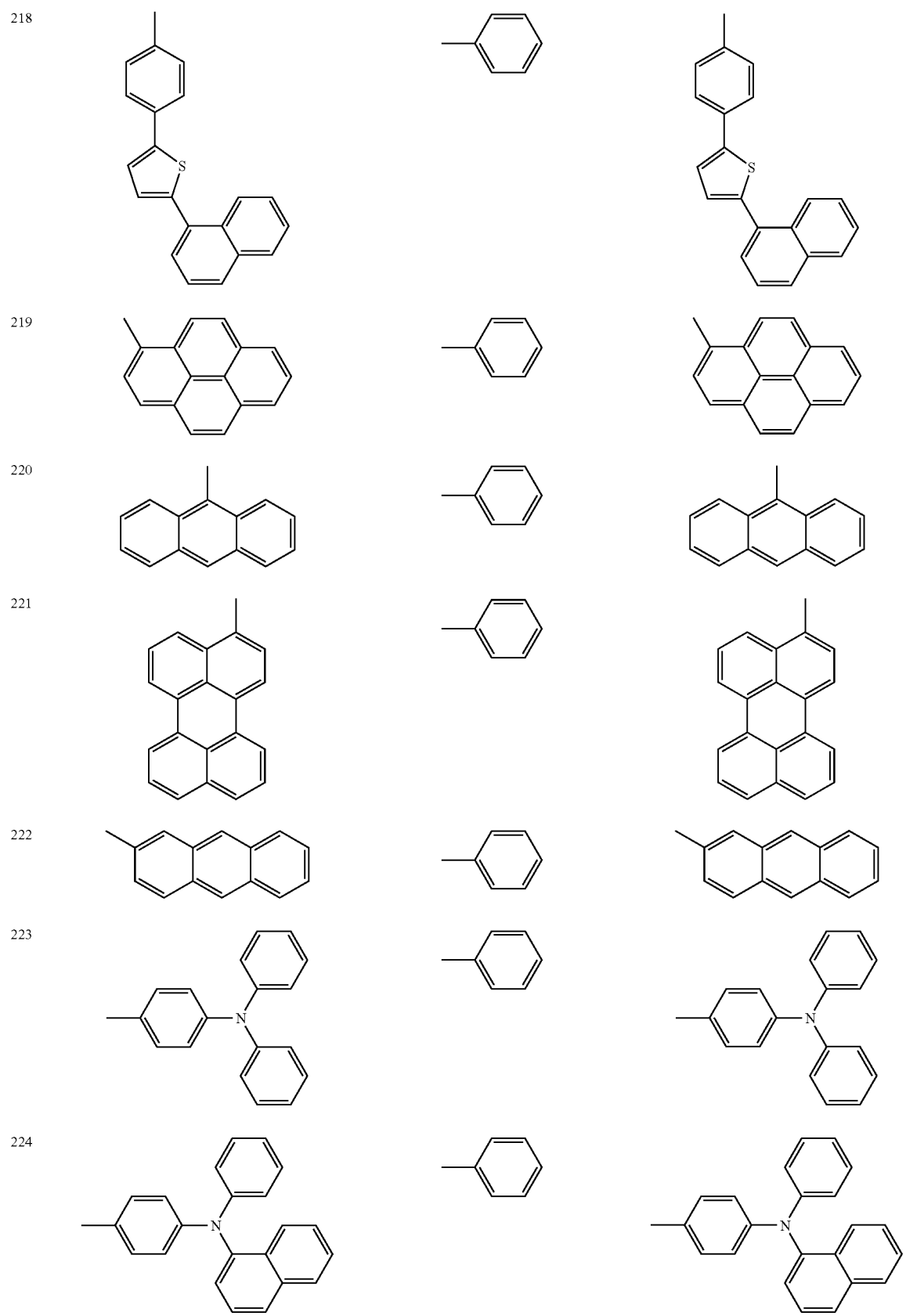

TABLE 1-continued
| 225 | 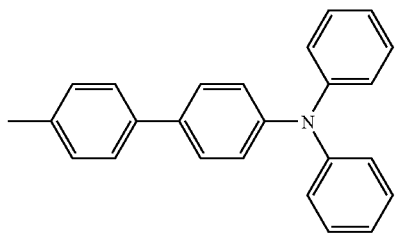 | 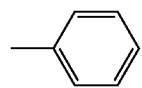 | 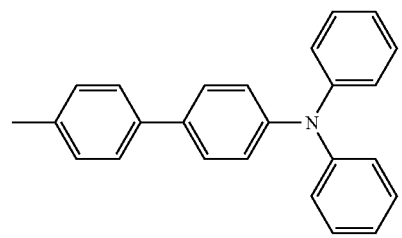 |
| --- | --- | --- | --- |
| 226 | 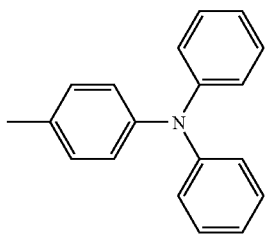 | 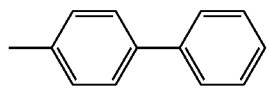 | 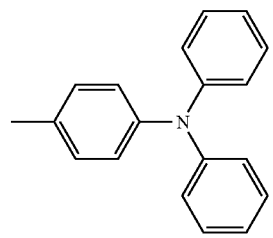 |
| 227 | 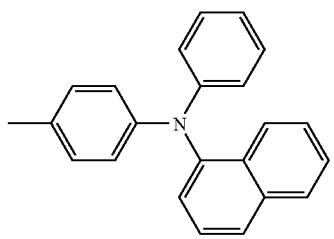 | 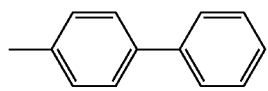 | 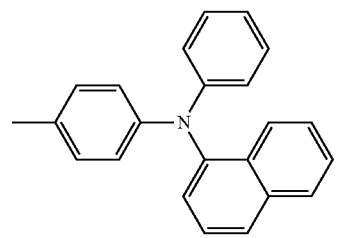 |
| 228 | 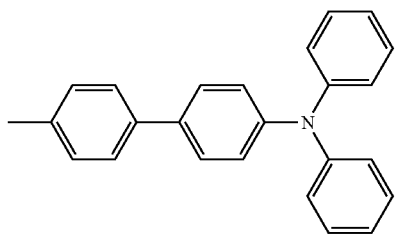 | 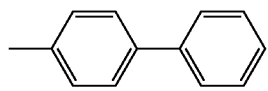 | 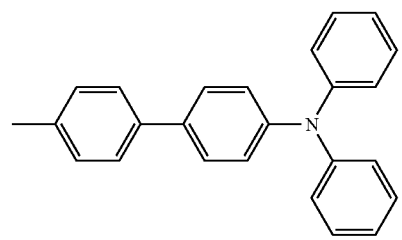 |
| 229 | 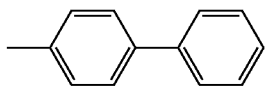 | 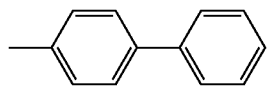 | 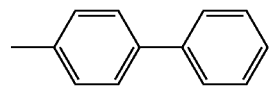 |
| 230 | 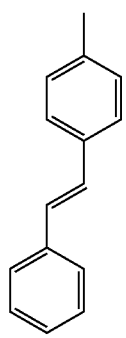 | 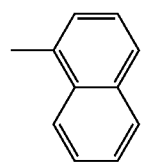 | 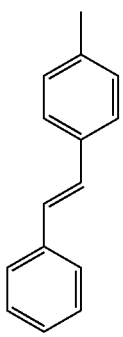 |

TABLE 1-continued
| 231 | 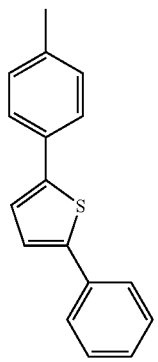 | 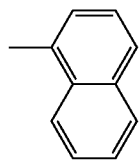 | 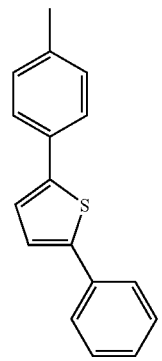 |
| 232 | 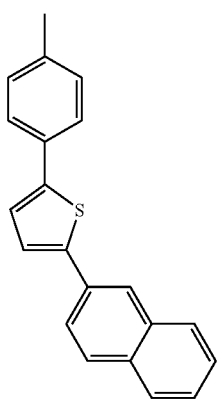 | 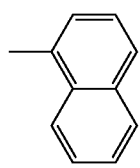 | 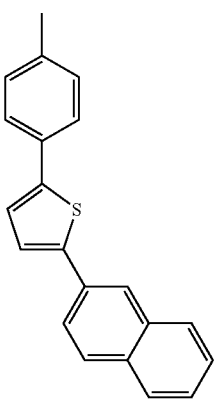 |
| 233 | 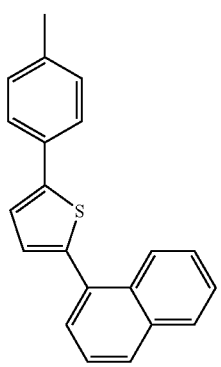 | 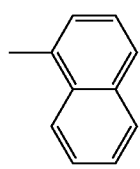 | 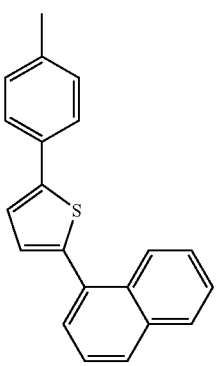 |
| 234 | 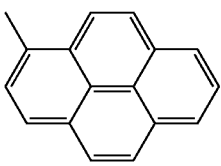 | 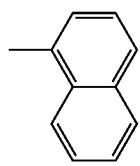 | 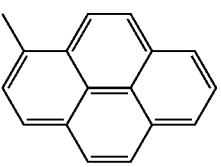 |
| 235 | 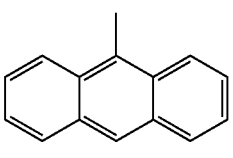 | 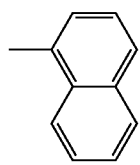 | 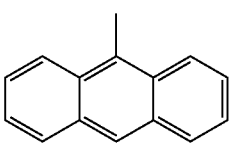 |

US 8,026,514 B2
TABLE 1-continued
| 236 | 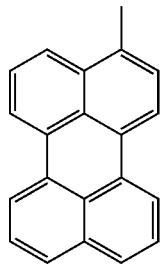 | 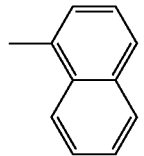 | 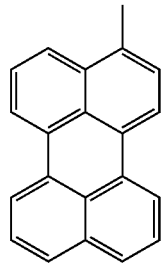 |
| --- | --- | --- | --- |
| 237 | 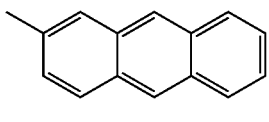 | 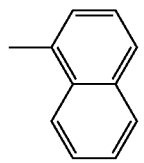 | 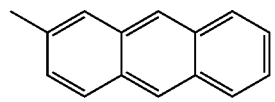 |
| 238 | 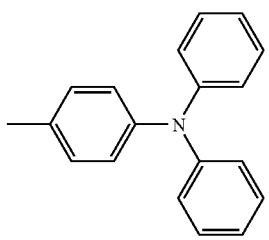 | 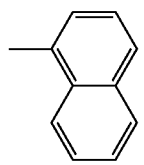 | 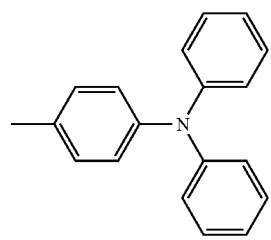 |
| 239 | 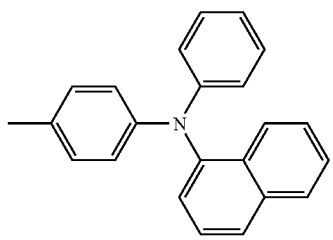 | 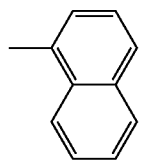 | 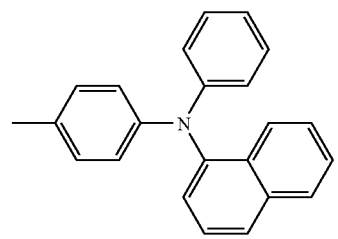 |
| 240 | 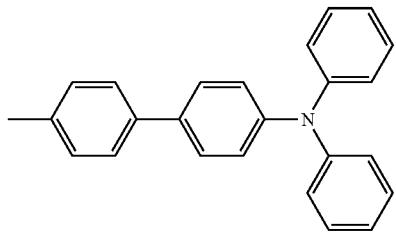 | 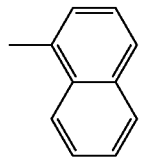 | 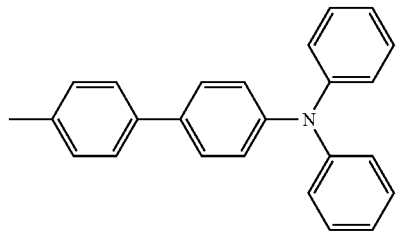 |
| 241 | 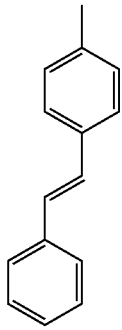 | 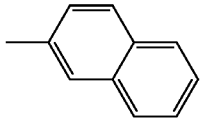 | 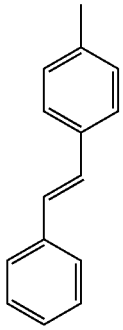 |

TABLE 1-continued
| 242 | 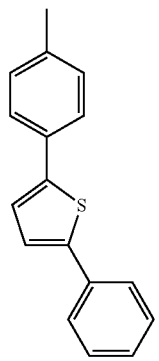 | 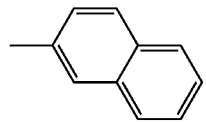 | 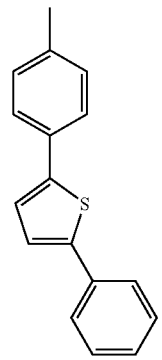 |
| 243 | 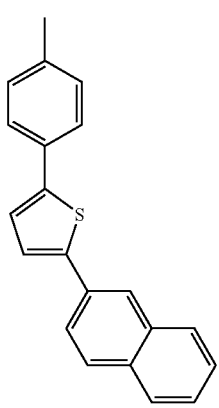 | 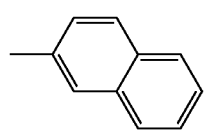 | 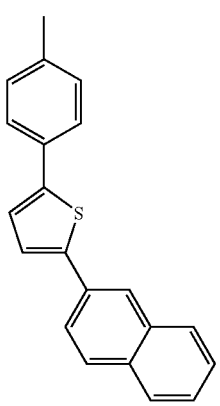 |
| 244 | 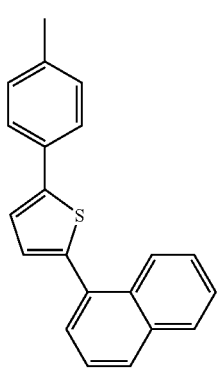 | 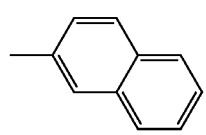 | 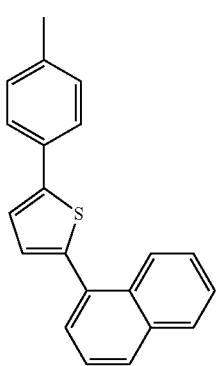 |
| 245 | 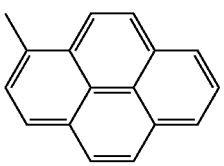 | 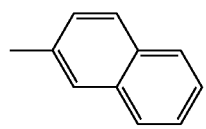 | 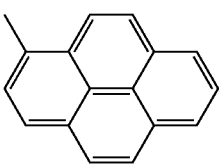 |
| 246 | 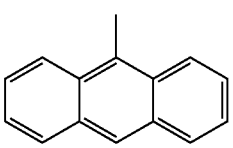 | 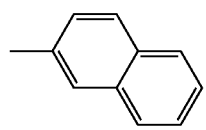 | 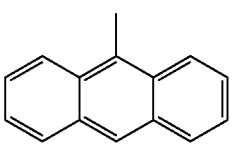 |

US 8,026,514 B2
TABLE 1-continued
| | | | |
|---|---|---|---|
| 247 | 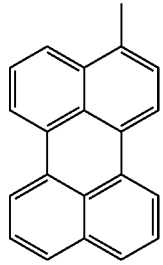 | 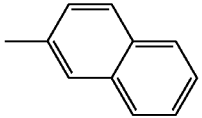 | 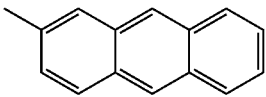 |
| 248 | 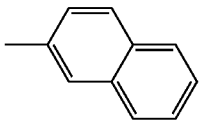 | | |
| 249 | 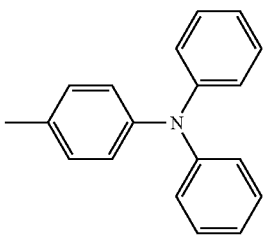 | | 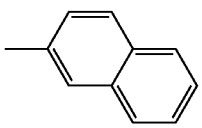 |
| 250 | 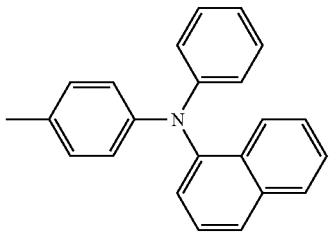 | | 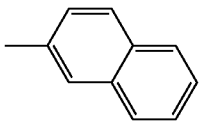 |
| 251 | 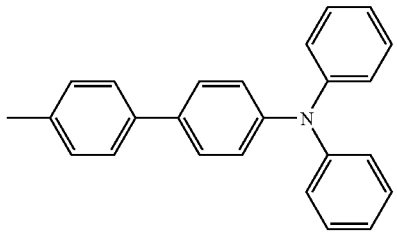 | | 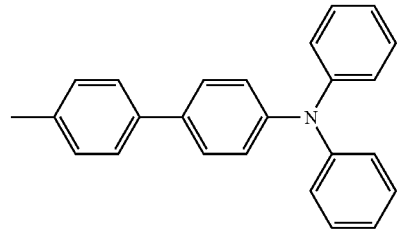 |
| 252 | 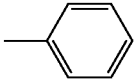 | | 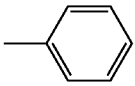 |
| 253 | 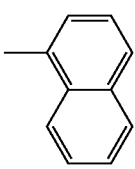 | | 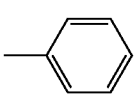 |
| 254 | 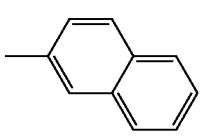 | | 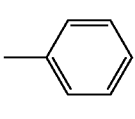 |
| 255 | 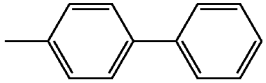 | | 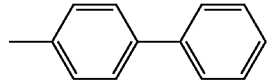 |

TABLE 1-continued
| | 301 | | 302 |
|---|---|---|---|
| 256 | 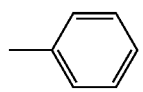 | 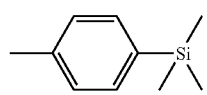 | 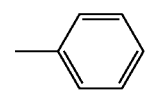 |
| 257 | 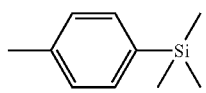 | 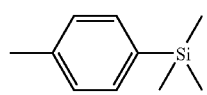 | 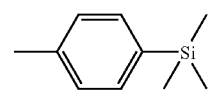 |
| 258 | 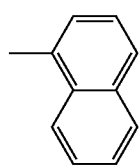 | 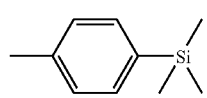 | 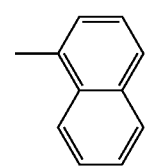 |
| 259 | 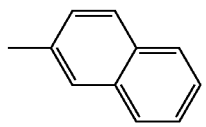 | 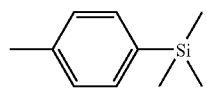 | 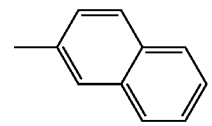 |
| 260 | 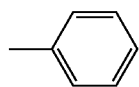 | 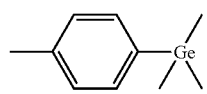 | 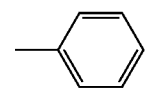 |
| 261 | 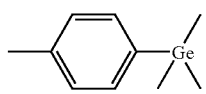 | 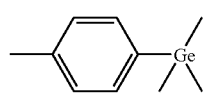 | 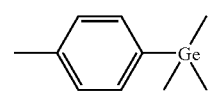 |
| 262 | 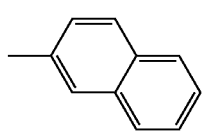 | 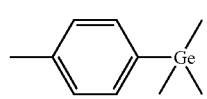 | 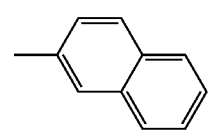 |
| 263 | 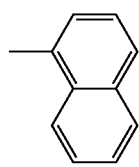 | 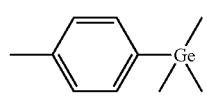 | 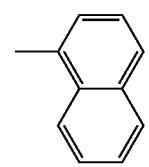 |
| 264 | 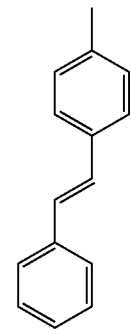 | 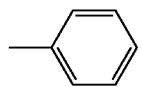 | 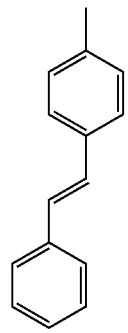 |

TABLE 1-continued
| | 303 | | 304 |
|---|---|---|---|
| 265 | 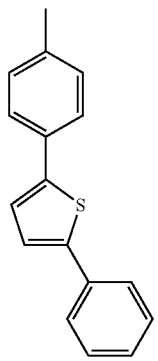 | 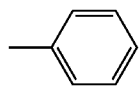 | |
| 266 | 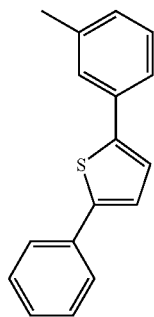 | 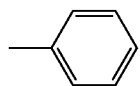 | |
| 267 | 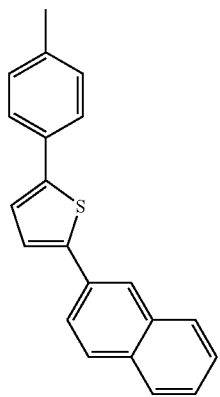 | 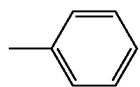 | |
| 268 | 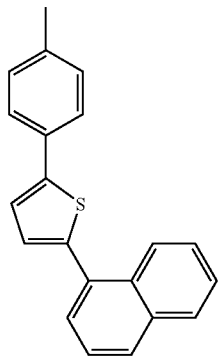 | 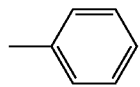 | |
| 269 | 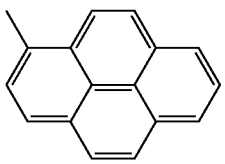 | 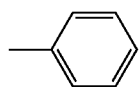 | |

TABLE 1-continued
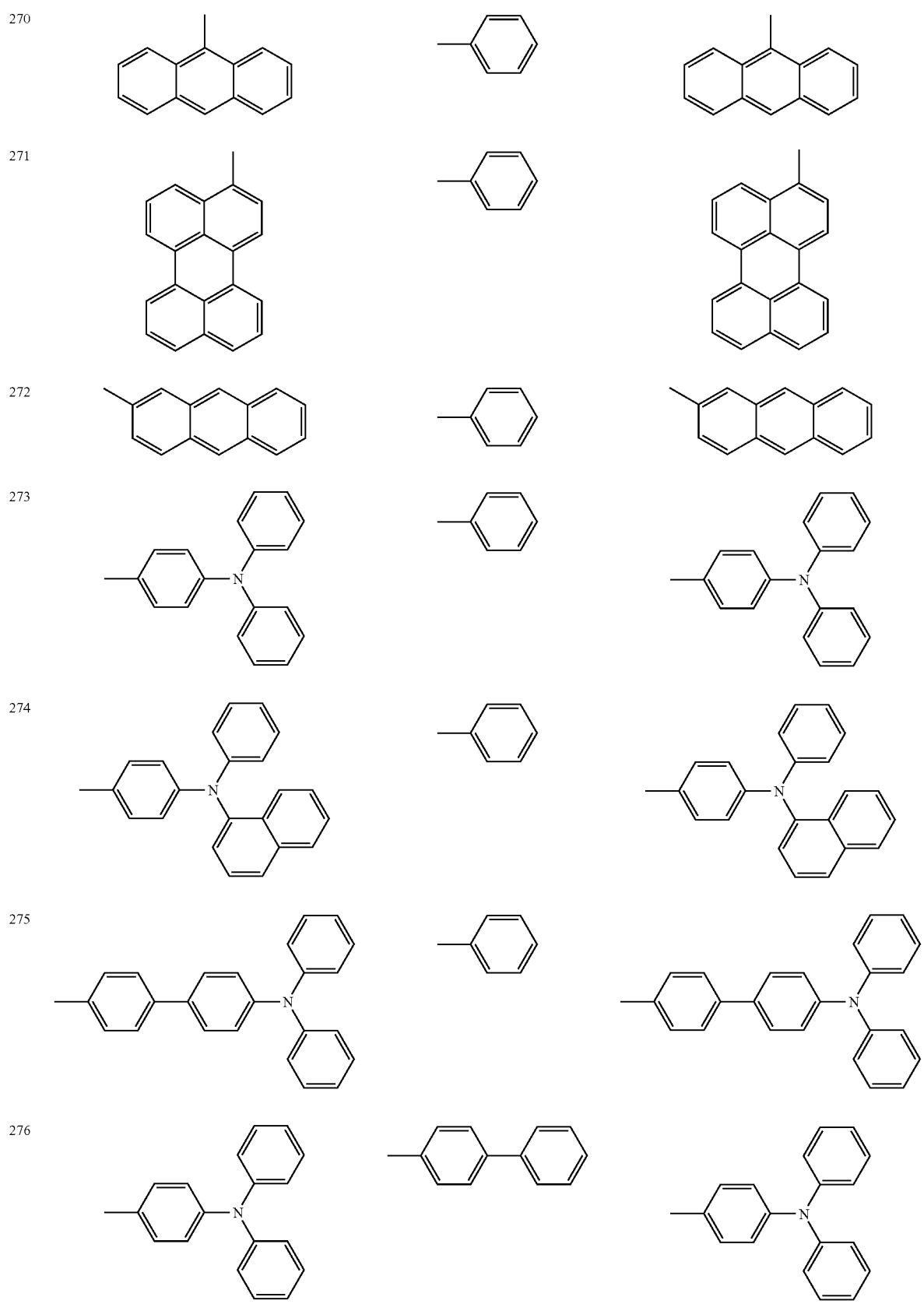

TABLE 1-continued
| 277 | 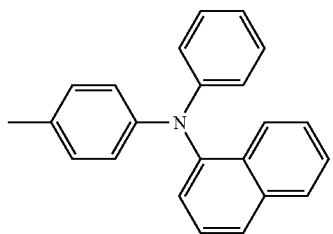 | 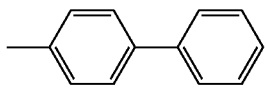 | 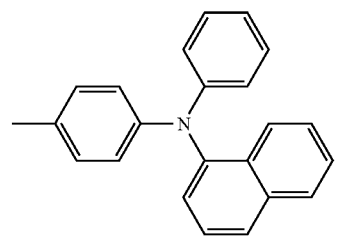 |
| 278 | 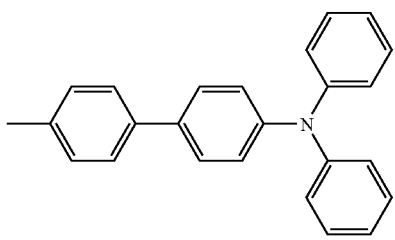 | 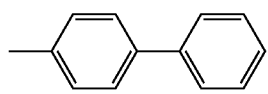 | 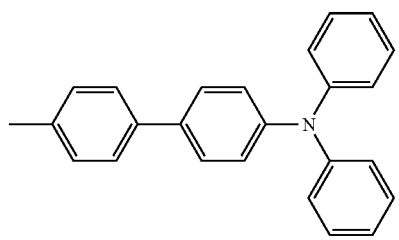 |
| 279 | 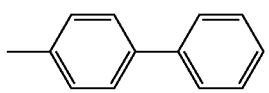 | 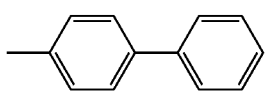 | 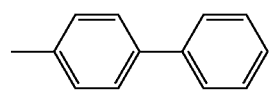 |
| 280 | 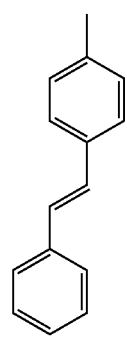 | 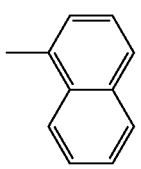 | 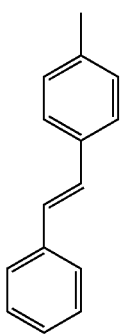 |
| 281 | 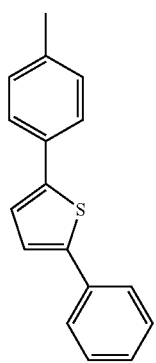 | 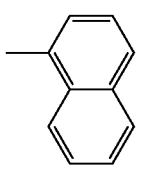 | 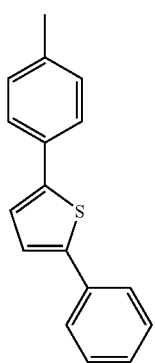 |

TABLE 1-continued
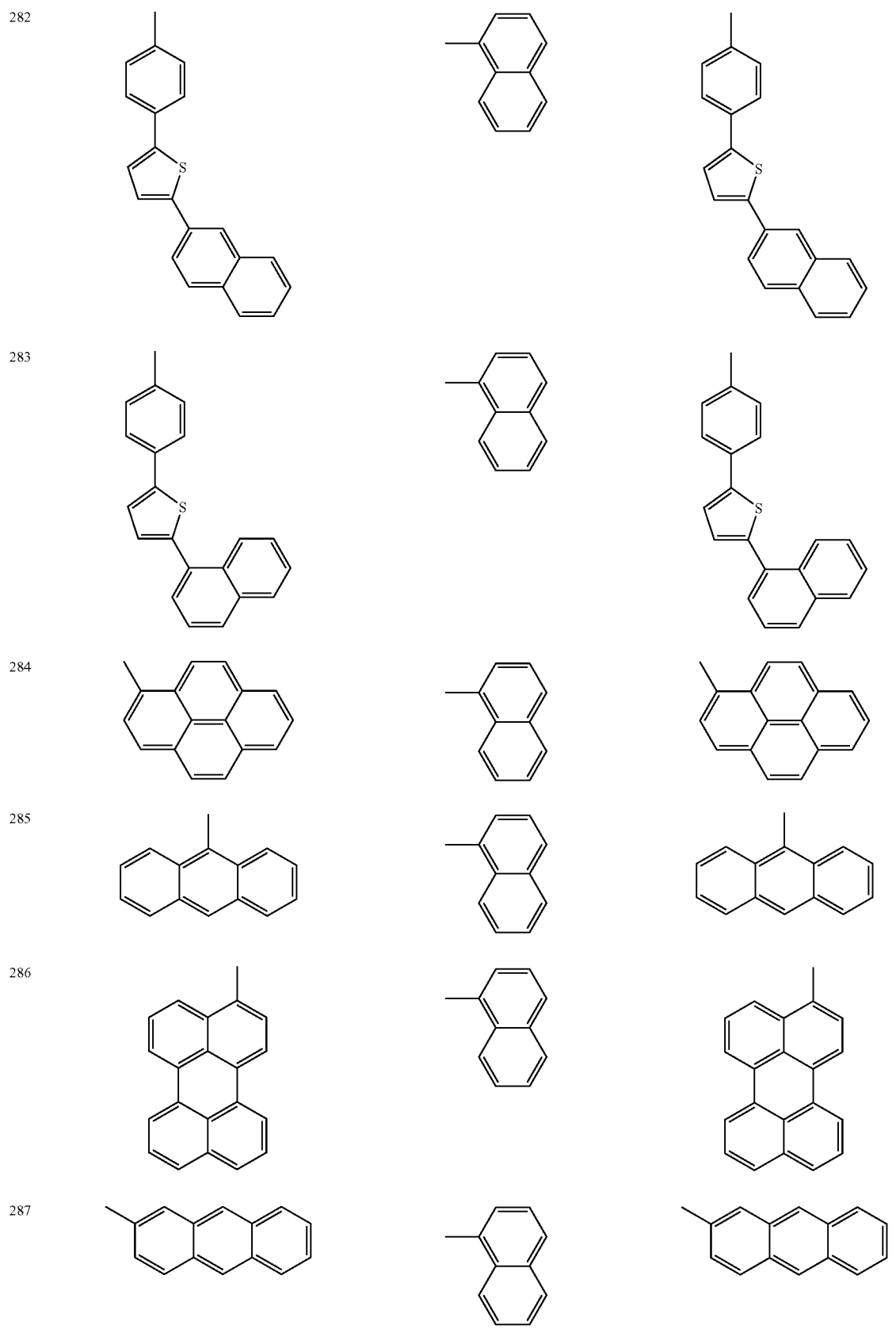

TABLE 1-continued
| | 311 | | 312 |
|---|---|---|---|
| 288 | 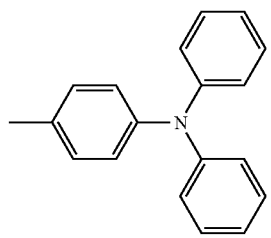 | 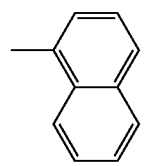 | 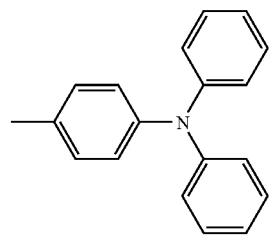 |
| 289 | 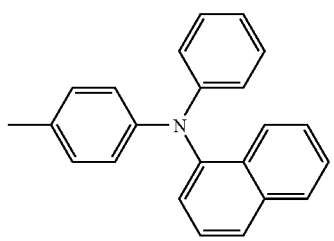 | 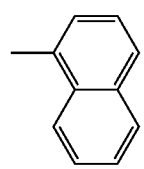 | 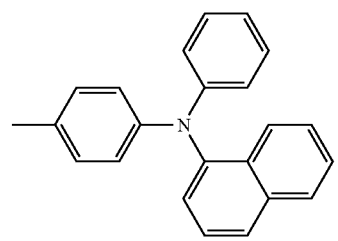 |
| 290 | 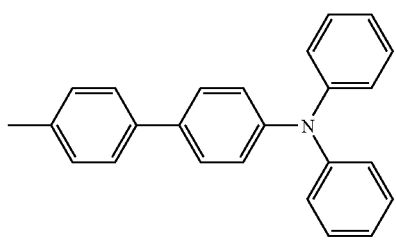 | 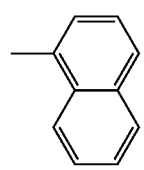 | 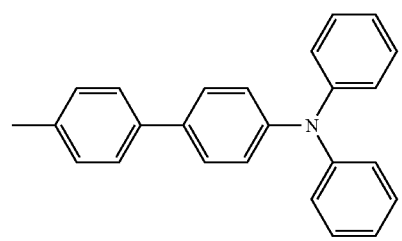 |
| 291 | 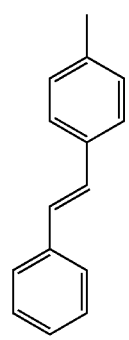 | 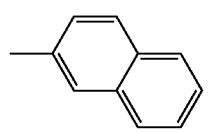 | 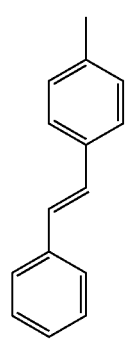 |
| 292 | 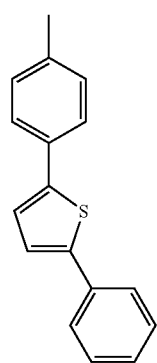 | 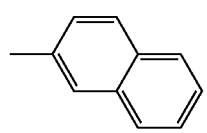 | 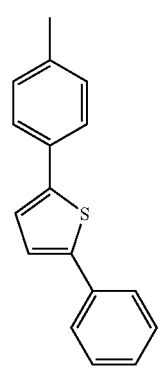 |

TABLE 1-continued
| | | | |
|---|---|---|---|
| 293 | 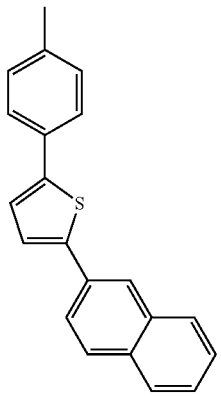 | 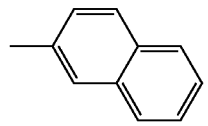 | 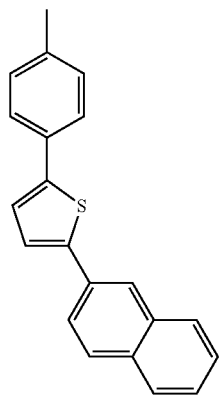 |
| 294 | 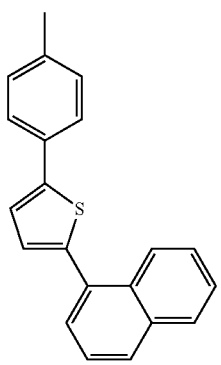 | 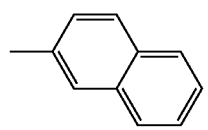 | 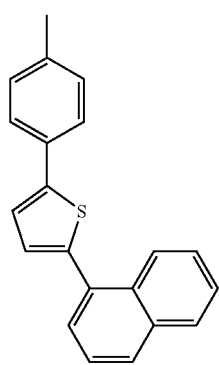 |
| 295 | 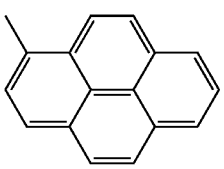 | 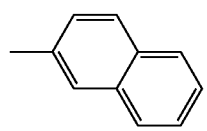 | 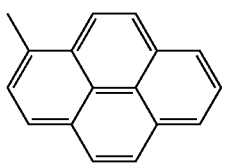 |
| 296 | 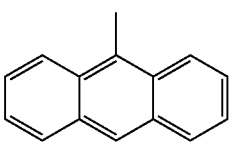 | 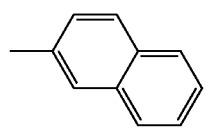 | 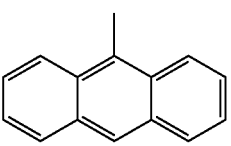 |
| 297 | 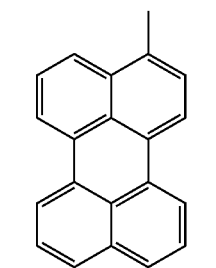 | 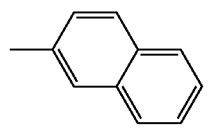 | 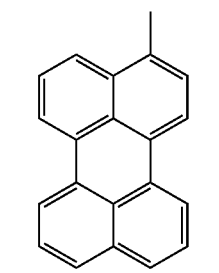 |
| 298 | 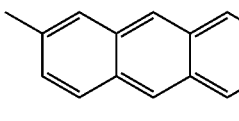 | 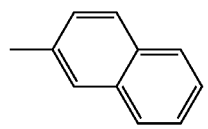 | 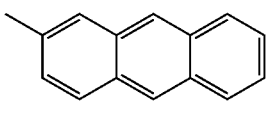 |

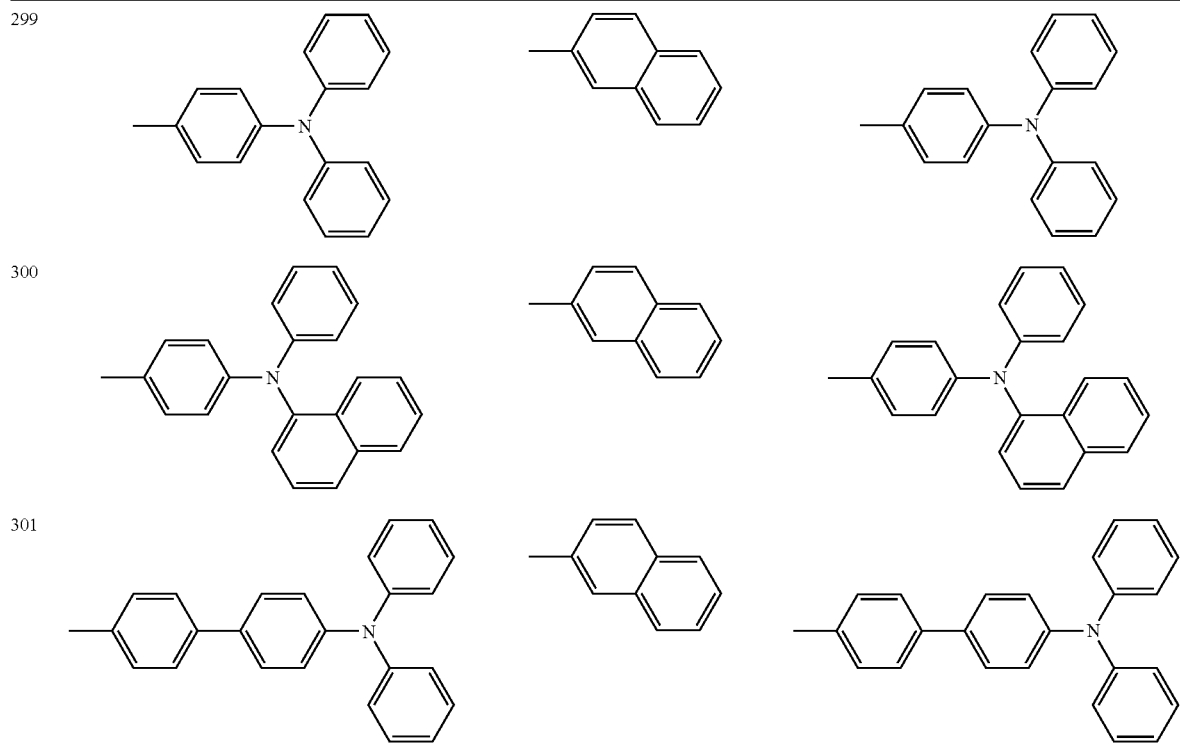

7. An organic electronic device comprising a first electrode, a second electrode and one or more organic material layers interposed therebetween, wherein at least one organic material layer comprises the diamine derivative of claim 1.

8. The organic electronic device according to claim 7, wherein the organic electronic device has a normal structure prepared by sequentially laminating an anode, one or more organic material layers, and a cathode on a substrate.

9. The organic electronic device according to claim 7, wherein the organic electronic device has an inverted structure prepared by sequentially laminating a cathode, one or more organic material layers, and an anode on a substrate.

10. The organic electronic device according to claim 7, wherein the organic material layer comprises at least one of a hole injecting layer, a hole transporting layer, and a hole injecting and hole transporting layer, and at least one of the layers comprises the diamine derivative of Formulae 2, 3, 5 and 6.

11. The organic electronic device according to claim 7, wherein the organic material layer comprises a light emitting layer, and the light emitting layer comprises the diamine derivative of Formulae 2, 3, 5 and 6.

12. The organic electronic device according to claim 7, wherein the organic material layer comprises an electron transporting layer, and the electron transporting layer comprises the diamine derivative of Formulae 2, 3, 5 and 6.

13. The organic electronic device according to claim 7, wherein the organic electronic device is selected from the group consisting of an organic light emitting device, an organic photovoltaic cell, an organic photoconductor (OPC) and an organic transistor.

14. An organic electronic device comprising a first electrode, a second electrode and one or more organic material layers interposed therebetween, wherein at least one organic material layer comprises the diamine derivative of claim 6.

15. The diamine derivative according to claim 1, wherein at least one of L1 and L2 of Formulae 2, 3, 5 and 6 is a $C_6$~$C_{20}$ arylene group, the rest is a direct bond or a $C_6$~$C_{20}$ arylene group; and Ar1, Ar2, Ar3 and Ar4 are same or different from each other, and are each a $C_6$~$C_{30}$ aryl group unsubstituted or substituted with a $C_6$~$C_{20}$ aryl amine group, —SiRR'R" or —GeRR'R"; a $C_5$~$C_{20}$ heterocyclic group comprising O, N or S; or a condensed ring formed by fusing a $C_4$~$C_{20}$ alkylene group with a $C_6$~$C_{20}$ aryl group, wherein R, R', and R" are same or different from each other, and are each independently hydrogen, a $C_1$~$C_{20}$ alkyl group.

16. An organic electronic device comprising a first electrode, a second electrode and one or more organic material layers interposed therebetween, wherein at least one organic material layer comprises the diamine derivative of claim 2.

17. An organic electronic device comprising a first electrode, a second electrode and one or more organic material layers interposed therebetween, wherein at least one organic material layer comprises the diamine derivative of claim 15.

* * * * *